US007326716B2

(12) United States Patent
Old et al.

(10) Patent No.: US 7,326,716 B2
(45) **Date of Patent: *Feb. 5, 2008**

(54) TREATMENT OF INFLAMMATORY BOWEL DISEASE

(75) Inventors: David W. Old, Irvine, CA (US); Danny T. Dinh, Garden Grove, CA (US); Karen M. Kedzie, Rancho Santa Margarita, CA (US); Daniel W. Gil, Corona Del Mar, CA (US); Wha Bin Im, Irvine, CA (US)

(73) Assignee: Allergan, Inc., Irvine, CA (US)

(*) Notice: Subject to any disclaimer, the term of this patent is extended or adjusted under 35 U.S.C. 154(b) by 388 days.

This patent is subject to a terminal disclaimer.

(21) Appl. No.: 10/999,451

(22) Filed: Nov. 29, 2004

(65) Prior Publication Data

US 2005/0171062 A1 Aug. 4, 2005

Related U.S. Application Data

(63) Continuation of application No. 10/861,957, filed on Jun. 3, 2004, now Pat. No. 7,179,820, which is a continuation of application No. 10/763,702, filed on Jan. 22, 2004, now Pat. No. 6,977,260, and a continuation of application No. 10/456,275, filed on Jun. 6, 2003, now Pat. No. 6,747,037.

(51) Int. Cl.
*A61K 31/445* (2006.01)
*A61K 31/505* (2006.01)
*C07D 211/08* (2006.01)
*C07D 211/40* (2006.01)
*C07D 211/68* (2006.01)

(52) U.S. Cl. .................. 514/273.3; 514/318; 514/319; 514/322; 514/324; 514/327; 546/192; 546/193; 546/196; 546/202; 546/205; 546/210; 546/212; 546/213; 546/214; 546/216

(58) Field of Classification Search ................ 546/192, 546/193, 196, 202, 205, 210, 212, 213, 214, 546/216; 514/277, 318, 319, 322, 324, 327
See application file for complete search history.

(56) References Cited

U.S. PATENT DOCUMENTS 4,994,274 A 2/1991 Chan et al. ................ 424/427

(Continued)

FOREIGN PATENT DOCUMENTS

WO 2004/063158 7/2004

(Continued)

OTHER PUBLICATIONS

Wolff, Manfred E. "Burger's Medicinal Chemistry, 5ed, Part I", John Wiley & Sons, 1995, pp. 975-977.*

(Continued)

*Primary Examiner*—Janet L. Andres
*Assistant Examiner*—Raymond Covington
(74) *Attorney, Agent, or Firm*—Brent A. Johnson; Martin A. Voet

(57) ABSTRACT

The present invention provides a method of treating inflammatory bowel disease which comprises administering to an animal having ocular hypertension or glaucoma therapeutically effective amount of a piperidinyl prostaglandin E analog.

28 Claims, 24 Drawing Sheets

| Structure | Binding Data (IC50 in nM) | | | | Functional Data (EC50 in nM) | | | | | | |
|---|---|---|---|---|---|---|---|---|---|---|---|
| | hEP2 | hEP3D | hEP4 | hFP | hEP1 | hEP2 | hEP3A | hEP4 | hTP | hIP | hDP |
|  | | | | NA | NA | NA | NA | NA | >10000 | NA | NA |
|  | | | | NA | NA | NA | NA | NA | 653 | NA | NA |
|  | | | | NA | NA | NA | NA | NA | 2474 | NA | NA |

U.S. PATENT DOCUMENTS

| | | | | |
|---|---|---|---|---|
| 5,028,624 A | 7/1991 | Chan et al. | ................. | 514/530 |
| 5,034,413 A | 7/1991 | Chan et al. | ................. | 514/530 |
| 5,446,041 A | 8/1995 | Chan et al. | ................. | 514/530 |
| 6,747,037 B1 * | 6/2004 | Old et al. | ................... | 514/277 |
| 6,977,260 B2 * | 12/2005 | Old et al. | ................... | 514/277 |
| 7,179,820 B2 * | 2/2007 | Old et al. | ................... | 514/327 |
| 2004/0142969 A1 | 7/2004 | Elworthy | | |

FOREIGN PATENT DOCUMENTS

| | | |
|---|---|---|
| WO | WO2004/085430 | 7/2004 |
| WO | 2005/072735 | 8/2005 |
| WO | 2005/121086 | 12/2005 |

OTHER PUBLICATIONS

Banker (Modern Pharmaceutics) Banker, G.S. et al, "Modern Pharmaceutics, 3ed.", Marcel Dekker, New York, 1996, pp. 451 and 596.*

Bernstein, Exp. Opinion , abstract and first paragraph, pp. 1081-1096.*

Dey., C. Brit. Jol. Pharmacology, (2006) pp. 611-623.*

ONO-4819CD, Dec. 2006, (Clinical Trials.gov).*

Kabashima, J. clinical Invest., vol. 109 No. 7, pp. 883-893.*

Huang, et al., Synth. Commun. 1989, 19, pp. 3485-3496.

Chourasia,M.K., et. al., *Pharmaceutical approaches to colon targeted drug delivery systems*, J. Pharm Pharmaceut Sci 6(1):33-66, 2003.

Shareef, M.A., et al., *Colonic Drug Delivery: an updated review*, AAPS PharmSci 2003; 35(2) Article 17, pp. 161-186.

Remington's, 16[the] Edition, Mack Publishing, Easton, PA, 1980.

Bito, L.Z., *Biological Protection with Prostaglandins*, Cohen, M.M., ed., Boca Raton, Fla, CRC Press Inc., 1985, pp. 231-252.

Bito, L.Z., *Applied Pharmacology in the Medical Treatment of Glaucomas*, Drance, S.M. and Neufeld, A.H. eds, New York, Grune & Stratton, 1984, pp. 477-505.

Nilsson et al, Invest. *Ophthalmol. Vis. Sci.* (suppl), 284 (1987).

Bito, L.Z., *Arch. Opthalmol.* 105, 1036 (1987).

Siebold et al, *Prodrug* 5 3 1989.

Huang et al, Synth. Commun., "Preparation of Optically Pure ω-Hydroxymethyl Lactams"m 1989, 19, 3485-3496.

* cited by examiner

| Structure | Binding Data (IC50 in nM) | | | Functional Data (EC50 in nM) | | | | | | | | |
|---|---|---|---|---|---|---|---|---|---|---|---|---|
| | hEP2 | hEP3D | hEP4 | hFP | hEP1 | hEP2 | hEP3A | hEP4 | hTP | hIP | hDP |
|  | | | | NA | NA | NA | NA | NA | >10000 | NA | NA |
|  | | | | NA | NA | NA | NA | NA | 653 | NA | NA |
|  | | | | NA | NA | NA | NA | NA | 2474 | NA | NA |

| | | | | | | | | |
|---|---|---|---|---|---|---|---|---|
| 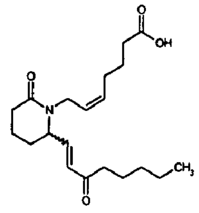 | NA | NA | NA | NA | 10000 | 88 | NA | NA |
| 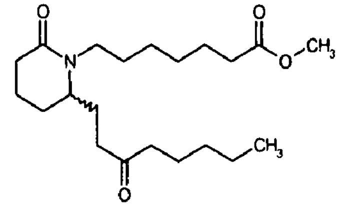 | NA | NA | NA | NA | NA | >1000<br>0 | NA | NA |
| 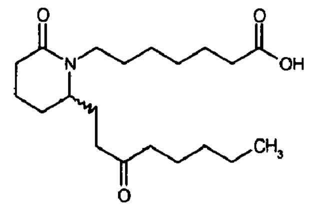 | NA | NA | NA | NA | >1000<br>0 | 565 | NA | NA |
| 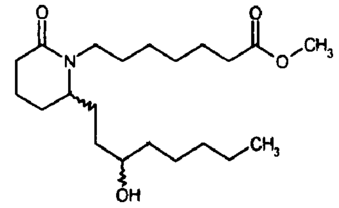 | NA | NA | NA | NA | 1842 | >1000<br>0 | NA | NA |

| | | | | | | | | | | | |
|---|---|---|---|---|---|---|---|---|---|---|---|
| 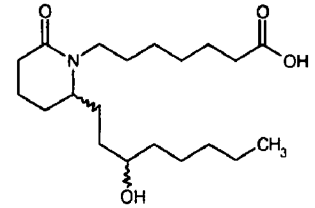 | NA | >10000 | 290 | NA | NA | >10000 | | 99 | 449 | | NA |
| 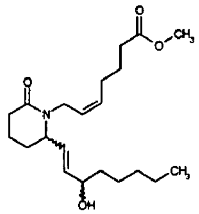 | | | | NA | NA | NA | NA | 815 | >10000 | NA | NA |
| 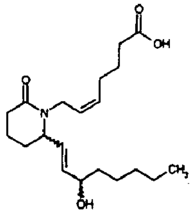 | NA | | 440 | NA | >10000 | NA | | 46 | 141 | NA | NA |
| 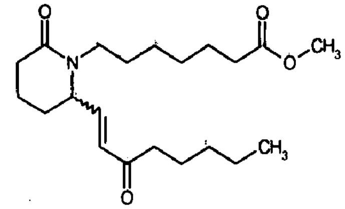 | | | | NA | NA | NA | NA | NA | >10000 | NA | NA |

| | | | | | | | | |
|---|---|---|---|---|---|---|---|---|
| 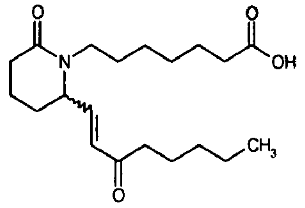 | NA | NA | NA | NA | 1290 | 238 | NA | NA |
| 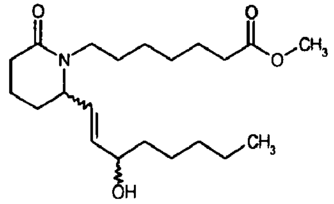 | NA | NA | NA | NA | 243 | NA | NA | NA |
| 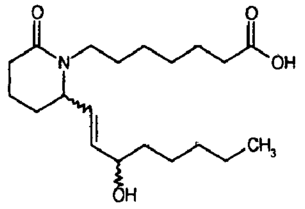 | NA | NA | NA | | 10 | 424 | >1000<br>0 | NA |
| 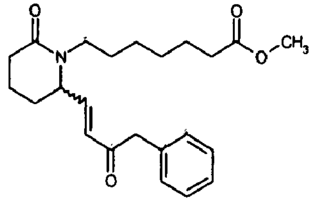 | NA | NA | NA | NA | NA | >1000<br>0 | NA | NA |

| | | | | | | | | | | | |
|---|---|---|---|---|---|---|---|---|---|---|---|
| 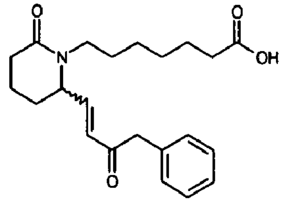 | | | | NA | NA | NA | NA | >1000<br>0 | 207 | NA | NA |
| 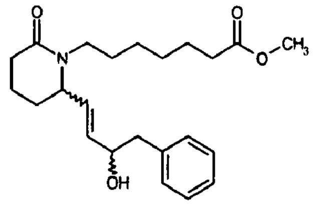 | NA | | 2200 | NA | NA | NA | NA | 34 | NA | NA | NA |
| 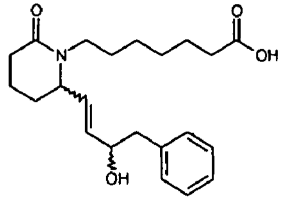 | NA | | 65 | NA | NA | NA | NA | 3 | 2126 | NA | NA |
| 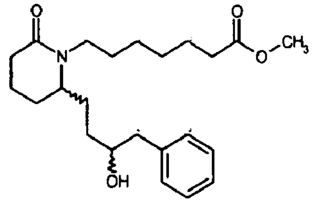 | NA | NA | >1000<br>0 | NA | NA | NA | NA | 863 | >1000<br>0 | NA | NA |

| | | | | | | | | | | |
|---|---|---|---|---|---|---|---|---|---|---|
| 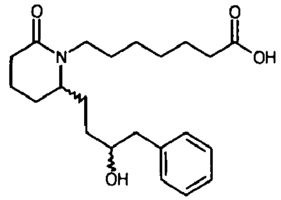 | >1000<br>0 | 1400 | NA | NA | NA | NA | 138 | 215 | NA | NA |
| 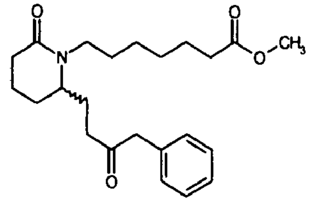 | | | NA | NA | NA | NA | NA | >1000<br>0 | NA | NA |
| 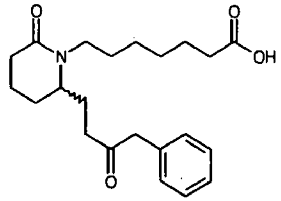 | | | NA | NA | NA | NA | | 218 | NA | NA |
| 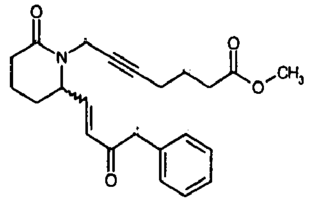 | | | NA | NA | NA | NA | NA | >1000<br>0 | NA | NA |

| | | | | | | | | | | | |
|---|---|---|---|---|---|---|---|---|---|---|---|
| 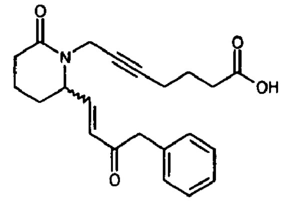 | | | | NA | NA | NA | NA | >1000<br>0 | 660 | NA | NA |
| 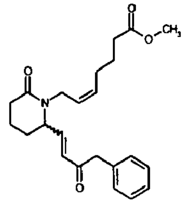 | | | | NA | NA | NA | NA | NA | 4911 | NA | NA |
| 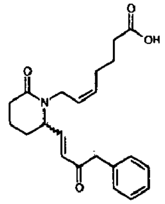 | | | | NA | NA | NA | NA | >1000<br>0 | | NA | NA |
| 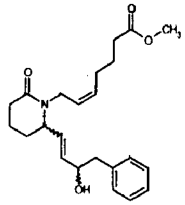 | NA | NA | 3400 | NA | NA | NA | NA | 464 | >1000<br>0 | NA | NA |

| | | | | | | | | | | | |
|---|---|---|---|---|---|---|---|---|---|---|---|
| 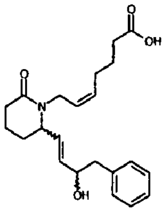 | NA | NA | 130 | NA | NA | NA | NA | 8 | 597 | NA | NA |
| 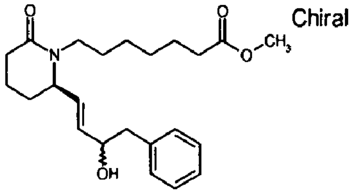 | NA | >1000<br>0 | 4600 | NA | NA | NA | NA | 274 | NA | NA | NA |
| 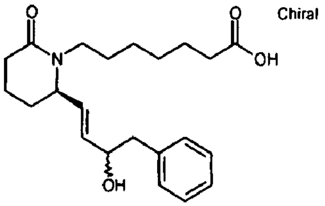 | NA | NA | 6800 | NA | NA | NA | NA | 0.56 | NA | NA | NA |
| 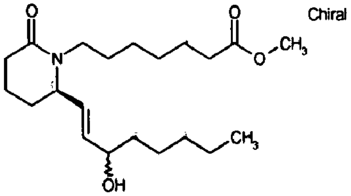 | NA | >1000<br>0 | 6500 | NA | NA | NA | NA | 385 | NA | NA | NA |

| | | | | | | | | | | | |
|---|---|---|---|---|---|---|---|---|---|---|---|
| 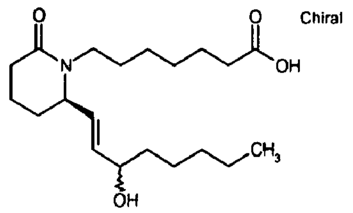 | NA | >1000<br>0 | >1000<br>0 | NA | NA | NA | >1000<br>0 | 10.4 | >1000<br>0 | NA | NA |
| 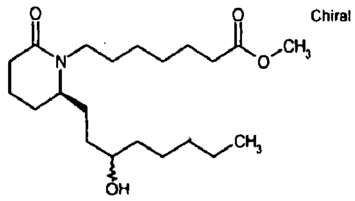 | NA | NA | >1000<br>0 | NA | NA | NA | NA | 2893 | NA | NA | NA |
| 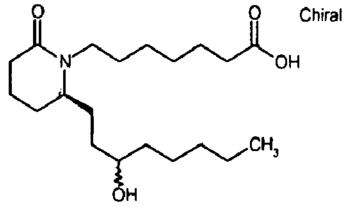 | >1000<br>0 | NA | 2500 | NA | NA | NA | NA | 481 | NA | NA | NA |
| 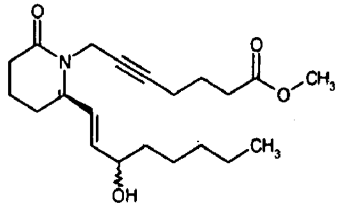 | | | | NA | NA | NA | NA | >1000<br>0 | NA | NA | NA |

| | | | | | | | | | | | |
|---|---|---|---|---|---|---|---|---|---|---|---|
| 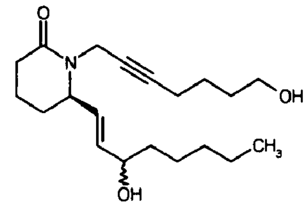 | | | | NA | NA | NA | NA | >10000 | NA | NA | NA |
| 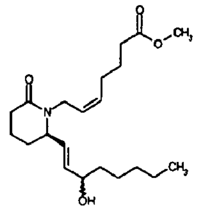 | NA | NA | 6000 | NA | NA | NA | NA | 649 | NA | NA | NA |
| 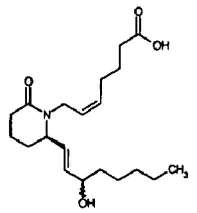 | NA | NA | 270 | NA | NA | NA | >10000 | 16.5 | >10000 | NA | NA |
| 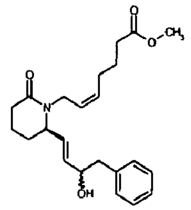 | NA | NA | 4600 | NA | NA | NA | NA | 593 | NA | NA | NA |

| | | | | | | | | | | | |
|---|---|---|---|---|---|---|---|---|---|---|---|
| 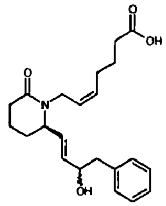 | NA | NA | 150 | NA | NA | NA | NA | 8.5 | NA | NA | NA |
| 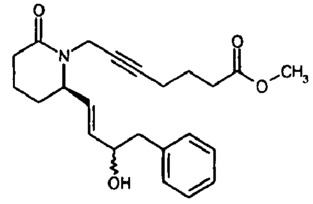 | NA | NA | >1000<br>0 | NA | NA | NA | NA | 3119 | NA | NA | NA |
| 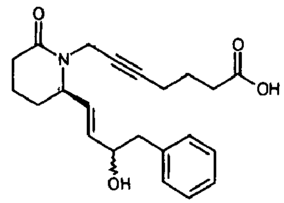 | NA | NA | 1000 | NA | NA | NA | NA | 81 | NA | NA | NA |
| 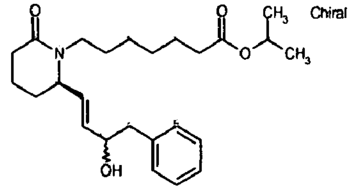  | NA | NA | 2800 | NA | NA | NA | NA | 246 | NA | NA | NA |

| | | | | | | | | | | | |
|---|---|---|---|---|---|---|---|---|---|---|---|
| 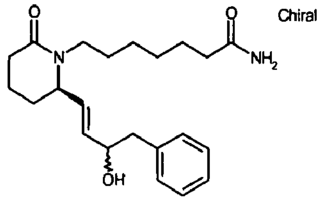 | NA | NA | 55 | NA | NA | NA | NA | 2 | NA | NA | NA |
| 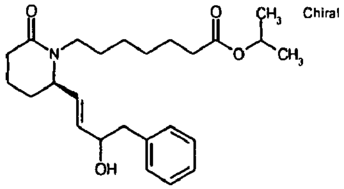 | | | | NA | NA | NA | NA | 164 | NA | NA | NA |
| 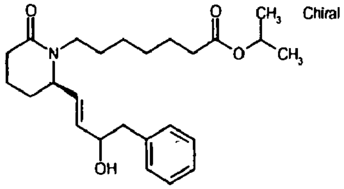 | | | | NA | NA | NA | NA | 339 | NA | NA | NA |
| 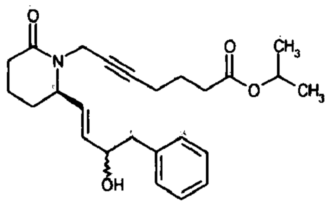 | | | | NA | NA | NA | NA | >1000<br>0 | NA | NA | >1000<br>0 |

| | | | | | | | | | | | |
|---|---|---|---|---|---|---|---|---|---|---|---|
| 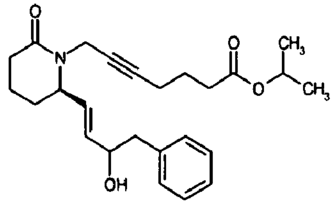 | | | | NA | NA | NA | NA | >10000 | NA | NA | NA |
| 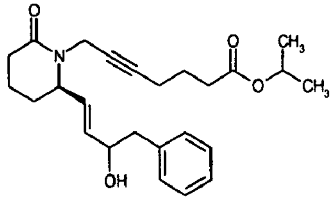 | | | | NA | NA | NA | NA | NA | NA | NA | NA |
| 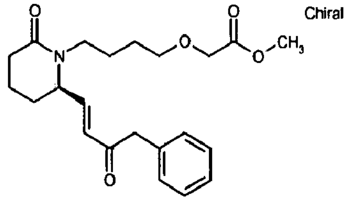 | | | | NA | NA | NA | NA | NA | >10000 | NA | NA |
| 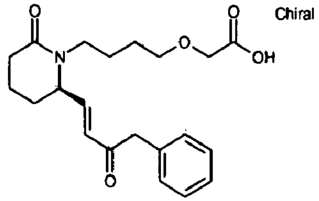 | NA | NA | 3800 | NA | NA | NA | >10000 | 300 | 2260 | NA | NA |

| | | | | | | | | | | | |
|---|---|---|---|---|---|---|---|---|---|---|---|
| 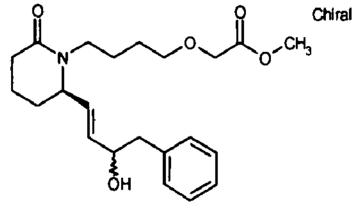 | NA | NA | 4200 | NA | NA | NA | NA | 1104 | NA | NA | NA |
| 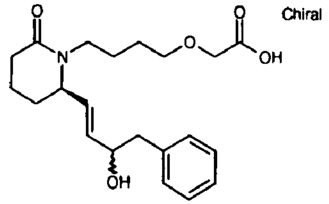 | NA | NA | 2300 | NA | NA | NA | NA | 145 | NA | NA | NA |
| 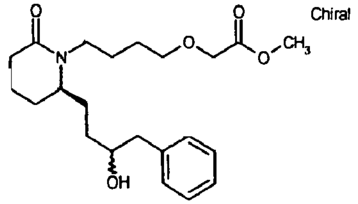 | | | | NA | NA | NA | >10000 | >10000 | NA | NA | NA |
| 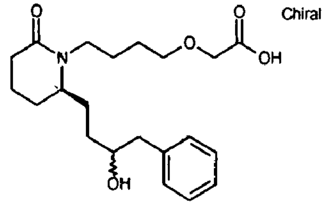 | | | | NA | NA | NA | NA | >10000 | NA | NA | NA |

| | | | | | | | | |
|---|---|---|---|---|---|---|---|---|
| 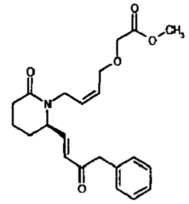 | NA | NA | NA | NA | NA | NA | NA | NA |
| 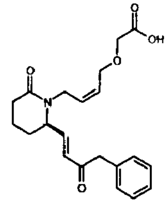 | NA | NA | NA | NA | 2556 | >1000<br>0 | NA | NA |
| 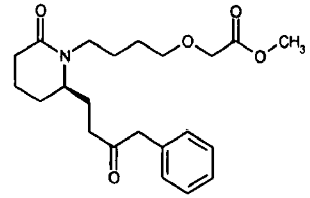 | NA | NA | NA | NA | 7542 | NA | NA | NA |
| 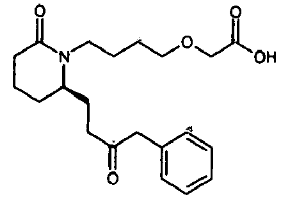 | NA | NA | NA | NA | 1975 | >1000<br>0 | NA | NA |

| | | | | | | | | |
|---|---|---|---|---|---|---|---|---|
| 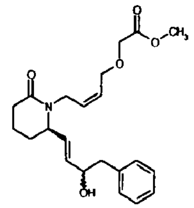 | NA | NA | NA | NA | NA | NA | NA | NA |
| 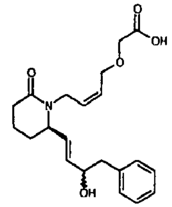 | NA | NA | NA | NA | >1000<br>0 | NA | NA | NA |
| 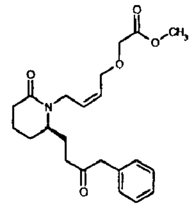 | NA | NA | NA | NA | NA | NA | NA | NA |
| 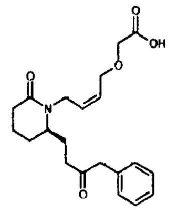 | NA | NA | NA | NA | >1000<br>0 | >1000<br>0 | NA | NA |

| | | | | | | | | |
|---|---|---|---|---|---|---|---|---|
| 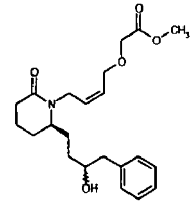 | NA | NA | NA | NA | NA | NA | NA | NA |
| 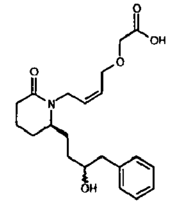 | NA | NA | NA | NA | >10000 | NA | NA | NA |
| 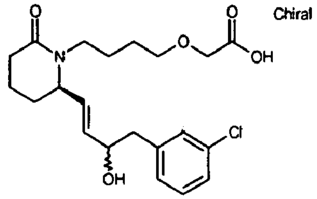 | NA | >10000 | >10000 | NA | 1.4 | 661 | NA | NA |
| 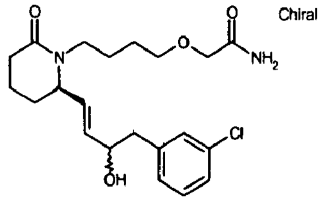 | NA | NA | NA | NA | 10 | >10000 | NA | NA |

| | | | | | | | | |
|---|---|---|---|---|---|---|---|---|
| 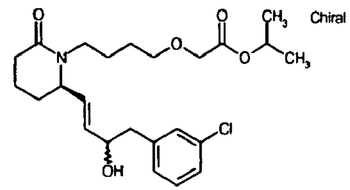 | NA | NA | NA | NA | 58 | NA | NA | NA |
| 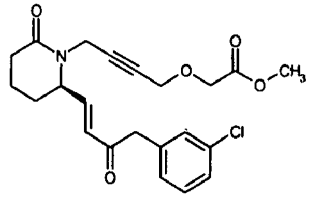 | NA | NA | NA | NA | NA | 1672 | NA | NA |
| 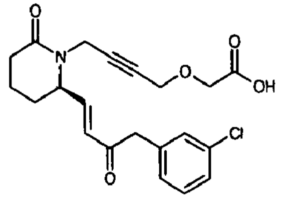 | NA | NA | NA | NA | 96 | 184 | NA | NA |
| 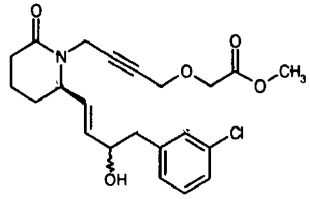 | NA | NA | NA | NA | 1868 | NA | NA | NA |

| | | | | | | | | |
|---|---|---|---|---|---|---|---|---|
| 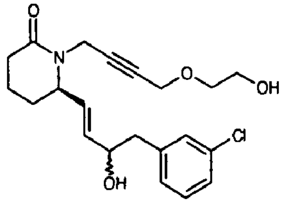 | NA | NA | NA | NA | 4553 | NA | NA | NA |
| 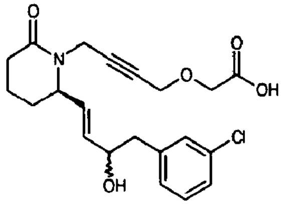 | NA | NA | NA | NA | 147 | 2916 | NA | NA |
| 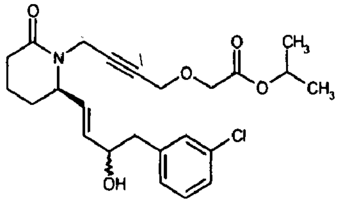 | NA | NA | NA | NA | >10000 | NA | NA | NA |
| 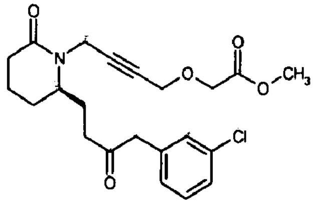 | NA | NA | NA | NA | NA | >10000 | NA | NA |

| | | | | | | | | |
|---|---|---|---|---|---|---|---|---|
| 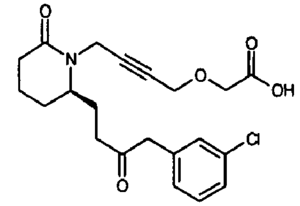 | NA | NA | NA | NA | 531 | 728 | NA | NA |
| 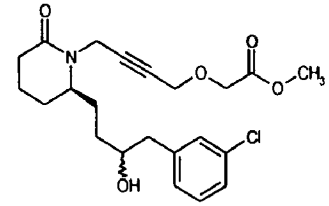 | NA | NA | NA | NA | 22523 | NA | NA | NA |
| 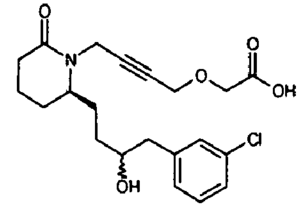 | NA | NA | NA | NA | 640 | 2672 | NA | NA |
| 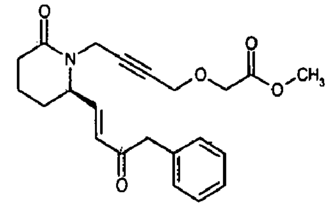 | NA | NA | NA | NA | NA | NA | NA | NA |

| | | | | | | | | |
|---|---|---|---|---|---|---|---|---|
| 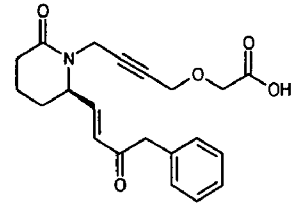 | NA | NA | NA | NA | 3147 | 3256 | NA | NA |
| 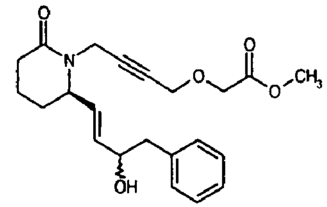 | NA | NA | NA | NA | >1000<br>0 | NA | NA | NA |
| 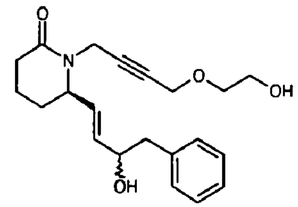 | NA | NA | NA | NA | NA | NA | NA | NA |
| 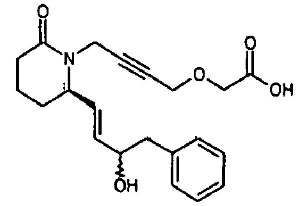 | NA | NA | NA | NA | 2709 | NA | NA | NA |

| | | | | | | | | |
|---|---|---|---|---|---|---|---|---|
| 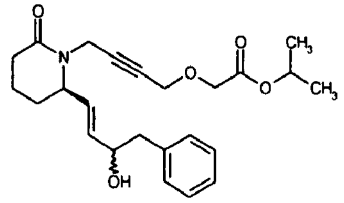 | NA | NA | NA | NA | NA | NA | NA | NA |
| 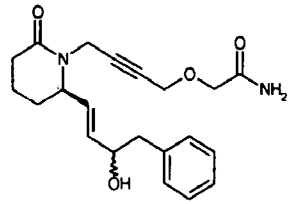 | NA | NA | NA | NA | >1000<br>0 | NA | NA | NA |
| 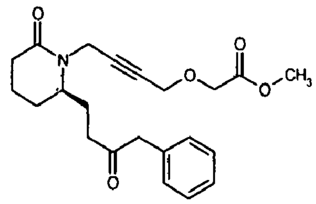 | NA | NA | NA | NA | NA | NA | NA | NA |
| 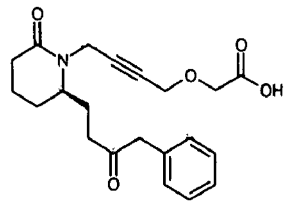 | NA | NA | NA | NA | NA | >1000<br>0 | NA | NA |

| | | | | | | | | |
|---|---|---|---|---|---|---|---|---|
| 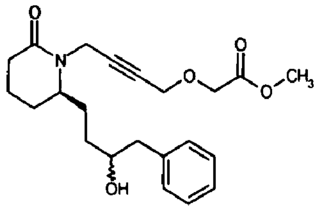 | NA | NA | NA | NA | NA | NA | NA | NA |
| 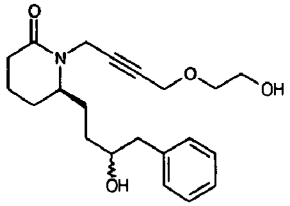 | NA | NA | NA | NA | 108 | NA | NA | NA |
| 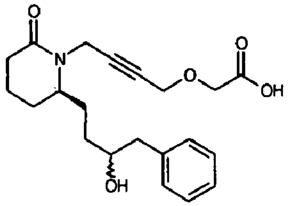 | NA | NA | NA | NA | >1000<br>0 | NA | NA | NA |
| 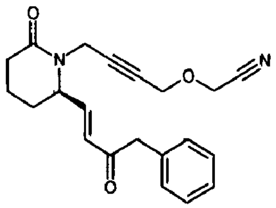 | NA | NA | NA | NA | NA | NA | NA | NA |

| | | | | | | | | |
|---|---|---|---|---|---|---|---|---|
| 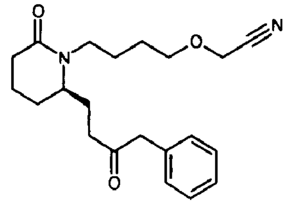 | NA | NA | NA | NA | NA | NA | NA | NA |
| 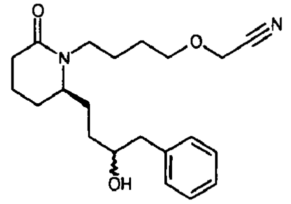 | NA | NA | NA | NA | NA | NA | NA | NA |
| 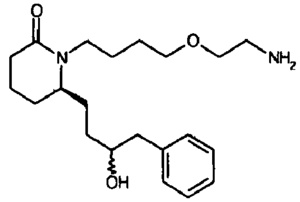 | NA | NA | NA | NA | NA | NA | NA | NA |

TREATMENT OF INFLAMMATORY BOWEL DISEASE

CROSS-REFERENCE TO RELATED APPLICATIONS

This application is a continuation-in-part of U.S. patent application Ser. No. 10/861,957, filed on Jun. 3, 2004, now U.S. Pat. No. 7,179,820 which is a continuation-in-part of U.S. patent application Ser. No. 10/456,275, filed on Jun. 6, 2003, now U.S. Pat. No. 6,747,037 incorporated herein by reference, and claims priority thereto.

U.S. patent application Ser. No. 10/861,957, filed on Jun. 3, 2004 is also a continuation-in-part of U.S. patent application Ser. No. 10/763,702, filed on Jan. 22, 2004, now U.S. Pat. No. 6,977,260 incorporated herein by reference, and claims priority thereto.

BACKGROUND OF THE INVENTION

1. Field of the Invention

The present invention relates to piperidinyl prostaglandin E analogs useful as therapeutic agents, e.g. treatment of inflammatory bowel disease.

2. Description of Related Art

Prostaglandins can be described as derivatives of prostanoic acid which have the following structural formula:

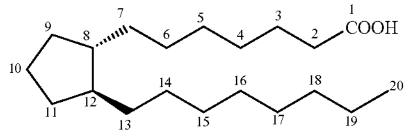

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Prostaglandins are useful for the long-term medical management of glaucoma (see, for example, Bito, L. Z. *Biological Protection with Prostaglandins*, Cohen, M. M., ed., Boca Raton, Fla., CRC Press Inc., 1985, pp. 231-252; and Bito, L. Z., *Applied Pharmacology in the Medical Treatment of Glaucomas* Drance, S. M. and Neufeld, A. H. eds., New York, Grune & Stratton, 1984, pp. 477-505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

U.S. Patent Publication 2004/0142969 A1 discloses compounds according to the formula below

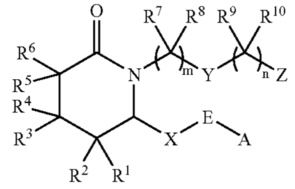

the application discloses the identity of the groups as follows.

- m is from 1 to 4; n is from 0 to 4; A is alkyl, aryl, heteroaryl, arylalkyl, arylcycloalkyl, cycloalkylalkyl, or aryloxyalkyl; E is —CHOH— or —C(O)—; X is $—(CH_2)_2—$ or —CH═CH—; Y is $—CH_2—$, arylene, heteroarylene, —CH═CH—, —O—, $—S(O)_p—$ where p is from 0 to 2, or $—NR^a—$ where $R^a$ is hydrogen or alkyl;
- Z is $—CH_2OH$, —CHO, tetrazol-5-yl, or $—COOR^b$ where $R^b$ is hydrogen or alkyl; and $R^1$, $R^2$, $R^3$, $R^4$, $R^5$, $R^6$, $R^7$, $R^8$, $R^9$ and $R^{10}$ each independently are hydrogen or alkyl.

WO2004085430 discloses similar compounds to U.S. Patent Publication 2004/0142969 A1, as well as others of interest.

Inflammatory bowel disease (IBD) is a group of disease characterized by inflammation in the large or small intestines and is manifest in symptoms such as diarrhea, pain, and weight loss. Nonsteroidal anti-inflammatory drugs have been shown to be associated with the risk of developing IBD, and recently Kabashima and colleagues have disclosed that "EP4 works to keep mucosal integrity, to suppress the innate immunity, and to downregulate the proliferation and activation of CD4+ T cells. These findings have not only elucidated the mechanisms of IBD by NSAIDs, but also indicated the therapeutic potential of EP4-selective agonists in prevention and treatment of IBD." (Kabashima, et. al., The Journal of Clinical Investigation, April 2002, Vol. 9, 883-893)

SUMMARY OF THE INVENTION

Methods are disclosed herein for the treatment of inflammatory bowel disease by administration of a therapeutically effective amount of a compound of formula I

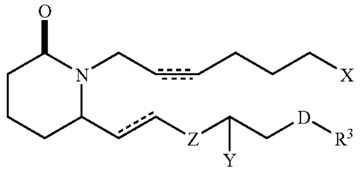

wherein hatched lines represent the a configuration, a triangle represents the β configuration, a wavy line represents either the a configuration or the β configuration and a dotted line represents the presence or absence of a double bond;

D represents a covalent bond or $CH_2$, O, S or NH;

X is $CO_2R$, $CONR_2$, $CH_2OR$, $P(O)(OR)_2$, $CONRSO_2R$, $SO_2NR_2$ or

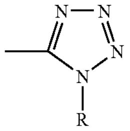 Y is 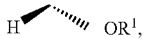, 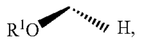,

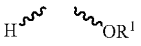 or 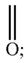;

Z is $CH_2$ or a covalent bond;

R is H or $R^2$;

$R^1$ is H, $R^2$, phenyl, or $COR^2$;

$R^2$ is $C_1$-$C_5$ lower alkyl or alkenyl and $R^3$ is selected from the group consisting of $R^2$, phenyl, thienyl, furanyl, pyridyl, benzothienyl, benzofuranyl, naphthyl, or substituted derivatives thereof, wherein the substituents maybe selected from the group consisting of $C_1$-$C_5$ alkyl, halogen, $CF_3$, CN, $NO_2$, $NR_2$, $CO_2R$ and OR.

Other useful compounds for treating inflammatory bowel disease comprise

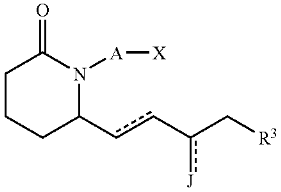

or a pharmaceutically acceptable salt or a prodrug thereof;

wherein a dotted line represents the presence or absence of a double bond;

A is $—(CH_2)_6—$, cis $—CH_2CH{=}CH—(CH_2)_3—$, or $—CH_2C{\equiv}C—(CH_2)_3—$, wherein 1 or 2 carbon atoms may be substituted with S or O;

X is $CO_2R$, $CONR_2$, $CH_2OR$, $P(O)(OR)_2$, $CONRSO_2R$ $SO_2NR_2$ or

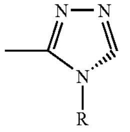

J is =O or —OH;

R is H or $R^2$;

$R^2$ is $C_1$-$C_5$ lower alkyl or alkenyl and $R^3$ is selected from the group consisting of $R^2$, phenyl, thienyl, furanyl, pyridyl, benzothienyl, benzofuranyl, naphthyl or substituted derivatives thereof, wherein the substituents maybe selected from the group consisting of $C_1$-$C_5$ alkyl, halogen, $CF_3$, CN, $NO_2$, $NR_2$, $CO_2R$ and OR.

Other useful compounds for treating inflammatory bowel disease include those having an α and an ω chain comprising

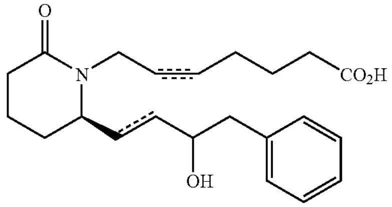

or derivatives thereof, wherein a dotted line indicates the presence or absence of a bond, a triangle represents the β configuration, and wherein said derivative has a structure as shown above except that from 1 to 2 alterations are made to the α chain and/or the ω chain, an alteration consisting of a. adding, removing, or substituting a non-hydrogen atom, b. converting an alcohol to a carbonyl, c. converting a $CO_2H$ to a moiety selected from the group consisting of $CONMe_2$, CONHMe, CONHEt, $CON(OCH_3)CH_3$, $CONH_2$, $CON(CH_2CH_2OH)_2$, $CONH(CH_2CH_2OH)$, $CH_2OH$, $P(O)(OH)_2$, $CONHSO_2CH_3$, $SO_2NH_2$, $SO_2N(CH_3)_2$, $SO_2NH(CH_3)$,

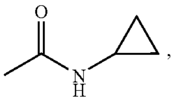, and 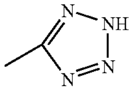, d. converting a phenyl moiety to a pyridinyl, furyl, or thienyl moiety, or e. adding a substituent comprising from 1 to 3 non-hydrogen atoms to an aromatic or a heteroaromatic ring;

or pharmaceutically acceptable salts or prodrugs thereof.

Other useful compounds for treating inflammatory bowel disease include those having an α and an ω chain comprising

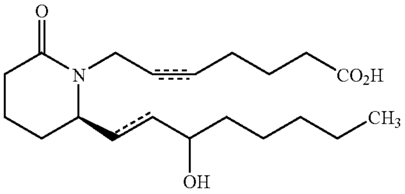

or derivatives thereof, wherein a dotted line indicates the presence or absence of a bond, a triangle represents the β configuration, and wherein said derivative has a structure as shown above except that from 1 to 2 alterations are made to the α chain and/or the ω chain, an alteration consisting of a. adding, removed, or substituting a non-hydrogen atom, b. converting an alcohol to a carbonyl, or f. converting a $CO_2H$ to a moiety selected from the group consisting of $CONMe_2$, CONHMe, CONHEt, $CON(OCH_3)CH_3$, $CONH_2$, $CON(CH_2CH_2OH)_2$, $CONH(CH_2CH_2OH)$, $CH_2OH$, $P(O)(OH)_2$, $CONHSO_2CH_3$, $SO_2NH_2$, $SO_2N(CH_3)_2$, $SO_2NH(CH_3)$,

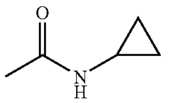, and 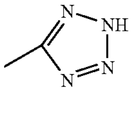, or pharmaceutically acceptable salts or prodrugs thereof.

In a still further aspect, the present invention relates to a pharmaceutical product, comprising a container adapted to dispense its contents in a metered form; and an ophthalmic solution therein, as hereinabove defined.

Finally, certain of the compounds represented by the above formulae, disclosed below and utilized in the method of the present invention are novel and unobvious.

DETAILED DESCRIPTION OF THE INVENTION

Figure 1:
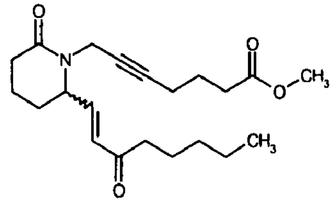
FIG. 1 is a Table showing the in vitro assay results for compounds prepared as disclosed herein.
Figure 1:
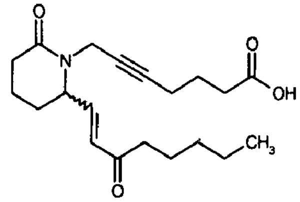
Figure 1:
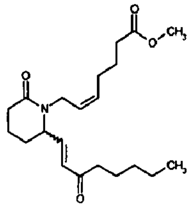

Treatment of inflammatory bowel disease may be accomplished by the administration of the compounds described herein to the suffering mammal. Inflammatory bowel disease describes a variety of diseases characterized by inflammation of the bowels including, but not limited to, ulcerative colitis and Crohn's disease. Treatment may be accomplished by oral administration, by suppository, or parenteral administration, or some other suitable method.

Certain compounds used in accordance with the present invention are encompassed by the following structural formula I:

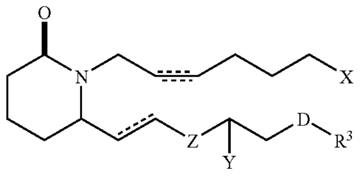

The preferred group of the compounds of the present invention includes compounds that have the following structural formula II.

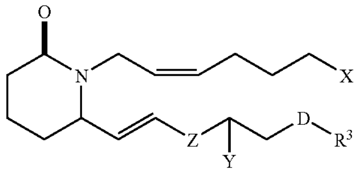

In the above formulae, the substituents and symbols are as hereinabove defined.

In the above formulae:

Preferably Y is

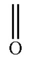 or 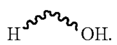

Preferably D represents a covalent bond or is $CH_2$; more preferably D is $CH_2$ and $R^3$ is n-propyl or D is a covalent bond and $R^3$ is phenyl.

Preferably Z represents a covalent bond.

Preferably R is H or $C_1$-$C_5$ lower alkyl.

Preferably $R^1$ is H.

Preferably $R^3$ is selected from the group consisting of phenyl and n-propyl.

Preferably X is $CO_2R$ and more preferably R is selected from the group consisting of H and methyl.

In relation to the identity of A disclosed in the chemical structures presented herein, in the broadest sense, A is $-(CH_2)_6-$, cis $-CH_2CH{=}CH-(CH_2)_3-$, or $-CH_2CH{\equiv}CH-(CH_2)_3-$, wherein 1 or 2 carbon atoms may be substituted with S or O. In other words, A may be $-(CH_2)_6-$, cis $-CH_2CH{=}CH-(CH_2)_3-$, $-CH_2CH{\equiv}CH-(CH_2)_3-$, or A may be a group which is related to one of these two moieties in that any carbon is substituted with S or O. For example, while not intending to limit the scope of the invention in any way, A may be an S substituted moiety such as one of the following or the like.

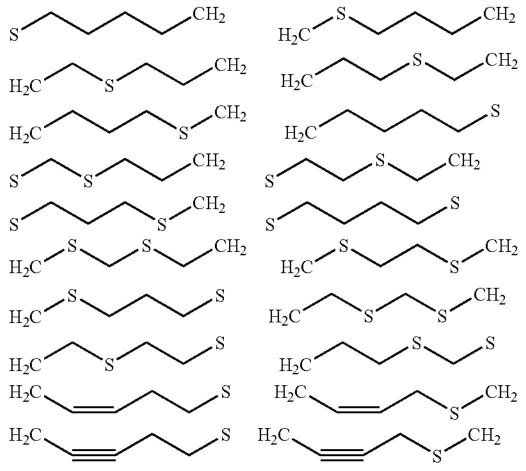

Alternatively, while not intending to limit the scope of the invention in any way, A may be an O substituted moiety such as one of the following or the like.

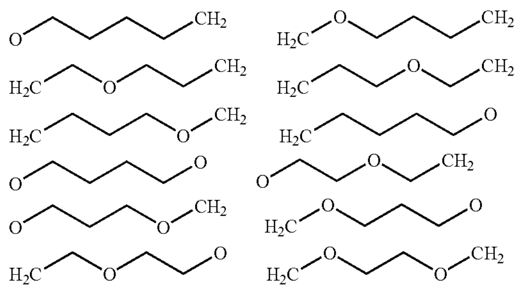

-continued

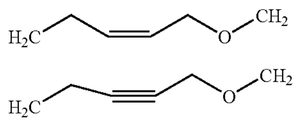

In other embodiments, A is $-(CH_2)_6-$, cis $-CH_2CH{=}CH-(CH_2)_3-$, or $-CH_2CH{\equiv}CH-(CH_2)_3-$ having no heteroatom substitution.

Some compounds comprise

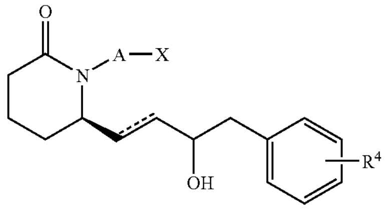

or a pharmaceutically acceptable salt or a prodrug thereof, wherein a triangle represents the β configuration, and $R^4$ is selected from the group consisting of H, $C_1$-$C_5$ alkyl, halogen, $CF_3$, CN, $NO_2$, $NR_2$, $CO_2R$ and OR.

Other compounds comprise

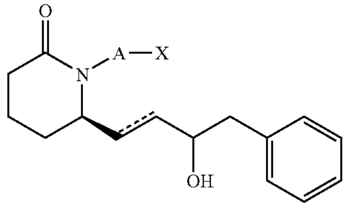

or a pharmaceutically acceptable salt or a prodrug thereof.

Other compounds comprise

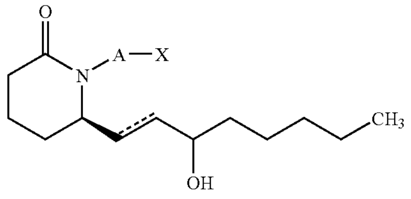

or a pharmaceutically acceptable salt or a prodrug thereof.

Other compounds comprise

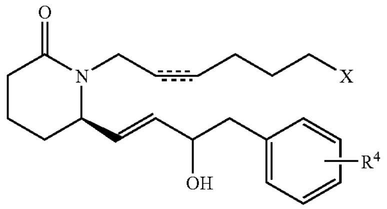

or a pharmaceutically acceptable salt or a prodrug thereof.

Other compounds comprise

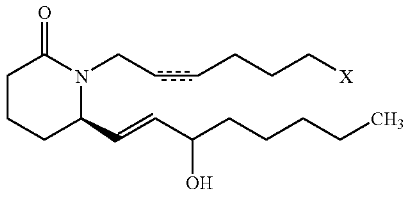

or a pharmaceutically acceptable salt or a prodrug thereof.

In all cases herein, a triangle represents the β configuration.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. While not intending to be limiting, an ester may an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

The above compounds of the present invention may be prepared by methods that are known in the art or according to the working examples below. The compounds, below, are especially preferred representative, of the compounds of the present invention.

7-[2-oxo-6-((E)-3-oxo-oct-1-enyl)-piperidin-1-yl]-hept-5-ynoic acid methyl ester 7-[2-oxo-6-((E)-3-oxo-oct-1-enyl)-piperidin-1-yl]-hept-5-ynoic acid (Z)-7-[2-oxo-6-((E)-3-oxo-oct-1-enyl)-piperidin-1-yl]-hept-5-enoic acid methyl ester (Z)-7-[2-oxo-6-((E)-3-oxo-oct-1-enyl)-piperidin-1-yl]-hept-5-enoic acid 7-[2-oxo-6-(3-oxo-octyl)-piperidin-1-yl]-heptanoic acid methyl ester 7-[2-oxo-6-(3-oxo-octyl)-piperidin-1-yl]-heptanoic acid 7-[2-(3-hydroxy-octyl)-6-oxo-piperidin-1-yl]-heptanoic acid methyl ester 7-[2-(3-hydroxy-octyl)-6-oxo-piperidin-1-yl]-heptanoic acid (Z)-7-[2-((E)-3-hydroxy-oct-1-enyl)-6-oxo-piperidin-1-yl]-hept-5-enoic acid methyl ester (Z)-7-[2-((E)-3-hydroxy-oct-1-enyl)-6-oxo-piperidin-1-yl]-hept-5-enoic acid 7-[2-oxo-6-((E)-3-oxo-oct-1-enyl)-piperidin-1-yl]-heptanoic acid methyl ester 7-[2-oxo-6-((E)-3-oxo-oct-1-enyl)-piperidin-1-yl]-heptanoic acid 7-[2-((E)-3-hydroxy-oct-1-enyl)-6-oxo-piperidin-1-yl]-heptanoic acid methyl ester 7-[2-((E)-3-hydroxy-oct-1-enyl)-6-oxo-piperidin-1-yl]-heptanoic acid 7-[2-oxo-6-((E)-3-oxo-4-phenyl-but-1-enyl)-piperidin-1-yl]-heptanoic acid methyl ester 7-[2-oxo-6-((E)-3-oxo-4-phenyl-but-1-enyl)-piperidin-1-yl]-heptanoic acid 7-[2-((E)-3-hydroxy-4-phenyl-but-1-enyl)-6-oxo-piperidin-1-yl]-heptanoic acid methyl ester 7-[2-((E)-3-hydroxy-4-phenyl-but-1-enyl)-6-oxo-piperidin-1-yl]-heptanoic acid 7-[2-(3-hydroxy-4-phenyl-butyl)-6-oxo-piperidin-1-yl]-heptanoic acid methyl ester 7-[2-(3-hydroxy-4-phenyl-butyl)-6-oxo-piperidin-1-yl]-heptanoic acid 7-[2-oxo-6-(3-oxo-4-phenyl-butyl)-piperidin-1-yl]-heptanoic acid methyl ester 7-[2-oxo-6-(3-oxo-4-phenyl-butyl)-piperidin-1-yl]-heptanoic acid 7-[2-oxo-6-((E)-3-oxo-4-phenyl-but-1-enyl)-piperidin-1-yl]-hept-5-ynoic acid methyl ester 7-[2-oxo-6-((E)-3-oxo-4-phenyl-but-1-enyl)-piperidin-1-yl]-hept-5-ynoic acid (Z)-7-[2-oxo-6-((E)-3-oxo-4-phenyl-but-1-enyl)-piperidin-1-yl]-hept-5-enoic acid methyl ester (Z)-7-[2-oxo-6-((E)-3-oxo-4-phenyl-but-1-enyl)-piperidin-1-yl]-hept-5-enoic acid (Z)-7-[2-((E)-3-hydroxy-4-phenyl-but-1-enyl)-6-oxo-piperidin-1-yl]-hept-5-enoic acid methyl ester (Z)-7-[2-((E)-3-hydroxy-4-phenyl-but-1-enyl)-6-oxo-piperidin-1-yl]-hept-5-enoic acid 7-[(R)-2-((E)-3-Hydroxy-4-phenyl-but-1-enyl)-6-oxo-piperidin-1-yl]-heptanoic acid methyl ester 7-[(R)-2-((E)-3-Hydroxy-4-phenyl-but-1-enyl)-6-oxo-piperidin-1-yl]-heptanoic acid 7-[(R)-2-((E)-3-Hydroxy-oct-1-enyl)-6-oxo-piperidin-1-yl]-heptanoic acid methyl ester 7-[(R)-2-((E)-3-Hydroxy-oct-1-enyl)-6-oxo-piperidin-1-yl]-heptanoic acid 7-[(R)-2-(3-Hydroxy-octyl)-6-oxo-piperidin-1-yl]-heptanoic acid methyl ester 7-[(R)-2-(3-Hydroxy-octyl)-6-oxo-piperidin-1-yl]-heptanoic acid 7-[(R)-2-((E)-3-Hydroxy-oct-1-enyl)-6-oxo-piperidin-1-yl]-hept-5-ynoic acid methyl ester (R)-1-(7-hydroxy-hept-2-ynyl)-6-((E)-3-hydroxy-oct-1-enyl)-piperidin-2-one (Z)-7-[(R)-2-((E)-3-Hydroxy-oct-1-enyl)-6-oxo-piperidin-1-yl]-hept-5-enoic acid methyl ester (Z)-7-[(R)-2-((E)-3-Hydroxy-oct-1-enyl)-6-oxo-piperidin-1-yl]-hept-5-enoic acid (Z)-7-[(R)-2-((E)-3-Hydroxy-4-phenyl-but-1-enyl)-6-oxo-piperidin-1-yl]-hept-5-enoic acid methyl ester (Z)-7-[(R)-2-((E)-3-Hydroxy-4-phenyl-but-1-enyl)-6-oxo-piperidin-1-yl]-hept-5-enoic acid 7-[(R)-2-((E)-3-Hydroxy-4-phenyl-but-1-enyl)-6-oxo-piperidin-1-yl]-hept-5-ynoic acid methyl ester 7-[(R)-2-((E)-3-Hydroxy-4-phenyl-but-1-enyl)-6-oxo-piperidin-1-yl]-hept-5-ynoic acid 7-[(R)-2-((E)-3-Hydroxy-4-phenyl-but-1-enyl)-6-oxo-piperidin-1-yl]-heptanoic acid isopropyl ester 7-[(R)-2-((E)-3-Hydroxy-4-phenyl-but-1-enyl)-6-oxo-piperidin-1-yl]-heptanoic acid amide 7-[(R)-2-((E)-3-Hydroxy-4-phenyl-but-1-enyl)-6-oxo-piperidin-1-yl]-heptanoic acid isopropyl ester (faster eluting diastereomer by HPLC)

7-[(R)-2-((E)-3-Hydroxy-4-phenyl-but-1-enyl)-6-oxo-piperidin-1-yl]-heptanoic acid isopropyl ester (slower eluting diastereomer by HPLC).

One embodiment comprises derivatives of

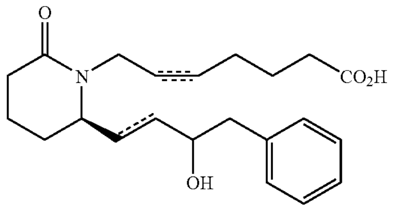

or a derivative thereof, wherein a dotted line indicates the presence or absence of a bond, and wherein said derivative has a structure as shown above except that from 1 to 2 alterations are made to the α chain and/or the ω chain, an alteration consisting of a. adding, removing, or substituting a non-hydrogen atom, b. converting an alcohol to a carbonyl, g. converting a $CO_2H$ to a moiety selected from the group consisting of $CONMe_2$, CONHMe, CONHEt, $CON(OCH_3)CH_3$, $CONH_2$, $CON(CH_2CH_2OH)_2$, $CONH(CH_2CH_2OH)$, $CH_2OH$, $P(O)(OH)_2$, $CONHSO_2CH_3$, $SO_2NH_2$, $SO_2N(CH_3)_2$, $SO_2NH(CH_3)$,

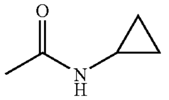
, and
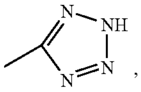
, c. converting a phenyl moiety to a pyridinyl, furyl, or thienyl moiety, or d. adding a substituent comprising from 1 to 3 non-hydrogen atoms to an aromatic or a heteroaromatic ring;

Another embodiment comprises derivatives of

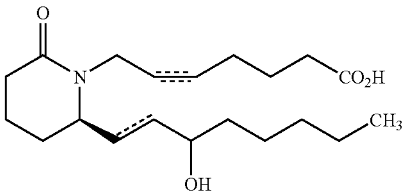

or a derivative thereof, wherein a dotted line indicates the presence or absence of a bond, and wherein said derivative has a structure as shown above except that from 1 to 2 alterations are made to the α chain and/or the ω chain, an alteration consisting of a. adding, removed, or substituting a non-hydrogen atom, b. converting an alcohol to a carbonyl, or h. converting a $CO_2H$ to a moiety selected from the group consisting of $CONMe_2$, CONHMe, CONHEt, $CON(OCH_3)CH_3$, $CONH_2$, $CON(CH_2CH_2OH)_2$, $CONH(CH_2CH_2OH)$, $CH_2OH$, $P(O)(OH)_2$, $CONHSO_2CH_3$, $SO_2NH_2$, $SO_2N(CH_3)_2$, $SO_2NH(CH_3)$,

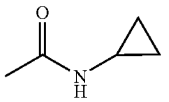
, and
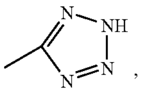
, or a pharmaceutically acceptable salt or a prodrug thereof.

The actual compounds depicted in these structures as well as their derivatives as defined herein are contemplated in these embodiments.

Thus, the following compounds are contemplated, as well as their derivatives, which will be described in detail hereafter.

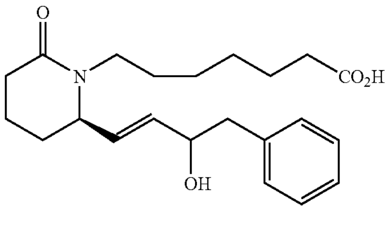

-continued

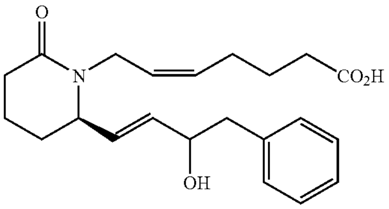

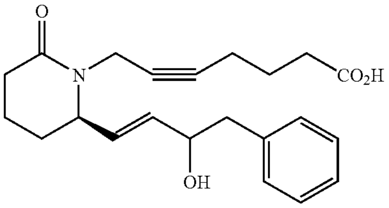

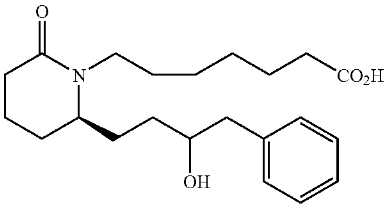

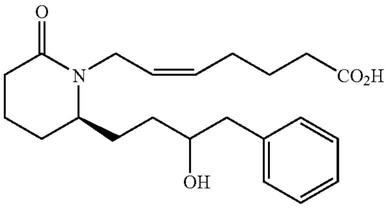

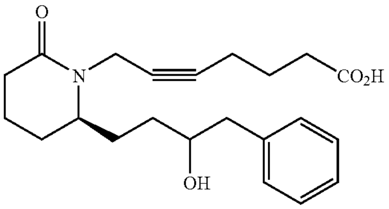

Salts, and prodrugs of the compounds depicted in the structures as well as salts and prodrugs of the derivatives are also contemplated.

The following compounds are also contemplated, as well as their derivatives, which will be described in detail hereafter.

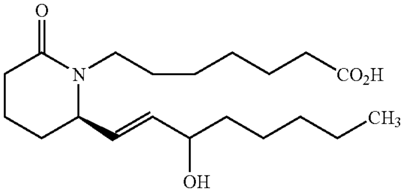

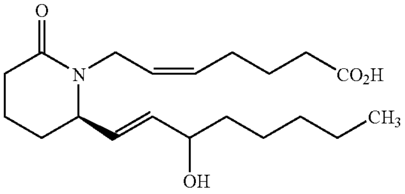

-continued

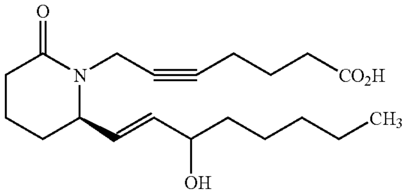

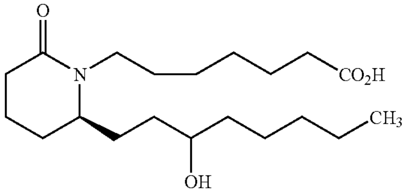

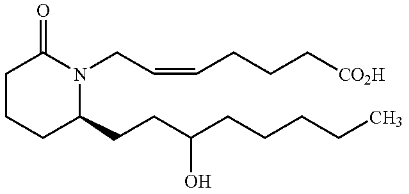

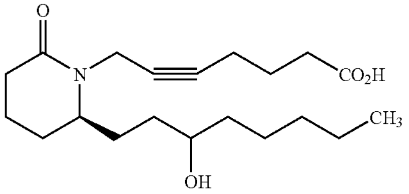

Salts, and prodrugs of the compounds depicted in the structures as well as salts and prodrugs of the derivatives are also contemplated.

In making reference to a derivative and alterations to the structure shown above, it should be emphasized that making alterations and forming derivatives is strictly a mental exercise used to define a set of chemical compounds, and has nothing to do with whether said alteration can actually be carried out in the laboratory, or whether a derivative can be prepared by an alteration described. However, whether the derivative can be prepared via any designated alteration or not, the differences between the derivatives and the aforementioned structure are such that a person of ordinary skill in the art could prepare the derivatives disclosed herein using routine methods known in the art without undue experimentation.

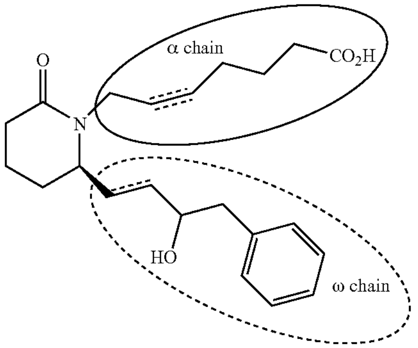

-continued

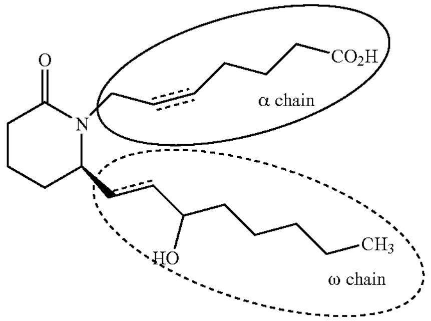

The α chain is the group in the solid circle in the labeled structures above. The ω chain is the group in the dashed circle in the labeled structures above. Thus, in these embodiments said derivative may be different from the formulae above at the α chain, while no alteration is made to the ω chain, as for example, in the structures shown below.

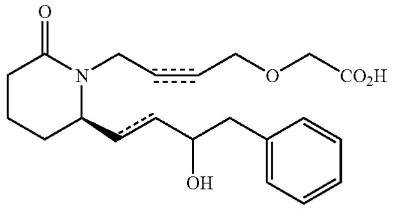

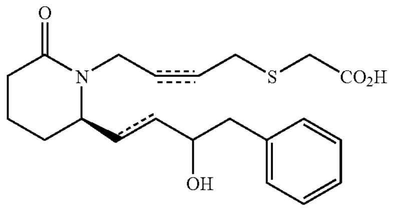

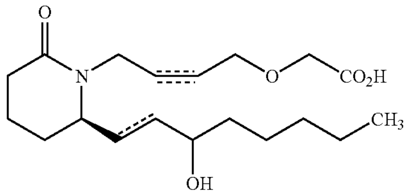

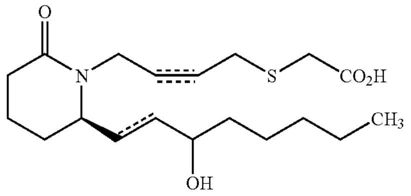

Pharmaceutically acceptable salts and prodrugs of these compounds are also contemplated.

The derivatives may also be different from the formulae above in the ω chain, while no alteration is made to the α chain, as shown in the examples below.

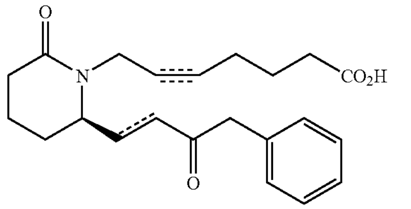

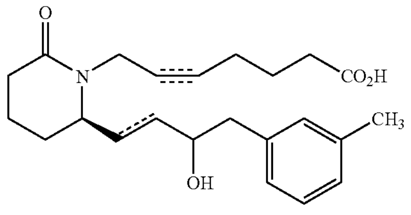

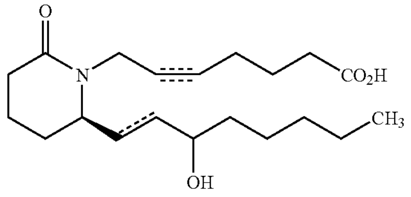

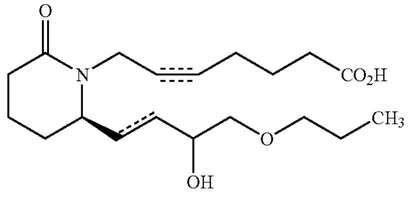

Pharmaceutically acceptable salts and prodrugs of these compounds are also contemplated.

Alternatively, the derivatives may be different in both the α and ω chains, as shown in the examples below.

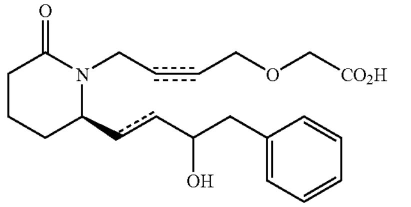

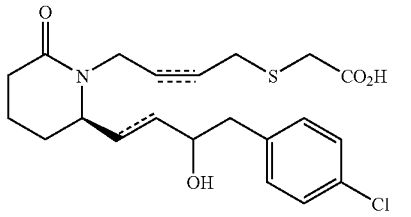

-continued

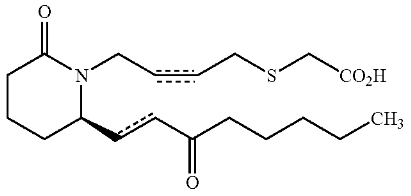

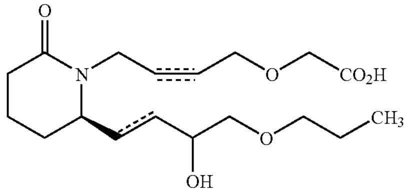

Pharmaceutically acceptable salts and prodrugs of these compounds are also contemplated.

Changes to the structure can take several forms, if a non-hydrogen atom is added, the structure is changed by adding the atom, and any required hydrogen atoms, but leaving the remaining non-hydrogen atoms unchanged, such as in the examples shown below, with the added atoms in bold type.

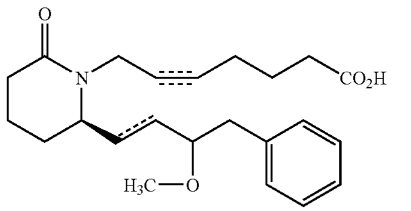

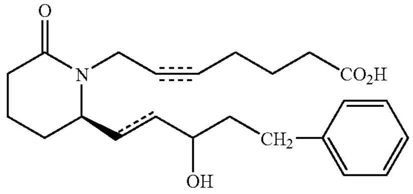

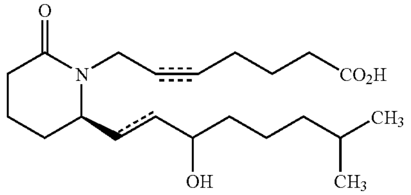

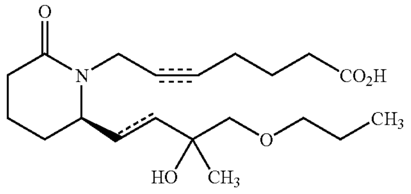

Pharmaceutically acceptable salts and prodrugs of these compounds are also contemplated.

While adding a methyl group or a methylene group to the molecule is a useful alteration in many situations, it may also be useful to add other non-hydrogen atoms such as sulfur or oxygen, such as in the examples below.

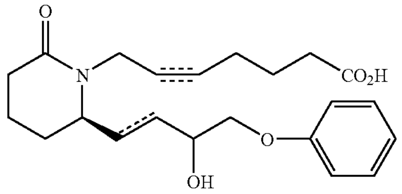

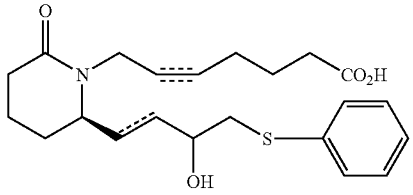

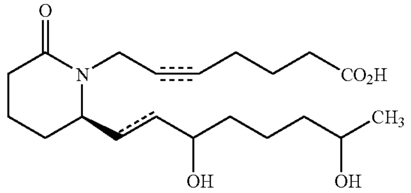

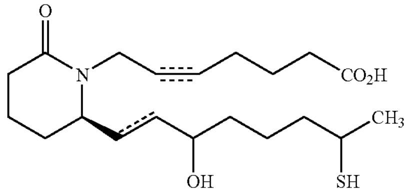

Pharmaceutically acceptable salts and prodrugs of these compounds are also contemplated.

If a non-hydrogen atom is removed, the structure is changed by removing the atom, and any required hydrogen atoms, but leaving the remaining non-hydrogen atoms unchanged, such as in the examples shown below, with the previous location of the missing atoms indicated by arrows.

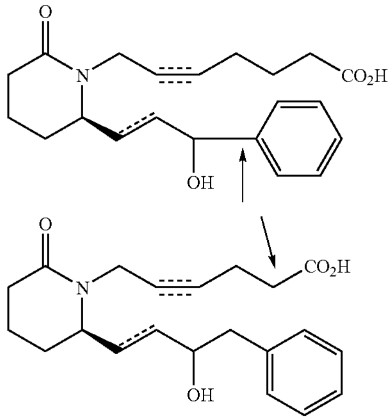

Pharmaceutically acceptable salts and prodrugs of these compounds are also contemplated.

If a non-hydrogen atom is substituted, the non-hydrogen atom is replaced by a different non-hydrogen atom, with any necessary adjustment made to the number hydrogen atoms, such as in the examples shown below, with the substituted atoms in bold type.

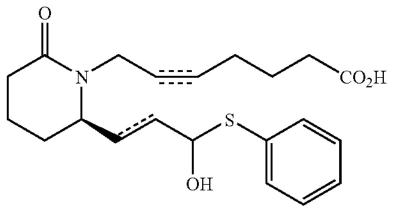

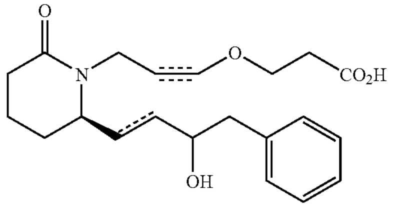

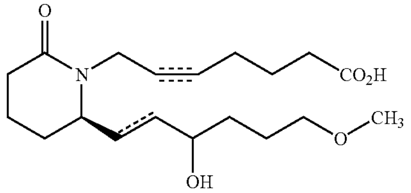

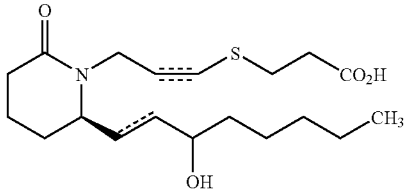

Pharmaceutically acceptable salts and prodrugs of these compounds are also contemplated.

Another possible alteration is the conversion of an alcohol to a carbonyl, such as in the examples below.

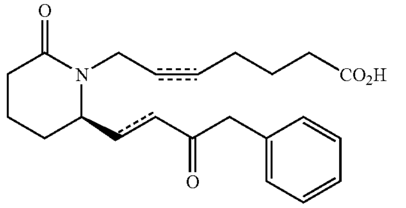

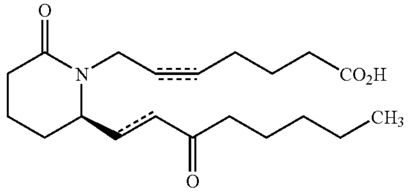

Pharmaceutically acceptable salts and prodrugs of these compounds are also contemplated.

Another alteration includes converting a $CO_2H$ to a moiety selected from the group consisting of $CONMe_2$, CONHMe, CONHEt, $CON(OCH_3)CH_3$, $CONH_2$, $CON(CH_2CH_2OH)_2$, $CONH(CH_2CH_2OH)$, $CH_2OH$, $P(O)(OH)_2$, $CONHSO_2CH_3$, $SO_2NH_2$, $SO_2N(CH_3)_2$, $SO_2NH(CH_3)$,

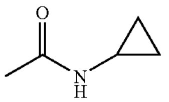, and 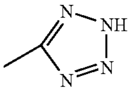,
such as in the examples below.
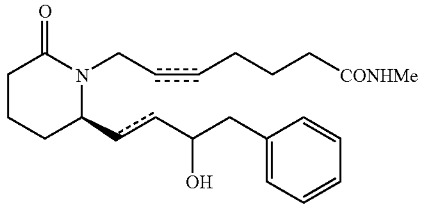
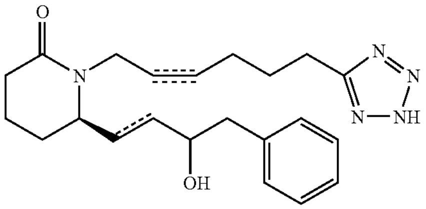
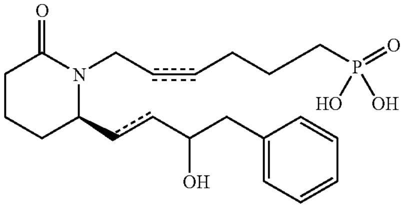
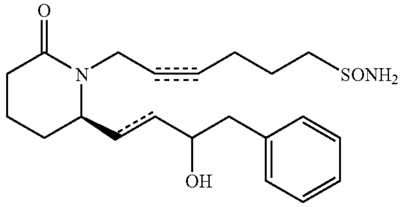
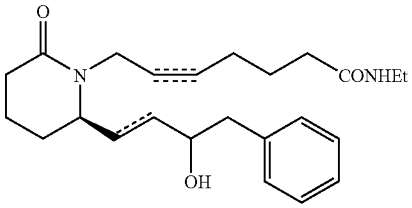
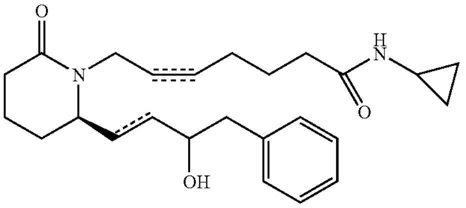
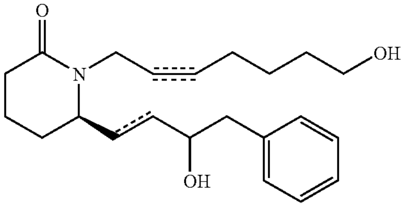
-continued
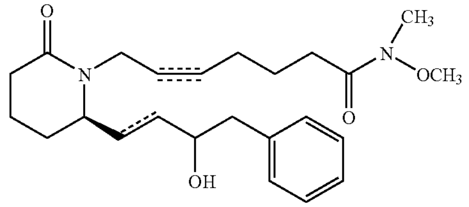
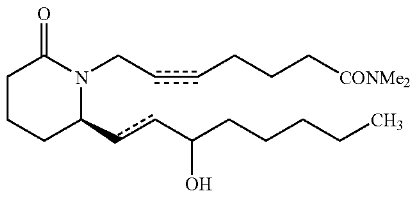
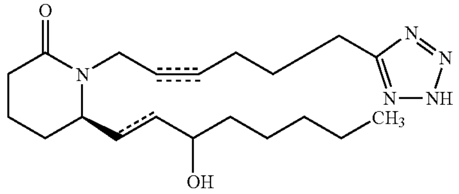
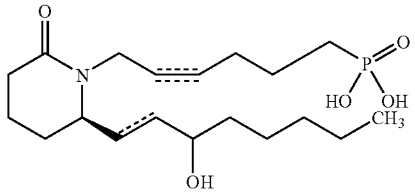
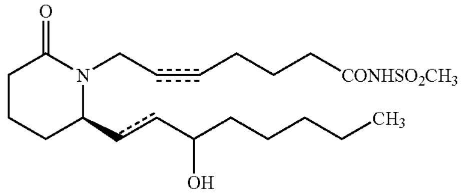
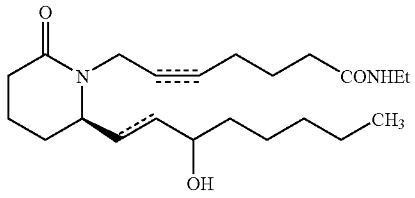
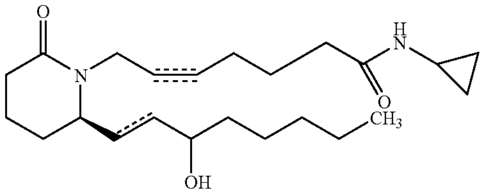
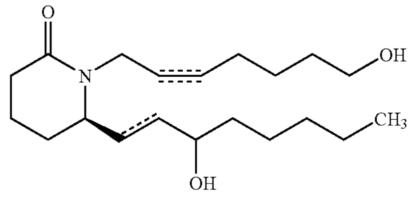

-continued

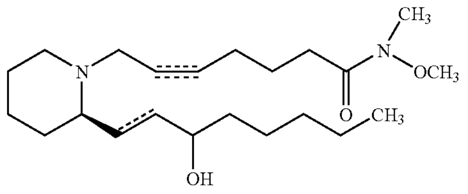

Pharmaceutically acceptable salts and prodrugs of these compounds are also contemplated.

The tetrazole group,

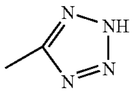

has two tautomeric forms, which can rapidly interconvert in aqueous or biological media, and are thus equivalent to one another. The tautomer of the tetrazole shown above is shown below.

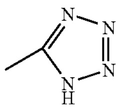

For the purposes disclosed herein, all tautomeric forms should be considered equivalent in every way. If the tetrazole has a substituent or some other symmetry breaking feature, more than two tautomeric forms may exist. These are also considered to be equivalent to one another.

Another alteration consists of converting a phenyl moiety to a pyridinyl, furyl, or thienyl moiety, such as in the examples below.

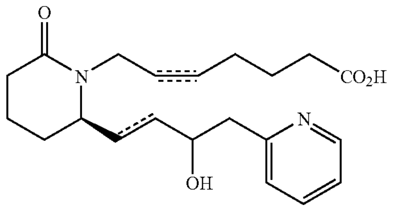

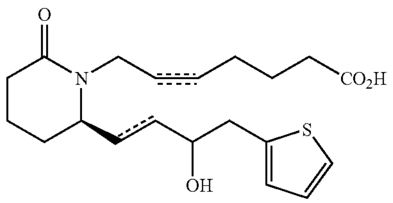

-continued

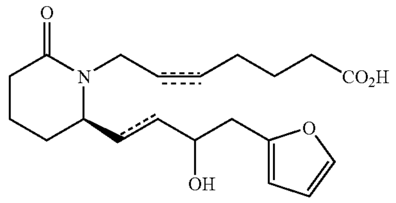

Pharmaceutically acceptable salts and prodrugs of these compounds are also contemplated.

Another alteration consists of adding a substituent comprising from 1 to 3 non-hydrogen atoms to an aromatic or a heteroaromatic ring, as in the examples below.

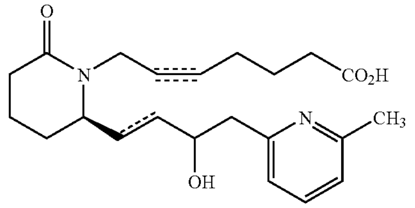

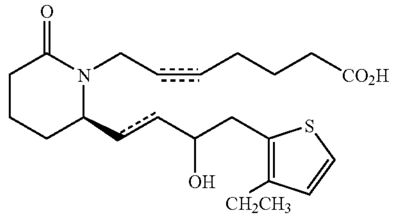

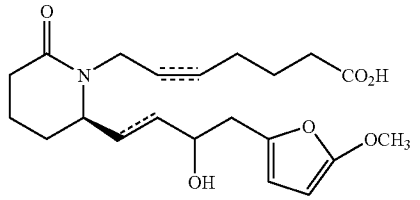

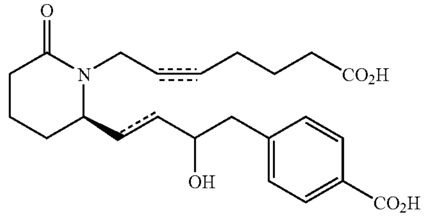

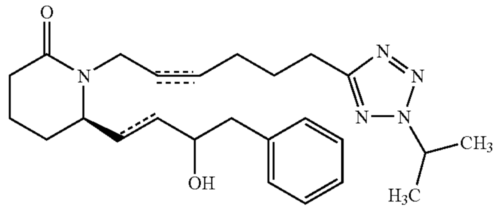

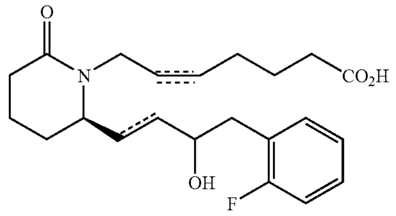

-continued

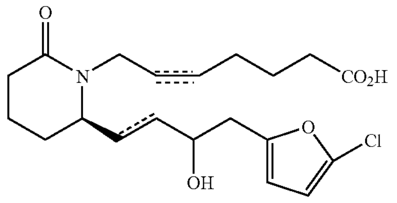

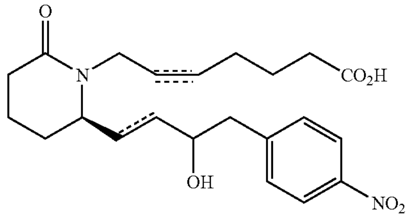

Pharmaceutically acceptable salts and prodrugs of these compounds are also contemplated.

If a derivative could reasonably be construed to consist of a different number of alterations, the derivative is considered to have the lowest reasonable number of alterations. For example, the compound shown below, having the modified portion of the molecule in bold, could be reasonably construed to have 1 or 2 alterations relative to the defined structure.

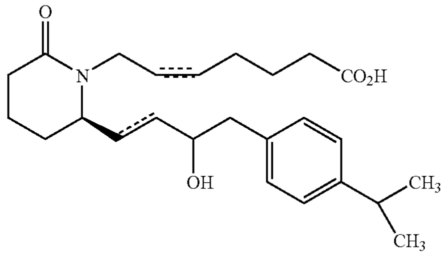

By one line of reasoning, the first alteration would be to add an ethyl substituent to the phenyl ring. The second alteration would be to add a carbon atom, with its accompanying hydrogen atoms to the ethyl substituent. By a second line of reasoning, the derivative would be obtained by simply adding an isopropyl group to the phenyl ring. In accordance with the rule established above, the compound above is defined as having 1 alteration. Thus, an additional alteration could be made to the structure to obtain the compounds such as the examples shown below.

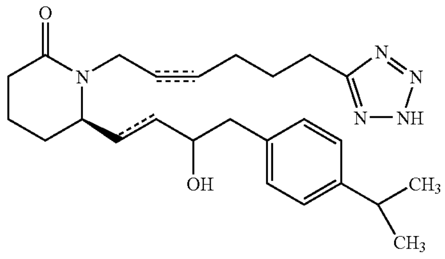

-continued

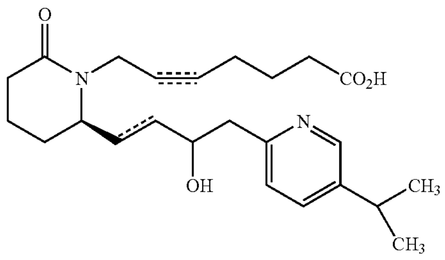

Pharmaceutically acceptable salts and prodrugs of these compounds are also contemplated.

Some alterations are considered to render particularly useful compounds. While not intending to limit the scope of the invention in any way, in certain compounds, an oxygen atom or a sulfur atom is substituted for a carbon atom, such as in the examples below. In particular, it is useful for this alteration to occur in the α chain, as in the case in 5 of the 6 examples shown below.

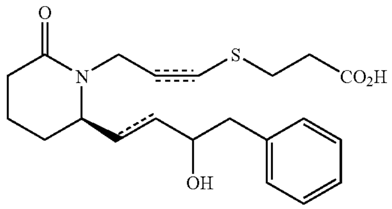

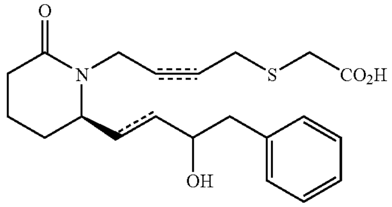

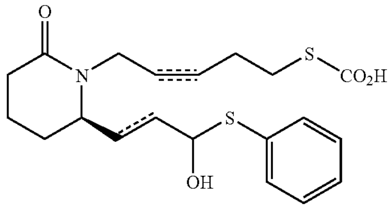

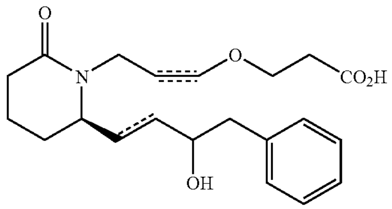

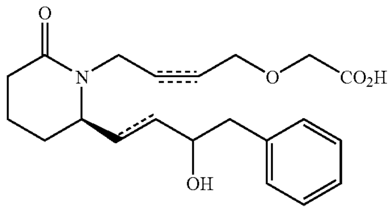

-continued

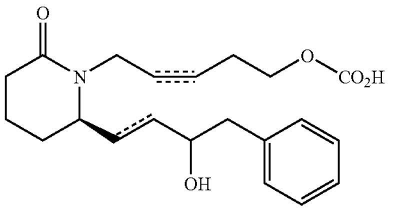

Pharmaceutically acceptable salts and prodrugs of these compounds are also contemplated.

The addition of $CH_2$, O, or S to the ω chain is also considered to yield particular useful compounds such as the ones below.

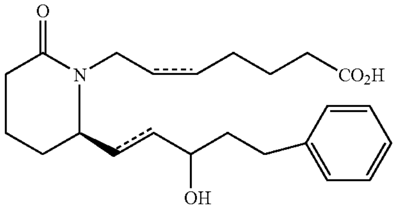

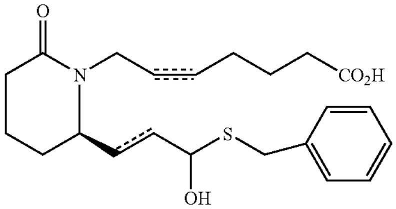

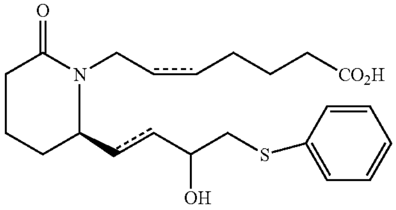

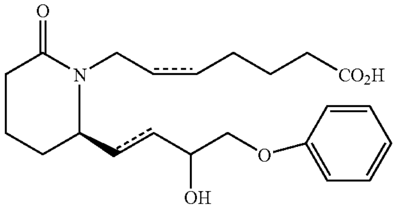

Pharmaceutically acceptable salts and prodrugs of these compounds are also contemplated.

While not intending to limit the scope of the invention in any way, particularly useful compounds are obtained when certain alterations are made twice. Alterations that are useful when made twice are the substitution of a carbon atom with a sulfur atom or an oxygen atom and the addition of a substituent to a phenyl ring.

Examples of compounds obtained by two substitutions of a carbon atom with a sulfur atom or an oxygen atom are shown below.

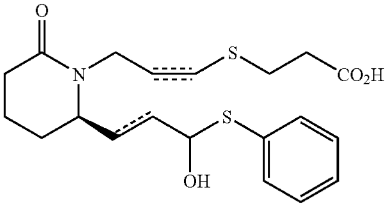

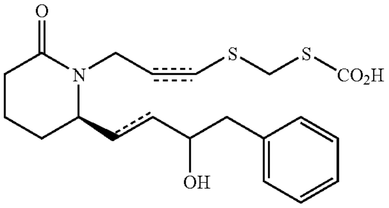

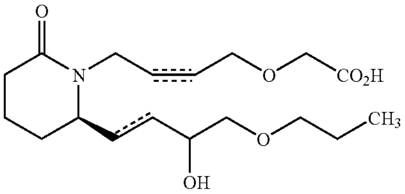

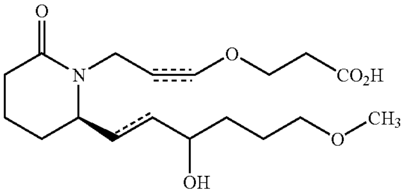

Pharmaceutically acceptable salts and prodrugs of these compounds are also contemplated.

Examples of compound obtained by two additions of a substituent to a phenyl ring are shown below.

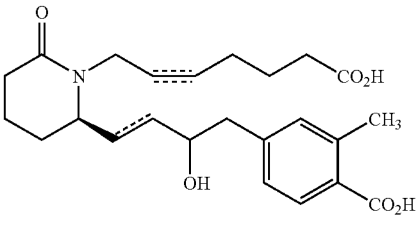

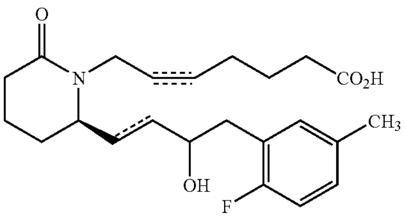

-continued

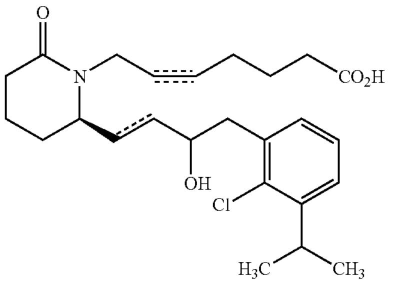

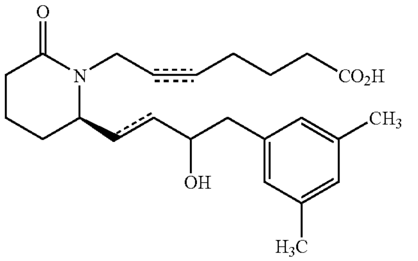

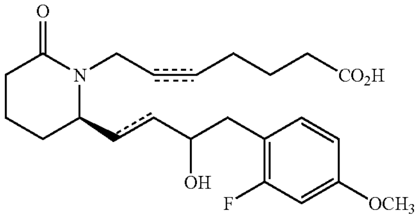

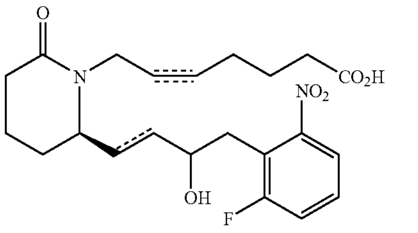

Pharmaceutically acceptable salts and prodrugs of these compounds are also contemplated.

While not intending to limit the scope of the invention in any way, certain combinations of alterations also render particularly useful compounds. In particular, the combination of substitution of carbon with sulfur or oxygen with an alteration to the phenyl ring gives particularly useful compounds. For example, substitution of a carbon atom with sulfur or oxygen and the addition of a substituent to a phenyl ring yields particularly useful compounds such as the ones shown below.

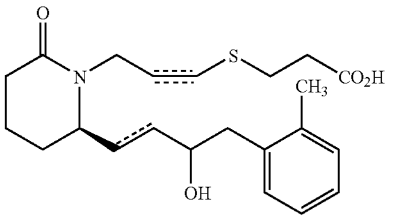

-continued

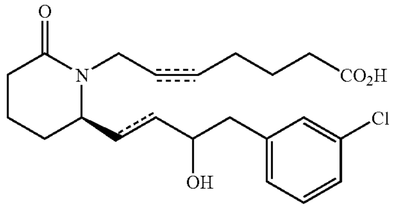

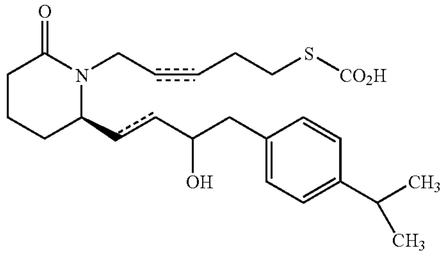

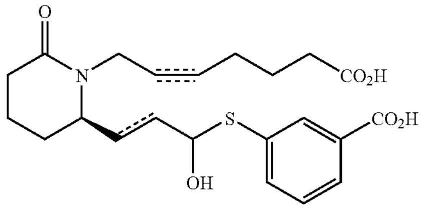

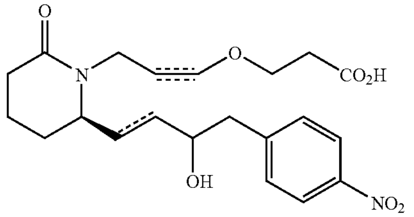

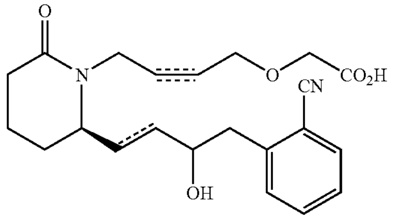

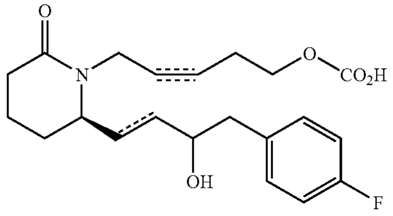

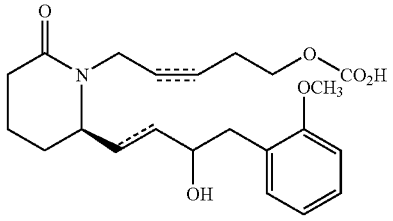

Pharmaceutically acceptable salts and prodrugs of these compounds are also contemplated.

Another combination which yields useful compounds is the substitution of phenyl with pyridinyl, furyl, or thienyl and the substitution of a carbon atom with sulfur or oxygen such as in the examples below.

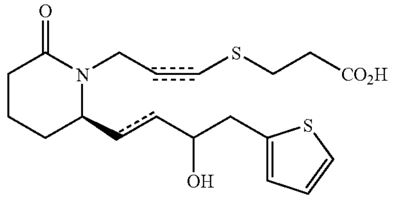

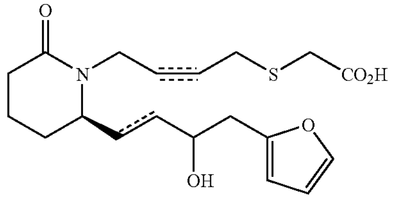

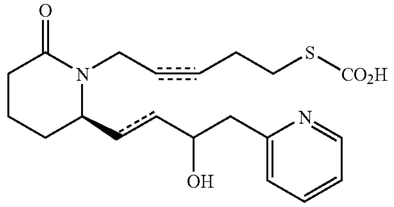

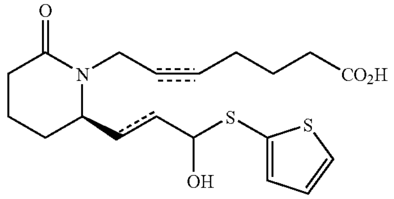

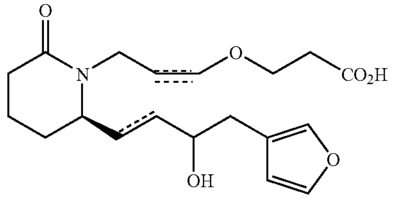

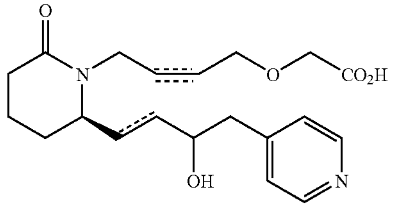

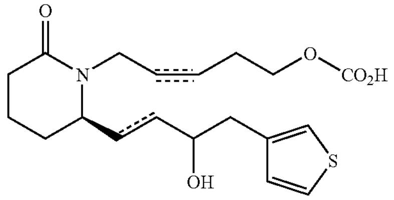

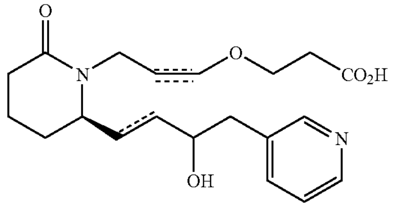

Pharmaceutically acceptable salts and prodrugs of these compounds are also contemplated.

Another combination which yields useful compounds is the substitution of phenyl with pyridinyl, furyl, or thienyl and the addition of a substituent to the heteroaryl ring such as in the examples below.

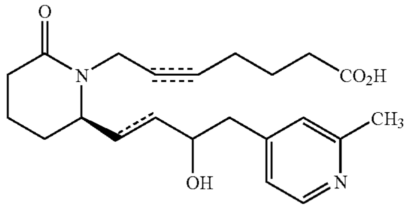

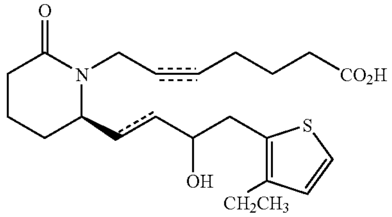

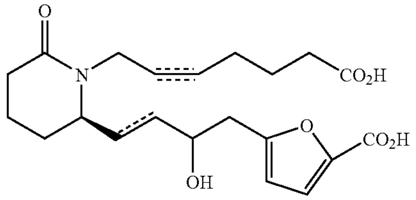

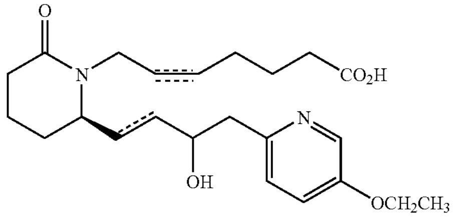

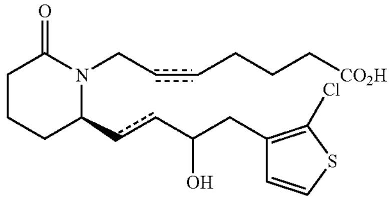

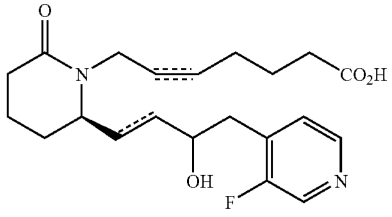

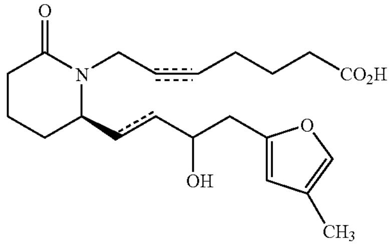

-continued

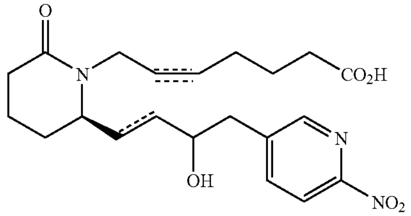

Pharmaceutically acceptable salts and prodrugs of these compounds are also contemplated.

Treatment of inflammatory bowel disease may be accomplished by the administration of the compounds described herein to the suffering mammal. Inflammatory bowel disease describes a variety of diseases characterized by inflammation of the bowels including, but not limited to, ulcerative colitis and Crohn's disease. Treatment may be accomplished by oral administration, by suppository, or parenteral administration, or some other suitable method.

While not intending to limit the scope of the invention in any way, delivery of the compounds disclosed herein to the colon via oral dosage forms may be accomplished by any of a number of methods known in the art. For example, reviews by Chourasia and Jain in J Pharm Pharmaceut Sci 6 (1): 33-66, 2003 and Shareef et. al (AAPS Pharm Sci 2003; 5 (2) Article 17) describe a number of useful methods. While not intending to limit the scope of the invention in any way these methods include 1) administration of a prodrug, including an azo or a carbohydrate based prodrug; 2) coating the drug with, or encapsulating or impregnating the drug into a polymer designed for delivery to the colon, 3) time released delivery of the drug, 4) use of a bioadhesive system; and the like.

While not intending to be bound in any way by theory, it is believed that intestinal microflora are capable of reductive cleavage of an azo bond leaving the two nitrogen atoms as amine functional groups. While not intending to limit the scope of the invention in any way, the azo prodrug approach has been used to deliver to 5-aminosalicylic acid humans in clinical trials for the treatment of irritable bowel disease. It is also believed that bacteria of the lower GI also have enzymes which can digest glycosides, glucuronides, cyclodextrins, dextrans, and other carbohydrates, and ester prodrugs formed from these carbohydrates have been shown to deliver the parent active drugs selectively to the colon. For example, in vivo and in vitro studies on rats and guinea pigs with prodrugs of dexamethasone, prednisolone, hydrocortisone, and fludrocortisone, suggest that glycoside conjugates may be useful for the delivery of steroids to the human colon. Other in vivo studies have suggested that glucouronide, cyclodextrin, and dextran prodrugs of steroids or non-steroidal anti-inflammatory drugs are useful for delivery of these drugs to the lower GI tract. An amide of salicylic acid and glutamic acid has been shown to be useful for the delivery of salicylic acid to the colon of rabbit and dog.

While not intending to limit the scope of the invention in any way, carbohydrate polymers such as amylase, arabinogalactan, chitosan, chondroiton sulfate, dextran, guar gum, pectin, xylin, and the like, or azo-group containing polymers can be used to coat a drug compound, or a drug may be impregnated or encapsulated in the polymer. It is believed that after oral administration, the polymers remain stable in the upper GI tract, but are digested by the microflora of the lower GI thus releasing the drug for treatment.

Polymers which are sensitive to pH may also be used since the colon has a higher pH than the upper GI tract. Such polymers are commercially available. For example, Rohm Pharmaceuticals, Darmstadt, Germany, markets pH dependent methacrylate based polymers and copolymers which have varying solubilities over different pH ranges based upon the number of free carboxylate groups in the polymer under the tradename Eudragit®. Several Eudragit® dosage forms are currently used to deliver salsalazine for the treatment of ulcerative colitis and Crohn's disease. Time release systems, bioadhesive systems, and other delivery systems have also been studied.

In addition to excipients and methods used specifically for delivering the drug to the upper GI tract, other carriers or excipients may be used. For solid dosage forms or medicaments, other non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. Actual methods of preparing dosage forms or medicaments are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

The actual dose of the active compounds of the present invention depends on the specific compound, and on the condition to be treated; the selection of the appropriate dose is well within the knowledge of the skilled artisan.

This invention is further illustrated by the following non-limiting Examples.

EXAMPLE 1

7-[2-Oxo-6-((E)-3-oxo-oct-1-enyl)-piperidin-1-yl]-hept-5-ynoic acid methyl ester

Step 1. 6-(tert-Butyl-dimethyl-silanyloxymethyl)-piperidin-2-one

Imidazole (1.16 g, 17.0 mmol) and tert-butyldimethylsilyl chloride (1.18 g, 7.85 mmol) were added sequentially to a solution of racemic 6-hydroxymethyl-piperidin-2-one (prepared from racemic α-aminoadipic acid according to Huang, et al., *Synth. Commun.* 1989, 19, 3485-3496, 921 mg, 7.14 mmol) in DMF (10 mL) at 0° C. The reaction mixture was allowed to warm to rt and was stirred at rt for 17 h. Benzene and EtOAc (3:7, 200 mL) was added and the solution was washed with brine (3×50 mL). The organic phase was dried ($Na_2SO_4$), filtered and concentrated in vacuo. Purification of the residue by flash column chromatography on silica gel ($CH_2Cl_2$→3% MeOH/$CH_2Cl_2$, gradient) afforded 1.53 g (88%) of 6-(tert-butyl-dimethyl-silanyloxymethyl)-piperidin-2-one as a white solid.

Step 2. 7-[2-tert-Butyl-dimethyl-silanyloxymethyl)-6-oxo-piperidin-1-yl]-hept-5-ynoic acid methyl ester Sodium hydride (60% dispersion in oil, 219 mg, 5.27 mmol) was added to a solution of 6-(tert-butyl-dimethyl-silanyloxymethyl)-piperidin-2-one (1.27 g, 5.21 mmol) in DMF (10 mL) at rt. After 1 h, methyl 7-iodohept-5-ynoate (1.52 g, 5.73 mmol) in DMF (2 mL) was added via cannula. After 18 h at rt, the reaction was quenched by the addition of aqueous HCl (0.5 M, 15 mL) and the mixture was extracted with EtOAc (3×30 mL). The combined organic phase was washed with brine (3×20 mL), dried ($Na_2SO_4$), filtered and concentrated in vacuo. Purification of the residue by flash column chromatography on silica gel ($CH_2Cl_2$→40% EtOAc/$CH_2Cl_2$, gradient) afforded 1.04 g (53%) of 7-[2-tert-butyl-dimethyl-silanyloxymethyl)-6-oxo-piperidin-1-yl]-hept-5-ynoic acid methyl ester.

Step 3. 7-(2-Hydroxymethyl-6-oxo-piperidin-1-yl)-hept-5-ynoic acid methyl ester

Hydrogen fluoride-pyridine (2.5 mL) was added to a solution of 7-[2-tert-Butyl-dimethyl-silanyloxymethyl)-6-oxo-piperidin-1-yl]-hept-5-ynoic acid methyl ester (1.07 g, 2.80 mmol) in acetonitrile (5.0 mL) in a plastic scintillation vial. After 3.5 h at rt, the reaction was quenched with saturated aqueous $NaHCO_3$ (70 mL) and the mixture was extracted with EtOAc (3×50 mL). The combined organic phase was washed with brine (50 mL), dried ($Na_2SO_4$), filtered and concentrated in vacuo. Purification of the residue by flash column chromatography on silica gel ($CH_2Cl_2$→3% MeOH/$CH_2Cl_2$, gradient) afforded 724 mg (97%) of 7-(2-hydroxymethyl-6-oxo-piperidin-1-yl)-hept-5-ynoic acid methyl ester.

Step 4. 7-(2-Formyl-6-oxo-piperidin-1-yl)-hept-5-ynoic acid methyl ester 1-(3-(Dimethylaminopropyl)-3-ethylcarbodiimide hydrochloride (EDCI, 530 mg, 2.76 mmol) and DMSO (0.26 mL, 3.68 mmol) were added sequentially to a solution of 7-(2-hydroxymethyl-6-oxo-piperidin-1-yl)-hept-5-ynoic acid methyl ester (246 mg, 0.92 mmol) in benzene (7.0 mL) at rt. The mixture was cooled to 0° C. and pyridinium trifluoroacetate (196 mg, 1.01 mmol) was added. The reaction was allowed to warm to rt and then was stirred at rt for 2.5 h. The solution was decanted from the oily residue and the residue was washed with benzene (3×5 mL). The combined benzene phases were concentrated in vacuo to afford crude 7-(2-formyl-6-oxo-piperidin-1-yl)-hept-5-ynoic acid methyl ester that was used without further purification.

Step 5. 7-[2-Oxo-6-((E)-3-oxo-oct-1-enyl)-piperidin-1-yl]-hept-5-ynoic acid methyl ester Sodium hydride (60% dispersion in oil, 37 mg, 0.91 mmol) was added to a solution of dimethyl 2-oxoheptylphosphonate (217 mg, 0.83 mmol) in THF (4 mL) at 0° C. After 10 min at 0° C., the solution was allowed to warm to rt. After 50 min at rt, the solution was recooled to 0° C. and 7-(2-formyl-6-oxo-piperidin-1-yl)-hept-5-ynoic acid methyl ester (crude from previous reaction, ~0.92 mmol) in THF (2 mL) was added via cannula. The reaction was allowed to warm to rt. After 18 h at rt, the reaction was quenched with acetic acid and water (1:1, 15 mL) and extracted with EtOAc (3×40 mL). The combined organic phase was washed with brine (50 mL), dried ($Na_2SO_4$), filtered and concentrated in vacuo. Purification of the residue by flash column chromatography on silica gel (10%→50% EtOAc/$CH_2Cl_2$, gradient) afforded 175 mg (58%) of the title compound.

EXAMPLE 2

7-[2-Oxo-6-((E)-3-oxo-oct-1-enyl)-piperidin-1-yl]-hept-5-ynoic acid

Rabbit liver esterase (134 units/mg, 3 mg) was added to a solution of 7-[2-oxo-6-((E)-3-oxo-oct-1-enyl)-piperidin-1-yl]-hept-5-ynoic acid methyl ester (18 mg, 0.45 mmol) in acetonitrile (0.3 mL) and pH 7.2 phosphate buffer (3.0 mL). After 18.5 h, acetonitrile (10 mL) was added and the reaction mixture was concentrated to dryness in vacuo. Purification of the residue by flash column chromatography on silica gel ($CH_2Cl_2$→3% MeOH/$CH_2Cl_2$, gradient) afforded 17 mg (97%) of the title compound.

EXAMPLE 3

(Z)-7-[2-Oxo-6-((E)-3-oxo-oct-1-enyl)-piperidin-1-yl]-hept-5-enoic acid methyl ester A 50 mL round bottom flask was charged with nickel (11) chloride (273 mg, 2.10 mmol) and sodium borohydride (40 mg, 1.05 mmol), then 95% ethanol (2.0 mL) was added. The mixture immediately turned black. After 15 min at rt, ethylene diamine (0.23 mL, 3.36 mmol) was added. After another 15 min at rt, 7-[2-oxo-6-((E)-3-oxo-oct-1-enyl)-piperidin-1-yl]-hept-5-ynoic acid methyl ester (152 mg, 0.42 mmol) in 95% ethanol (2.0 mL) was added via cannula. A hydrogen atmosphere was established by evacuating and refilling with hydrogen (3×) and the reaction mixture was stirred under a balloon of hydrogen for 19 h. The reaction mixture was filtered through celite, washing with ethanol, and the filtrate was concentrated in vacuo. Purification of the resulting residue by flash column chromatography (10→50% EtOAc/$CH_2Cl_2$, gradient) afforded 65 mg (43%) of the title compound.

EXAMPLE 4

(Z)-7-[2-Oxo-6-((E)-3-oxo-oct-1-enyl)-piperidin-1-yl]-hept-5-enoic acid

In accordance with the procedure of example 2, (Z)-7-[2-oxo-6-((E)-3-oxo-oct-1-enyl)-piperidin-1-yl]-hept-5-enoic acid methyl ester (9 mg, 0.025 mmol) was converted into 5 mg (56%) of the title compound.

EXAMPLE 5

7-[2-Oxo-6-(3-oxo-octyl)-piperidin-1-yl]-heptanoic acid methyl ester

Palladium on carbon (10 wt. %, 5 mg) was added to a solution of (Z)-7-[2-oxo-6-((E)-3-oxo-oct-1-enyl)-piperidin-1-yl]-hept-5-enoic acid methyl ester (40 mg, 0.11 mmol) in MeOH (3.0 mL). A hydrogen atmosphere was established by evacuating and refilling with hydrogen (3×) and the reaction mixture was stirred under a balloon of hydrogen for 19 h. The reaction mixture was filtered through celite, washing with MeOH, and the filtrate was concentrated in vacuo to afford 38 mg (94%) of the title compound.

EXAMPLE 6

7-[2-Oxo-6-(3-oxo-octyl)-piperidin-1-yl]-heptanoic acid

In accordance with the procedure of example 2, 7-[2-oxo-6-(3-oxo-octyl)-piperidin-1-yl]-heptanoic acid methyl ester (14 mg, 0.038 mmol) was converted into 13 mg (97%) of the title compound.

EXAMPLE 7

7-[2-(3-Hydroxy-octyl)-6-oxo-piperidin-1-yl]-heptanoic acid methyl ester

Sodium borohydride (24 mg, 0.63 mmol), followed by MeOH (2 drops), was added to a solution of 7-[2-oxo-6-(3-oxo-octyl)-piperidin-1-yl]-heptanoic acid methyl ester (23 mg, 0.063 mmol) in $CH_2Cl_2$ (1.0 mL) at 0° C. The mixture was allowed to warm to rt. After 4 h at rt, the reaction was quenched with HCl (11.0M aqueous) and extracted with EtOAc (3×10 mL). The combined organic phase was washed with saturated aqueous $NaHCO_3$ (15 mL) and brine (15 mL) then dried ($Na_2SO_4$), filtered and concentrated in vacuo. Purification of the residue by flash column chromatography on silica gel ($CH_2Cl_2$→3% MeOH/$CH_2Cl_2$, gradient) afforded 14 mg (61%) of the title compound.

EXAMPLE 8

7-[2-(3-Hydroxy-octyl)-6-oxo-piperidin-1-yl]-heptanoic acid

In accordance with the procedure of example 2, 7-[2-(3-hydroxy-octyl)-6-oxo-piperidin-1-yl]-heptanoic acid methyl ester (11.5 mg, 0.031 mmol) was converted into 6 mg (53%) of the title compound.

EXAMPLE 9

(Z)-7-[2-((E)-3-Hydroxy-oct-1-enyl)-6-oxo-piperidin-1-yl]-hept-5-enoic acid methyl ester In accordance with the procedure of example 7, (Z)-7-[2-oxo-6-((E)-3-oxo-oct-1-enyl)-piperidin-1-yl]-hept-5-enoic acid methyl ester (32 mg, 0.087 mmol) was converted into 25 mg (78%) of the title compound.

EXAMPLE 10

(Z)-7-[2-((E)-3-Hydroxy-oct-1-enyl)-6-oxo-piperidin-1-yl]-hept-5-enoic acid

In accordance with the procedure of example 2, (Z)-7-[2-((E)-3-hydroxy-oct-1-enyl)-6-oxo-piperidin-1-yl]-hept-5-enoic acid methyl ester (10 mg, 0.028 mmol) was converted into 5 mg (52%) of the title compound.

EXAMPLE 11

7-[2-Oxo-6-((E)-3-oxo-oct-1-enyl)-piperidin-1-yl]-heptanoic acid methyl ester

Step 1. 7-(2-Hydroxymethyl-6-oxo-piperidin-1-yl)-heptanoic acid methyl ester

Palladium on carbon (10 wt. %, 20 mg) was added to a solution of 7-(2-hydroxymethyl-6-oxo-piperidin-1-yl)-hept-5-ynoic acid methyl ester (180 mg, 0.67 mmol) in MeOH (6.0 mL). A hydrogen atmosphere was established by evacuating and refilling with hydrogen (3×) and the reaction mixture was stirred under a balloon of hydrogen for 23 h. The reaction mixture was filtered through celite, washing with MeOH, and the filtrate was concentrated in vacuo to afford 184 mg (quant.) of 7-(2-hydroxymethyl-6-oxo-piperidin-1-yl)-heptanoic acid methyl ester.

Step 2. 7-(2-Formyl-6-oxo-piperidin-1-yl)-heptanoic acid methyl ester

EDCI (212 mg, 1.10 mmol) and DMSO (0.10 mL, 1.48 mmol) were added sequentially to a solution of 7-(2-hydroxymethyl-6-oxo-piperidin-1-yl)-heptanoic acid methyl ester (100 mg, 0.37 mmol) in benzene (4.0 mL) at rt. The mixture was cooled to 0° C. and pyridinium trifluoroacetate (79 mg, 0.41 mmol) was added. The reaction was allowed to warm to rt and then was stirred at rt for 3.5 h. The solution was decanted from the oily residue and the residue was washed with benzene (3×3 mL). The combined benzene phases were concentrated in vacuo to afford crude 7-(2-formyl-6-oxo-piperidin-1-yl)-heptanoic acid methyl ester that was used without further purification.

Step 3. 7-[2-Oxo-6-((E)-3-oxo-oct-1-enyl)-piperidin-1-yl]-heptanoic acid methyl ester Sodium hydride (60% dispersion in oil, 15 mg, 0.37 mmol) was added to a solution of dimethyl 2-oxoheptylphosphonate (87 mg, 0.33 mmol) in THF (2 mL) at 0° C. After 10 min at 0° C., the solution was allowed to warm to rt. After 1 h at rt, the solution was recooled to 0° C. and 7-(2-formyl-6-oxo-piperidin-1-yl)-heptanoic acid methyl ester (crude from previous reaction, ~0.37 mmol) in THF (2 mL) was added via cannula. The reaction was allowed to warm to rt. After 17 h at rt, the reaction was quenched with acetic acid (50% aqueous, 20 mL) and extracted with EtOAc (3×20 mL). The combined organic phase was washed with saturated aqueous $NaHCO_3$ (20 mL) and brine (20 mL), dried ($Na_2SO_4$), filtered and concentrated in vacuo. Purification of the residue by flash column chromatography on silica gel ($CH_2Cl_2$→2% MeOH/$CH_2Cl_2$, gradient) afforded 128 mg (95%) of the title compound.

EXAMPLE 12

7-[2-Oxo-6-((E)-3-oxo-oct-1-enyl)-piperidin-1-yl]-heptanoic acid

In accordance with the procedure of example 2, 7-[2-oxo-6-((E)-3-oxo-oct-1-enyl)-piperidin-1-yl]-heptanoic acid methyl ester (17 mg, 0.048 mmol) was converted into 2 mg (12%) of the title compound after flash column chromatography on silica gel ($CH_2Cl_2$→2% MeOH/$CH_2Cl_2$, gradient) and preparative thin layer chromatography (silica, 5% MeOH/$CH_2Cl_2$).

EXAMPLE 13

7-[2-((E)-3-Hydroxy-oct-1-enyl)-6-oxo-piperidin-1-yl]-heptanoic acid methyl ester Sodium borohydride (42 mg, 1.10 mmol), followed by MeOH (0.38 mL), was added to a solution of 7-[2-oxo-6-((E)-3-oxo-oct-1-enyl)-piperidin-1-yl]-heptanoic acid methyl ester (40 mg, 0.11 mmol) in $CH_2Cl_2$ (1.13 mL) at 0° C. The mixture was allowed to warm to rt. After 3 h at rt, the reaction was quenched with aqueous HCl (1.0 M) and extracted with EtOAc (3×10 mL). The combined organic phase was washed with brine (20 mL) then dried ($Na_2SO_4$), filtered and concentrated in vacuo to afford 40 mg (99%) of the title compound.

EXAMPLE 14

7-[2-((E)-3-Hydroxy-oct-1-enyl)-6-oxo-piperidin-1-yl]-heptanoic acid

In accordance with the procedure of example 2, 7-[2-((E)-3-Hydroxy-oct-1-enyl)-6-oxo-piperidin-1-yl]-heptanoic acid methyl ester (18 mg, 0.049 mmol) was converted into 6 mg (35%) of the title compound.

EXAMPLE 15

7-[2-Oxo-6-((E)-3-oxo-4-phenyl-but-1-enyl)-piperidin-1-yl]-heptanoic acid methyl ester Sodium hydride (60% dispersion in oil, 12 mg, 0.32 mmol) was added to a solution of dimethyl 2-oxo-3-phenylpropylphosphonate (70 mg, 0.29 mmol) in THF (1.5 mL) at 0° C. After 10 min at 0° C., the solution was allowed to warm to rt. After 50 min at rt, the solution was recooled to 0° C. and 7-(2-formyl-6-oxo-piperidin-1-yl)-heptanoic acid methyl ester (crude, prepared in accordance with example 11, step 2, ~0.32 mmol) in THF (1.5 mL) was added via cannula. The reaction was allowed to warm to rt. After 18 h at rt, the reaction was quenched with acetic acid (50% aqueous, 20 mL) and extracted with EtOAc (3×20 mL). The combined organic phase was washed with saturated aqueous $NaHCO_3$ (30 mL) and brine (30 mL), dried ($Na_2SO_4$), filtered and concentrated in vacuo. Purification of the residue by flash column chromatography on silica gel ($CH_2Cl_2$→2% MeOH/$CH_2Cl_2$, gradient) afforded 66 mg (59%) of the title compound.

EXAMPLE 16

7-[2-Oxo-6-((E)-3-oxo-4-phenyl-but-1-enyl)-piperidin-1-yl]-heptanoic acid

In accordance with the procedure of example 2, 7-[2-oxo-6-((E)-3-oxo-4-phenyl-but-1-enyl)-piperidin-1-yl]-heptanoic acid methyl ester (7 mg, 0.018 mmol) was converted into 2 mg (30%) of the title compound.

EXAMPLE 17

7-[2-((E)-3-Hydroxy-4-phenyl-but-1-enyl)-6-oxo-piperidin-1-yl]-heptanoic acid methyl ester Sodium borohydride (36 mg, 0.96 mmol), followed by MeOH (0.25 mL), was added to a solution of 7-[2-oxo-6-((E)-3-oxo-4-phenyl-but-1-enyl)-piperidin-1-yl]-heptanoic acid methyl ester (37 mg, 0.096 mmol) in $CH_2Cl_2$ (0.75 mL) at 0° C. The mixture was allowed to warm to rt. After 1.5 h at rt, the reaction was quenched with HCl (1.0 M aqueous) and extracted with EtOAc (3×10 mL). The combined organic phase was washed with saturated aqueous $NaHCO_3$ (20 mL) and brine (20 mL) then dried ($Na_2SO_4$), filtered and concentrated in vacuo. Purification of the residue by flash column chromatography on silica gel ($CH_2Cl_2$→3% MeOH/$CH_2Cl_2$, gradient) afforded 32 mg (86%) of the title compound.

EXAMPLE 18

7-[2-((E)-3-Hydroxy-4-phenyl-but-1-enyl)-6-oxo-piperidin-1-yl]-heptanoic acid In accordance with the procedure of example 2, 7-[2-((E)-3-hydroxy-4-phenyl-but-1-enyl)-6-oxo-piperidin-1-yl)-heptanoic acid methyl ester (10 mg, 0.026 mmol) was converted into 6.6 mg (68%) of the title compound.

EXAMPLE 19

7-[2-(3-Hydroxy-4-phenyl-butyl)-6-oxo-piperidin-1-yl]-heptanoic acid methyl ester Palladium on carbon (10 wt. %, 5 mg) was added to a solution of 7-[2-((E)-3-hydroxy-4-phenyl-but-1-enyl)-6-oxo-piperidin-1-yl]-heptanoic acid methyl ester (20 mg, 0.052 mmol) in MeOH (2.0 mL). A hydrogen atmosphere was established by evacuating and refilling with hydrogen (3×) and the reaction mixture was stirred under a balloon of hydrogen for 22 h. The reaction mixture was filtered through celite, washing with MeOH, and the filtrate was concentrated in vacuo to afford 13 mg (65%) of the title compound.

EXAMPLE 20

7-[2-(3-Hydroxy-4-phenyl-butyl)-6-oxo-piperidin-1-yl]-heptanoic acid

In accordance with the procedure of example 2, 7-[2-(3-hydroxy-4-phenyl-butyl)-6-oxo-piperidin-1-yl]-heptanoic acid methyl ester (11 mg, 0.029 mmol) was converted into 3.5 mg (32%) of the title compound.

EXAMPLE 21

7-[2-Oxo-6-(3-oxo-4-phenyl-butyl)-piperidin-1-yl]-heptanoic acid methyl ester In accordance with the procedure of example 19, 7-[2-oxo-6-((E)-3-oxo-4-phenyl-but-1-enyl)-piperidin-1-yl]-heptanoic acid methyl ester (20 mg, 0.052 mmol) was converted into 15 mg (75%) of the title compound.

EXAMPLE 22

7-[2-Oxo-6-(3-oxo-4-phenyl-butyl)-piperidin-1-yl]-heptanoic acid

In accordance with the procedure of example 2, 7-[2-oxo-6-(3-oxo-4-phenyl-butyl)-piperidin-1-yl]-heptanoic acid methyl ester (12 mg, 0.031 mmol) was converted into 2.8 mg (24%) of the title compound.

EXAMPLE 23

7-[2-Oxo-6-((E)-3-oxo-4-phenyl-but-1-enyl)-piperidin-1-yl]-hept-5-ynoic acid methyl ester Sodium hydride (60% dispersion in oil, 23 mg, 0.58 mmol) was added to a solution of dimethyl 2-oxo-3-phenylpropylphosphonate (171 mg, 0.64 mmol) in THF (2.0 mL) at 0° C. After 10 min at 0° C., the solution was allowed to warm to rt. After 50 min at rt, the solution was recooled to 0° C. and 7-(2-formyl-6-oxo-piperidin-1-yl)-hept-5-ynoic acid methyl ester (crude, prepared in accordance with example 1, step 4, ~0.64 mmol) in THF (2.0 mL) was added via cannula. The reaction was allowed to warm to rt. After 18 h at rt, the reaction was quenched with acetic acid (50% aqueous, 20 mL) and extracted with EtOAc (3×20 mL). The combined organic phase was washed with saturated aqueous $NaHCO_3$ (30 mL) and brine (30 mL), dried ($Na_2SO_4$), filtered and concentrated in vacuo. Purification of the residue by flash column chromatography on silica gel twice (1st $CH_2Cl_2$→2% $MeOH/CH_2Cl_2$, gradient and 2nd $CH_2Cl_2$→30% $EtOAc/CH_2Cl_2$, gradient) afforded 51 mg (21%) of the title compound.

EXAMPLE 24

7-[2-Oxo-6-((E)-3-oxo-4-phenyl-but-1-enyl)-piperidin-1-yl]-hept-5-ynoic acid

In accordance with the procedure of example 2, 7-[2-Oxo-6-((E)-3-oxo-4-phenyl-but-1-enyl)-piperidin-1-yl]-hept-5-ynoic acid methyl ester (9 mg, 0.024 mmol) was converted into 1.4 mg (16%) of the title compound.

EXAMPLE 25

(Z)-7-[2-Oxo-6-((E)-3-oxo-4-phenyl-but-1-enyl)-piperidin-1-yl]-hept-5-enoic acid methyl ester A round bottom flask was charged with nickel (II) chloride (68 mg, 0.52 mmol) and sodium borohydride (9.9 mg, 0.26 mmol), then 95% ethanol (1.0 mL) was added. The mixture immediately turned black. After 15 min at rt, ethylene diamine (56 μL, 0.84 mmol) was added. After another 15 min at rt, 7-[2-oxo-6-((E)-3-oxo-4-phenyl-but-1-enyl)-piperidin-1-yl]-hept-5-ynoic acid methyl ester (40 mg, 0.10 mmol) in 95% ethanol (1.0 mL) was added via cannula. A hydrogen atmosphere was established by evacuating and refilling with hydrogen (3×) and the reaction mixture was stirred under a balloon of hydrogen for 18 h. The reaction mixture was filtered through celite, washing with ethanol, and the filtrate was concentrated in vacuo. Purification of the resulting residue by flash column chromatography ($CH_2Cl_2$→30% $EtOAc/CH_2Cl_2$, gradient) afforded 28 mg (70%) of the title compound.

EXAMPLE 26

(Z)-7-[2-Oxo-6-((E)-3-oxo-4-phenyl-but-1-enyl)-piperidin-1-yl]-hept-5-enoic acid In accordance with the procedure of example 2, (Z)-7-[2-oxo-6-((E)-3-oxo-4-phenyl-but-1-enyl)-piperidin-1-yl]-hept-5-enoic acid methyl ester (9.2 mg, 0.024 mmol) was converted into 8 mg (90%) of the title compound.

EXAMPLE 27

(Z)-7-[2-((E)-3-Hydroxy-4-phenyl-but-1-enyl)-6-oxo-piperidin-1-yl]-hept-5-enoic acid methyl ester Sodium borohydride (16 mg, 0.42 mmol), followed by MeOH (0.25 mL), was added to a solution of (Z)-7-[2-oxo-6-((E)-3-oxo-4-phenyl-but-1-enyl)-piperidin-1-yl]-hept-5-enoic acid methyl ester (16 mg, 0.042 mmol) in $CH_2Cl_2$ (0.75 mL) at 0° C. The mixture was allowed to warm to rt. After 2.5 h at rt, the reaction was quenched with aqueous HCl (1.0 M) and extracted with EtOAc (3×15 mL). The combined organic phase was washed with saturated aqueous $NaHCO_3$ (15 mL) and brine (15 mL) then dried ($Na_2SO_4$), filtered and concentrated in vacuo. Purification of the residue by flash column chromatography on silica gel ($CH_2Cl_2$→50% $EtOAc/CH_2Cl_2$, gradient) afforded 10 mg (62%) of the title compound.

EXAMPLE 28

(Z)-7-[2-((E)-3-Hydroxy-4-phenyl-but-1-enyl)-6-oxo-piperidin-1-yl]-hept-5-enoic acid In accordance with the procedure of example 2, (Z)-7-[2-((E)-3-hydroxy-4-phenyl-but-1-enyl)-6-oxo-piperidin-1-yl]-hept-5-enoic acid methyl ester (8.5 mg, 0.022 mmol) was converted into 2.4 mg (29%) of the title compound.

EXAMPLE 29

7-[(R)-2-((E)-3-Hydroxy-4-phenyl-but-1-enyl)-6-oxo-piperidin-1-yl]-heptanoic acid methyl ester Step 1. (R)-6-(tert-Butyldimethylsilanyloxymethyl)-piperidin-2-one Imidazole (773 mg, 11.4 mmol) and tert-butyldimethylsilyl chloride (787 mg, 5.22 mmol) were added sequentially to a solution of (R)-6-hydroxymethyl-piperidin-2-one (prepared from D-□-aminoadipic acid according to Huang, et al., *Synth. Commun.* 1989, 19, 3485-3496, 613 mg, 4.75 mmol) in DMF (8 mL) at 0° C. The reaction mixture was allowed to warm to rt and was stirred at rt for 20 h. Benzene and EtOAc (3:7, 200 mL) was added and the solution was washed with brine (3×50 mL). The organic phase was dried ($Na_2SO_4$), filtered and concentrated in vacuo. Purification of the residue by flash column chromatography on silica gel ($CH_2Cl_2$→3% $MeOH/CH_2Cl_2$, gradient) afforded 1.13 g (98%) of (R)-6-(tert-butyldimethylsilanyloxymethyl)-piperidin-2-one as a white solid.

Step 2. 7-[(R)-2-tert-Butyldimethylsilanyloxymethyl)-6-oxo-piperidin-1-yl]-hept-5-ynoic acid methyl ester Sodium hydride (60% dispersion in oil, 195 mg, 4.87 mmol) was added to a solution of (R)-6-(tert-butyldimethylsilanyloxymethyl)-piperidin-2-one (1.13 g, 4.64 mmol) in DMF (8 mL) at rt. After 1 h, methyl 7-iodohept-5-ynoate (1.35 g, 5.07 mmol) in DMF (2 mL) was added via cannula. After 18 h at rt, the reaction was quenched by the addition of aqueous HCl (0.5 M, 25 mL) and the mixture was extracted with EtOAc (3×50 mL). The combined organic phase was washed with saturated aqueous $NaHCO_3$ (50 mL) and brine (3×50 mL), dried ($Na_2SO_4$), filtered and concentrated in vacuo. Purification of the residue by flash column chromatography on silica gel ($CH_2Cl_2$→50% $EtOAc/CH_2Cl_2$, gradient) afforded 713 mg (40%) of 7-[(R)-2-tert-butyldimethylsilanyloxymethyl)-6-oxo-piperidin-1-yl]-hept-5-ynoic acid methyl ester.

Step 3. 7-((R)-2-Hydroxymethyl-6-oxo-piperidin-1-yl)-hept-5-ynoic acid methyl ester Hydrogen fluoride-pyridine (2 mL) was added to a solution of 7-[(R)-2-tert-butyldimethylsilanyloxymethyl)-6-oxo-piperidin-1-yl]-hept-5-ynoic acid methyl ester (705 g, 1.85 mmol) in acetonitrile (4.0 mL) in a plastic scintillation vial. After 3.5 h at rt, the reaction was quenched with saturated aqueous $NaHCO_3$ (50 mL) and the mixture was extracted with EtOAc (3×30 mL). The combined organic phase was washed with brine (50 mL), dried ($MgSO_4$), filtered and concentrated in vacuo. Purification of the residue by flash column chromatography on silica gel ($CH_2Cl_2$→3% MeOH/$CH_2Cl_2$, gradient) afforded 347 mg (70%) of 7-((R)-2-hydroxymethyl-6-oxo-piperidin-1-yl)-hept-5-ynoic acid methyl ester.

Step 4. 7-((R)-2-Hydroxymethyl-6-oxo-piperidin-1-yl)-heptanoic acid methyl ester Palladium on carbon (10 wt. %, 10 mg) was added to a solution of 7-((R)-2-hydroxymethyl-6-oxo-piperidin-1-yl)-hept-5-ynoic acid methyl ester (110 mg, 0.41 mmol) in MeOH (3.0 mL). A hydrogen atmosphere was established by evacuating and refilling with hydrogen (3×) and the reaction mixture was stirred under a balloon of hydrogen for 22 h. The reaction mixture was filtered through celite, washing with MeOH, and the filtrate was concentrated in vacuo to afford 110 mg (99%) of 7-((R)-2-hydroxymethyl-6-oxo-piperidin-1-yl)-heptanoic acid methyl ester.

Step 5. 7-((R)-2-Formyl-6-oxo-piperidin-1-yl)-heptanoic acid methyl ester

EDCI (119 mg, 0.62 mmol) and DMSO (59 μL, 0.83 mmol) were added sequentially to a solution of 7-((R)-2-hydroxymethyl-6-oxo-piperidin-1-yl)-heptanoic acid methyl ester (56 mg, 0.21 mmol) in benzene (2.0 mL) at rt. The mixture was cooled to 0° C. and pyridinium trifluoroacetate (44 mg, 0.23 mmol) was added. The reaction was allowed to warm to rt and then was stirred at rt for 3 h. The solution was decanted from the oily residue and the residue was washed with benzene (3×2 mL). The combined benzene phases were concentrated in vacuo to afford crude 7-((R)-2-formyl-6-oxo-piperidin-1-yl)-heptanoic acid methyl ester that was used without further purification.

Step 6. 7-[(R)-2-Oxo-6-((E)-3-oxo-4-phenyl-but-1-enyl)-piperidin-1-yl]-heptanoic acid methyl ester Sodium hydride (60% dispersion in oil, 8.2 mg, 0.21 mmol) was added to a solution of dimethyl 2-oxo-3-phenylpropylphosphonate (45 mg, 0.19 mmol) in THF (1.0 mL) at 0° C. After 10 min at 0° C., the solution was allowed to warm to rt. After 1 h at rt, the solution was recooled to 0° C. and 7-((R)-2-formyl-6-oxo-piperidin-1-yl)-heptanoic acid methyl ester (crude from previous reaction, ~0.21 mmol) in THF (1.0 mL) was added via cannula. The reaction was allowed to warm to rt. After 18 h at rt, the reaction was quenched with acetic acid (50% aqueous, 10 mL) and extracted with EtOAc (3×15 mL). The combined organic phase was washed with saturated aqueous $NaHCO_3$ (20 mL) and brine (20 mL), dried ($Na_2SO_4$), filtered and concentrated in vacuo. Purification of the residue by flash column chromatography on silica gel ($CH_2Cl_2$→2% MeOH/$CH_2Cl_2$, gradient) afforded 36.5 mg (51%) of 7-[(R)-2-oxo-6-((E)-3-oxo-4-phenyl-but-1-enyl)-piperidin-1-yl]-heptanoic acid methyl ester.

Step 7. 7-[(R)-2-((E)-3-Hydroxy-4-phenyl-but-1-enyl)-6-oxo-piperidin-1-yl]-heptanoic acid methyl ester Sodium borohydride (35 mg, 0.93 mmol), followed by MeOH (0.25 mL), was added to a solution of 7-[(R)-2-oxo-6-((E)-3-oxo-4-phenyl-but-1-enyl)-piperidin-1-yl]-heptanoic acid methyl ester (36 mg, 0.093 mmol) in $CH_2Cl_2$ (0.75 mL) at 0° C. The mixture was allowed to warm to rt. After 3 h at rt, the reaction was quenched with aqueous HCl (0.5 M, 5 mL) and extracted with EtOAc (3×10 mL). The combined organic phase was washed with saturated aqueous $NaHCO_3$ (10 mL) and brine (10 mL) then dried ($Na_2SO_4$), filtered and concentrated in vacuo. Purification of the residue by preparative thin layer chromatography (silica, 5% MeOH/$CH_2Cl_2$) afforded 20 mg (55%) of the title compound.

EXAMPLE 30

7-[(R)-2-((E)-3-Hydroxy-4-phenyl-but-1-enyl)-6-oxo-piperidin-1-yl]-heptanoic acid Rabbit liver esterase (134 units/mg, 1 mg) was added to a solution of 7-[(R)-2-((E)-3-hydroxy-4-phenyl-but-1-enyl)-6-oxo-piperidin-1-yl]-heptanoic acid methyl ester (15 mg, 0.39 mmol) in acetonitrile (0.2 mL) and pH 7.2 phosphate buffer (3.0 mL). After 16.5 h, acetonitrile (5 mL) was added and the reaction mixture was concentrated to dryness in vacuo. Purification of the residue by flash column chromatography on silica gel ($CH_2Cl_2$→2% MeOH/$CH_2Cl_2$, gradient) afforded 8.7 mg (60%) of the title compound.

EXAMPLE 31

7-[(R)-2-((E)-3-Hydroxy-oct-1-enyl)-6-oxo-piperidin-1-yl]-heptanoic acid methyl ester Step 1. 7-[(R)-2-Oxo-6-((E)-3-oxo-oct-1-enyl)-piperidin-1-yl]-heptanoic acid Sodium hydride (60% dispersion in oil, 7.2 mg, 0.18 mmol) was added to a solution of dimethyl 2-oxoheptylphosphonate (47 mg, 0.19 mmol) in THF (1 mL) at 0° C. After 10 min at 0° C., the solution was allowed to warm to rt. After 1 h at rt, the solution was recooled to 0° C. and 7-((R)-2-formyl-6-oxo-piperidin-1-yl)-heptanoic acid methyl ester (crude, prepared in accordance with Example 29, step 5, ~0.20 mmol) in THF (1 mL) was added via cannula. The reaction was allowed to warm to rt. After 17 h at rt, the reaction was quenched with aqueous acetic acid (50%, 5 mL) and extracted with EtOAc (3×10 mL). The combined organic phase was washed with saturated aqueous $NaHCO_3$ (10 mL) and brine (10 mL) then dried ($Na_2SO_4$), filtered and concentrated in vacuo. Purification of the residue by flash column chromatography on silica gel ($CH_2Cl_2$→2% MeOH/$CH_2Cl_2$, gradient) afforded 59 mg (90%) of 7-[(R)-2-oxo-6-((E)-3-oxo-oct-1-enyl)-piperidin-1-yl]-heptanoic acid methyl ester.

Step 2. 7-[(R)-2-((E)-3-Hydroxy-oct-1-enyl)-6-oxo-piperidin-1-yl]-heptanoic acid methyl ester Sodium borohydride (28 mg, 0.74 mmol), followed by MeOH (0.25 mL), was added to a solution of 7-[(R)-2-oxo-6-((E)-3-oxo-oct-1-enyl)-piperidin-1-yl]-heptanoic acid methyl ester (55 mg, 0.15 mmol) in $CH_2Cl_2$ (0.75 mL) at 0° C. The mixture was allowed to warm to rt. After 1 h at rt, the reaction was quenched with aqueous HCl (1.0 M, 2 mL) and extracted with EtOAc (3×10 mL). The combined organic phase was washed with brine (10 mL) then dried ($Na_2SO_4$), filtered and concentrated in vacuo to afford 55 mg (99%) of the title compound.

EXAMPLE 32

7-[(R)-2-((E)-3-Hydroxy-oct-1-enyl)-6-oxo-piperidin-1-yl]-heptanoic acid

In accordance with the procedure of example 2, 7-[(R)-2-((E)-3-hydroxy-oct-1-enyl)-6-oxo-piperidin-1-yl]-heptanoic acid methyl ester (23 mg, 0.063 mmol) was converted into 10 mg (45%) of the title compound.

EXAMPLE 33

7-[(R)-2-(3-Hydroxy-octyl)-6-oxo-piperidin-1-yl]-heptanoic acid methyl ester

Palladium on carbon (10 wt. %, 7 mg) was added to a solution of 7-[(R)-2-((E)-3-hydroxy-oct-1-enyl)-6-oxo-piperidin-1-yl]-heptanoic acid methyl ester (33 mg, 0.90 mmol) in MeOH (3.0 mL). A hydrogen atmosphere was established by evacuating and refilling with hydrogen (3×) and the reaction mixture was stirred under a balloon of hydrogen for 18.5 h. The reaction mixture was filtered through celite, washing with MeOH, and the filtrate was concentrated in vacuo to afford 28 mg (84%) of the title compound.

EXAMPLE 34

7-[(R)-2-(3-Hydroxy-octyl)-6-oxo-piperidin-1-yl]-heptanoic acid

In accordance with the procedure of example 2, 7-[(R)-2-(3-hydroxy-octyl)-6-oxo-piperidin-1-yl]-heptanoic acid methyl ester (24 mg, 0.065 mmol) was converted into 22 mg (95%) of the title compound.

EXAMPLE 35 AND EXAMPLE 36

7-[(R)-2-((E)-3-Hydroxy-oct-1-enyl)-6-oxo-piperidin-1-yl]-hept-5-ynoic acid methyl ester and (R)-1-(7-Hydroxy-hept-2-ynyl)-6-((E)-3-hydroxy-oct-1-enyl)-piperidin-2-one Step 1. 7-((R)-2-Formyl-6-oxo-piperidin-1-yl)-hept-5-ynoic acid methyl ester EDCI (127 mg, 0.66 mmol) and DMSO (62 μL, 0.87 mmol) were added sequentially to a solution of 7-((R)-2-hydroxymethyl-6-oxo-piperidin-1-yl)-hept-5-ynoic acid methyl ester (prepared in accordance with Example 29, step 3, 59 mg, 0.22 mmol) in benzene (2.0 mL) at rt. The mixture was cooled to 0° C. and pyridinium trifluoroacetate (47 mg, 0.24 mmol) was added. The reaction was allowed to warm to rt and then was stirred at rt for 2 h. The solution was decanted from the oily residue and the residue was washed with benzene (3×2 mL). The combined benzene phases were concentrated in vacuo to afford crude 7-((R)-2-formyl-6-oxo-piperidin-1-yl)-hept-5-ynoic acid methyl ester that was used without further purification.

Step 2. 7-[(R)-2-Oxo-6-((E)-3-oxo-oct-1-enyl)-piperidin-1-yl]-hept-5-ynoic acid methyl ester Sodium hydride (60% dispersion in oil, 8.8 mg, 0.22 mmol) was added to a solution of dimethyl 2-oxoheptylphosphonate (52 mg, 0.23 mmol) in THF (1 mL) at 0° C. After 10 min at 0° C., the solution was allowed to warm to rt. After 1 h at rt, the solution was recooled to 0° C. and 7-((R)-2-formyl-6-oxo-piperidin-1-yl)-hept-5-ynoic acid methyl ester (crude from previous reaction, ~0.22 mmol) in THF (1 mL) was added via cannula. The reaction was allowed to warm to rt. After 18.5 h at rt, the reaction was quenched with aqueous acetic acid (50%, 5 mL) and extracted with EtOAc (3×10 mL). The combined organic phase was washed with saturated aqueous $NaHCO_3$ (10 mL) and brine (10 mL) then dried ($Na_2SO_4$), filtered and concentrated in vacuo. Purification of the residue by flash column chromatography on silica gel ($CH_2Cl_2$<2% MeOH/$CH_2Cl_2$, gradient) afforded 68 mg (85%) of 7-[(R)-2-oxo-6-((E)-3-oxo-oct-1-enyl)-piperidin-1-yl]-hept-5-ynoic acid methyl ester.

Step 3. 7-[(R)-2-((E)-3-Hydroxy-oct-1-enyl)-6-oxo-piperidin-1-yl]-hept-5-ynoic acid methyl ester and (R)-1-(7-Hydroxy-hept-2-ynyl)-6-((E)-3-hydroxy-oct-1-enyl)-piperidin-2-one Sodium borohydride (35 mg, 0.93 mmol), followed by MeOH (0.25 mL), was added to a solution of 7-[(R)-2-oxo-6-((E)-3-oxo-oct-1-enyl)-piperidin-1-yl]-hept-5-ynoic acid methyl ester (68 mg, 0.19 mmol) in $CH_2Cl_2$ (1.0 mL) at 0° C. The mixture was allowed to warm to rt. After 1 h at rt, the reaction was quenched with aqueous HCl (1.0 M, 3 mL) and extracted with EtOAc (3×10 mL). The combined organic phase was washed with brine (20 mL) then dried ($Na_2SO_4$), filtered and concentrated in vacuo. Purification of the residue by flash column chromatography on silica gel ($CH_2Cl_2$→3% MeOH/$CH_2Cl_2$, gradient) afforded 26 mg (38%) of 7-[(R)-2-((E)-3-hydroxy-oct-1-enyl)-6-oxo-piperidin-1-yl]-hept-5-ynoic acid methyl ester and 5.3 mg (8%) of (R)-1-(7-hydroxy-hept-2-ynyl)-6-((E)-3-hydroxy-oct-1-enyl)-piperidin-2-one.

EXAMPLE 37

(Z)-7-[(R)-2-((E)-3-Hydroxy-oct-1-enyl)-6-oxo-piperidin-1-yl]-hept-5-enoic acid methyl ester Palladium on carbon (10 wt. %, 3 mg) was added to a solution of solution of 7-[(R)-2-((E)-3-hydroxy-oct-1-enyl)-6-oxo-piperidin-1-yl]-hept-5-ynoic acid methyl ester (13.5 mg, 0.037 mmol) in MeOH (2.0 mL). A hydrogen atmosphere was established by evacuating and refilling with hydrogen (3×) and the reaction mixture was stirred under a balloon of hydrogen for 23 h. The reaction mixture was filtered through celite, washing with ethanol, and the filtrate was concentrated in vacuo to afford 13.2 mg (97%) of the title compound.

EXAMPLE 38

(Z)-7-[(R)-2-((E)-3-Hydroxy-oct-1-enyl)-6-oxo-piperidin-1-yl]-hept-5-enoic acid

In accordance with the procedure of example 2, (Z)-7-[(R)-2-((E)-3-hydroxy-oct-1-enyl)-6-oxo-piperidin-1-yl]-hept-5-enoic acid methyl ester (10.5 mg, 0.029 mmol) was converted into 1.3 mg (13%) of the title compound.

EXAMPLE 39

(Z)-7-[(R)-2-((E)-3-Hydroxy-4-phenyl-but-1-enyl)-6-oxo-piperidin-1-yl]-hept-5-enoic acid methyl ester Step 1. 7-((R)-2-Hydroxymethyl-6-oxo-piperidin-1-yl)-hept-5-enoic acid methyl ester 95% Ethanol (0.5 mL) was added to a mixture of nickel (II) chloride (105 mg, 0.81 mmol) and sodium borohydride (15 mg, 0.40 mmol). The mixture immediately turned black. After 15 min at rt, ethylene diamine (86 μL, 1.29 mmol) was added. After 15 min at rt, a solution of 7-((R)-2-hydroxymethyl-6-oxo-piperidin-1-yl)-hept-5-ynoic acid methyl ester (from Example 1, step 3, 43.3 mg, 0.16 mmol) in 95% ethanol (1.0 mL) was added via cannula. A hydrogen atmosphere was established by evacuating and refilling with hydrogen (3×) and the reaction mixture was stirred under a balloon of hydrogen for 19 h. The reaction mixture was filtered through celite, washing with ethanol, and the filtrate was concentrated in vacuo. Purification of the residue by flash column chromatography on silica gel ($CH_2Cl_2$→3% MeOH/$CH_2Cl_2$, gradient) afforded 16.7 mg (38%) of 7-((R)-2-hydroxymethyl-6-oxo-piperidin-1-yl)-hept-5-enoic acid methyl ester.

Step 2. 7-((R)-2-Formyl-6-oxo-piperidin-1-yl)-hept-5-enoic acid methyl ester

EDCI (36 mg, 0.19 mmol) and DMSO (18 μL, 0.25 mmol) were added sequentially to a solution of 7-((R)-2-hydroxymethyl-6-oxo-piperidin-1-yl)-hept-5-enoic acid methyl ester (16.7 mg, 0.062 mmol) in benzene (1.0 mL) at rt. The mixture was cooled to 0° C. and pyridinium trifluoroacetate (13.2 mg, 0.068 mmol) was added. The reaction was allowed to warm to rt and then was stirred at rt for 2.5 h. The solution was decanted from the oily residue and the residue was washed with benzene (3×1 mL). The combined benzene phases were concentrated in vacuo to afford crude 7-((R)-2-formyl-6-oxo-piperidin-1-yl)-hept-5-enoic acid methyl ester that was used without further purification.

Step 3. 7-[(R)-2-Oxo-6-((E)-3-oxo-4-phenyl-but-1-enyl)-piperidin-1-yl]-hept-5-enoic acid methyl ester Sodium hydride (60% dispersion in oil, 2.5 mg, 0.063 mmol) was added to a solution of dimethyl 2-oxo-3-phenylpropylphosphonate (14 mg, 0.058 mmol) in THF (0.3 mL) at 0° C. After 1 h at 0° C. rt, 7-((R)-2-formyl-6-oxo-piperidin-1-yl)-hept-5-enoic acid methyl ester (crude from previous reaction, ~0.062 mmol) in THF (0.7 mL) was added via cannula. The reaction was allowed to warm to rt. After 18 h at rt, the reaction was quenched with acetic acid (50% aqueous, 5 mL) and extracted with EtOAc (3×5 mL). The combined organic phase was washed brine (10 mL), dried ($Na_2SO_4$), filtered and concentrated in vacuo. Purification of the residue by flash column chromatography on silica gel ($CH_2Cl_2$→25% EtOAc/$CH_2Cl_2$, gradient) afforded 10 mg (42%) of 7-[(R)-2-oxo-6-((E)-3-oxo-4-phenyl-but-1-enyl)-piperidin-1-yl]-hept-5-enoic acid methyl ester.

Step 4. 7-[(R)-2-((E)-3-Hydroxy-4-phenyl-but-1-enyl)-6-oxo-piperidin-1-yl]-hept-5-enoic acid methyl ester Sodium borohydride (2.0 mg, 0.053 mmol), followed by MeOH (0.1 mL), was added to a solution of 7-[(R)-2-oxo-6-((E)-3-oxo-4-phenyl-but-1-enyl)-piperidin-1-yl]-hept-5-enoic acid methyl ester (10 mg, 0.026 mmol) in $CH_2Cl_2$ (0.5 mL) at 0° C. The mixture was allowed to warm to rt. After 10 min at rt, the reaction was quenched with aqueous HCl (1.0 M, 1 mL) and extracted with EtOAc (3×5 mL). The combined organic phase was washed with brine (10 mL) then dried ($Na_2SO_4$), filtered and concentrated in vacuo. Purification of the residue by flash column chromatography on silica gel ($CH_2Cl_2$→2% MeOH/$CH_2Cl_2$, gradient) afforded 9.9 mg (98%) of the title compound.

EXAMPLE 40

(Z)-7-[(R)-2-((E)-3-Hydroxy-4-phenyl-but-1-enyl)-6-oxo-piperidin-1-yl]-hept-5-enoic acid In accordance with the procedure of example 2, (Z)-7-[(R)-2-((E)-3-hydroxy-4-phenyl-but-1-enyl)-6-oxo-piperidin-1-yl]-hept-5-enoic acid methyl ester (6.9 mg, 0.018 mmol) was converted into 2.0 mg (30%) of the title compound.

EXAMPLE 41

7-[(R)-2-((E)-3-Hydroxy-4-phenyl-but-1-enyl)-6-oxo-piperidin-1-yl]-hept-5-ynoic acid methyl ester Step 1. 7-[(R)-2-Oxo-6-((E)-3-oxo-4-phenyl-but-1-enyl)-piperidin-1-yl]-hept-5-ynoic acid methyl ester Sodium hydride (60% dispersion in oil, 3.8 mg, 0.095 mmol) was added to a solution of dimethyl 2-oxo-3-phenylpropylphosphonate (21 mg, 0.087 mmol) in THF (0.5 mL) at 0° C. After 1 h at 0° C. rt, 7-((R)-2-formyl-6-oxo-piperidin-1-yl)-hept-5-ynoic acid methyl ester (prepared in accordance with example 7, step 1, crude, ~0.095 mmol) in THF (0.5 mL) was added via cannula. The reaction was allowed to warm to rt. After 17.5 h at rt, the reaction was quenched with acetic acid (50% aqueous, 5 mL) and extracted with EtOAc (3×5 mL). The combined organic phase was washed brine (10 mL), dried ($Na_2SO_4$), filtered and concentrated in vacuo. Purification of the residue by flash column chromatography on silica gel ($CH_2Cl_2$→30% EtOAc/$CH_2Cl_2$, gradient) afforded 14 mg (42%) of 7-[(R)-2-oxo-6-((E)-3-oxo-4-phenyl-but-1-enyl)-piperidin-1-yl]-hept-5-ynoic acid methyl ester.

Step 2. 7-[(R)-2-((E)-3-Hydroxy-4-phenyl-but-1-enyl)-6-oxo-piperidin-1-yl]-hept-5-ynoic acid methyl ester Sodium borohydride (2 mg, 0.053 mmol), followed by MeOH (0.1 mL), was added to a solution of 7-[(R)-2-oxo-6-((E)-3-oxo-4-phenyl-but-1-enyl)-piperidin-1-yl]-hept-5-ynoic acid methyl ester (14 mg, 0.037 mmol) in $CH_2Cl_2$ (0.5 mL) at 0° C. The mixture was allowed to warm to rt. After 30 min at rt, the reaction was quenched with aqueous HCl (1.0 M, 1 mL) and extracted with EtOAc (3×5 mL). The combined organic phase was washed with brine (10 mL) then dried ($Na_2SO_4$), filtered and concentrated in vacuo. Purification of the residue by flash column chromatography on silica gel ($CH_2Cl_2$→2% MeOH/$CH_2Cl_2$, gradient) afforded 11 mg (78%) of the title compound.

EXAMPLE 42

7-[(R)-2-((E)-3-Hydroxy-4-phenyl-but-1-enyl)-6-oxo-piperidin-1-yl]-hept-5-ynoic acid In accordance with the procedure of example 2, 7-[(R)-2-((E)-3-hydroxy-4-phenyl-but-1-enyl)-6-oxo-piperidin-1-yl]-hept-5-ynoic acid methyl ester (8.7 mg, 0.023 mmol) was converted into 4.1 mg (49%) of the title compound.

EXAMPLE 43

7-[(R)-2-((E)-3-Hydroxy-4-phenyl-but-1-enyl)-6-oxo-piperidin-1-yl]-heptanoic acid isopropyl ester A mixture of 7-[(R)-2-((E)-3-hydroxy-4-phenyl-but-1-enyl)-6-oxo-piperidin-1-yl]-heptanoic acid (9.7 mg, 0.026 mmol), 1-isopropyl-3-p-tolyltriazene (5 mg, 0.028 mmol) and acetone (0.5 mL) was stirred at rt for 18 h. The reaction was quenched with saturated aqueous $NH_4Cl$ (2 mL) and extracted with $CH_2Cl_2$ (3×3 mL). The combined organic phase was dried ($Na_2SO_4$), filtered and concentrated in vacuo. Purification of the residue by flash column chromatography on silica gel (50% $CH_2Cl_2$/Hexane→$CH_2Cl_2$→2% MeOH/$CH_2Cl_2$, gradient) afforded 5.1 mg (47%) of the title compound.

EXAMPLE 44

7-[(R)-2-((E)-3-Hydroxy-4-phenyl-but-1-enyl)-6-oxo-piperidin-1-yl]-heptanoic acid amide Triethylamine (9 μL, 0.065 mmol) was added to a solution of 7-[(R)-2-((E)-3-hydroxy-4-phenyl-but-1-enyl)-6-oxo-piperidin-1-yl]-heptanoic acid (11.3 mg, 0.030 mmol) in $CH_2Cl_2$ (0.3 mL) at rt. After cooling to 0° C., ethyl chloroformate (3.2 μL, 0.033 mmol) was added. After 1 h at 0° C., a solution of ammonia (0.5 M in 1,4-dioxane, 0.3 mL, 0.15 mmol) was added and the reaction mixture was allowed to warm to rt. After 18 h at rt, the reaction mixture was diluted with EtOAc (10 mL) and washed with aqueous HCl (0.5 M, 3 mL), saturated aqueous $NaHCO_3$ (5 mL) and brine (5 mL) then dried ($Na_2SO_4$), filtered and concentrated in vacuo. Purification of the residue by flash column chromatography on silica gel ($CH_2Cl_2$→3% MeOH/$CH_2Cl_2$, gradient) afforded 3.5 mg (31%) of the title compound.

EXAMPLE 45 AND EXAMPLE 46

7-[(R)-2-((E)-3-Hydroxy-4-phenyl-but-1-enyl)-6-oxo-piperidin-1-yl]-heptanoic acid isopropyl ester (Faster Eluting Diastereomer by HPLC) and 7-[(R)-2-((E)-3-Hydroxy-4-phenyl-but-1-enyl)-6-oxo-piperidin-1-yl]-heptanoic acid isopropyl ester (Slower Eluting Disastereomer by HPLC)

The two diastereomers of example 15 (47 mg, 0.11 mmol) dissolved in 20% EtOAc/Hexane (1.75 mL) were separated in three batches (0.5 mL, 0.5 mL and 0.75 mL) on a Waters 600 HPLC instrument employing a Waters 2996 PDA detector and a Whatman Partisil® 10 column having dimensions of 9.4×500 mm. Using EtOAc as the eluent and a flow rate of 8 mL/min, the first diastereomer (7.8 mg total isolated) eluted at 18 min, and the second diastereomer (9 mg total isolated) eluted at 22 min.

EXAMPLE 47

7-[(R)-2-((E)-3-Hydroxy-4-phenyl-but-1-enyl)-6-oxo-piperidin-1-yl]-hept-5-ynoic acid isopropyl ester 1,8-Diazabicyclo[5.4.0]undec-7-ene (15 μL, 0.10 mmol) was added to a solution of 7-[(R)-2-((E)-3-hydroxy-4-phenyl-but-1-enyl)-6-oxo-piperidin-1-yl]-hept-5-ynoic acid (25 mg, 0.068 mmol) in acetone (0.68 mL) at rt. After 5 min, 2-iodopropane (34 μL, 0.34 mmol) was added. After 18 h at rt, the reaction mixture was diluted with EtOAc (25 mL) and washed with aqueous HCl (0.5 M, 10 mL), saturated aqueous $NaHCO_3$ (10 mL) and brine (10 mL) then dried ($Na_2SO_4$), filtered and concentrated in vacuo. Purification of the residue by flash column chromatography on silica gel ($CH_2Cl_2$→5% MeOH/$CH_2Cl_2$, gradient) afforded 13 mg (47%) of the title compound.

EXAMPLE 48 AND EXAMPLE 49

7-[(R)-2-((E)-3-Hydroxy-4-phenyl-but-1-enyl)-6-oxo-piperidin-1-yl]-hept-5-ynoic acid isopropyl ester (Faster Eluting Diastereomer by HPLC) and 7-[(R)-2-((E)-3-Hydroxy-4-phenyl-but-1-enyl)-6-oxo-piperidin-1-yl]-hept-5-ynoic acid isopropyl ester (Slower Eluting Diastereomer by HPLC)

The two diastereomers of example 19 (11 mg, 0.027 mmol) dissolved in EtOAc (0.75 mL) were separated on a Waters 600 HPLC instrument employing a Waters 2996 PDA detector and a Whatman Partisil® 10 column having dimensions of 22×500 mm. Using EtOAc as the eluent and a flow rate of 10 mL/min, the first diastereomer (3 mg) eluted at 40 min, and the second diastereomer (3 mg) eluted at 44 min.

EXAMPLE 50

{4-[(R)-2-Oxo-6-((E)-3-oxo-4-phenyl-but-1-enyl)-piperidin-1-yl]-butoxy}-acetic acid methyl ester (FIG. 1)

Step 1. (R)-6-(1-Ethoxyethoxymethyl)-piperidin-2-one

Ethyl vinyl ether (1.68 mL, 17.5 mmol) and trifluoroacetic acid (0.1 mL) were added sequentially to a solution of (R)-6-hydroxymethylpiperidin-2-one (prepared from D-□-aminoadipic acid according to Huang, et al., *Synth. Commun.* 1989, 19, 3485-3496, 1.62 g, 12.5 mmol) in $CHCl_3$ (10 mL) at rt. The reaction mixture was stirred at rt for 18 h, then saturated aqueous $NaHCO_3$ (100 mL) was added and the mixture was extracted with $CH_2Cl_2$ (3×75 mL). The combined organic phase was dried ($Na_2SO_4$), filtered and concentrated in vacuo. Purification of the residue by flash column chromatography on silica gel ($CH_2Cl_2$→4% MeOH/$CH_2Cl_2$, gradient) afforded 2.03 g (80%) of (R)-6-(1-ethoxyethoxymethyl)-piperidin-2-one.

Step 2. {(Z)-4-[(R)-2-(1-Ethoxyethoxymethyl)-6-oxo-piperidin-1-yl]-but-2-enyloxy}-acetic acid ethyl ester Sodium hydride (60% dispersion in oil, 402 mg, 10.0 mmol) was added to a solution of (R)-6-(1-ethoxyethoxymethyl)-piperidin-2-one (2.02 g, 10.0 mmol) in DMF (15 mL) at 0° C. After 1 h, a solution of potassium iodide (1.66 g, 10.0 mmol) and ((Z)-4-chloro-but-2-enyloxy)-acetic acid ethyl ester (prepared according to PCT 2003/007941, 3.09 g, 16.0 mmol) in DMF (10 mL) was added via cannula. The reaction was allowed to warm to rt. After 18 h at rt, the reaction was quenched by the addition of saturated aqueous $NaHCO_3$ (100 mL) and the mixture was extracted with EtOAc (3×100 mL). The combined organic phase was washed with brine (3×100 mL), dried ($Na_2SO_4$), filtered and concentrated in vacuo. Purification of the residue by flash column chromatography on silica gel (10% EtOAc/

$CH_2Cl_2$→60% EtOAc/$CH_2Cl_2$, gradient) afforded 1.10 g (31%) of {(Z)-4-[(R)-2-(1-ethoxyethoxymethyl)-6-oxo-piperidin-1-yl]-but-2-enyloxy}-acetic acid ethyl ester.

Step 3. [(Z)-4-((R)-2-Hydroxymethyl-6-oxo-piperidin-1-yl)-but-2-enyloxy]-acetic acid methyl ester p-Toluenesulfonic acid hydrate (620 mg, 3.26 mmol) was added to a solution of {(Z)-4-[(R)-2-(1-ethoxyethoxymethyl)-6-oxo-piperidin-1-yl]-but-2-enyloxy}-acetic acid ethyl ester (1.10 g, 3.08 mmol) in MeOH (10 mL). After 17 h at rt, the reaction was quenched with saturated aqueous $NaHCO_3$ (20 mL) and the mixture was extracted with $CH_2Cl_2$ (3×30 mL). The combined organic phase was dried ($Na_2SO_4$), filtered and concentrated in vacuo. Purification of the residue by flash column chromatography on silica gel (40% EtOAc/$CH_2Cl_2$→60% EtOAc/$CH_2Cl_2$, gradient, then 7% MeOH/$CH_2Cl_2$) afforded 538 mg (64%) of [(Z)-4-((R)-2-hydroxymethyl-6-oxo-piperidin-1-yl)-but-2-enyloxy]-acetic acid methyl ester.

Step 4. [4-((R)-2-Hydroxymethyl-6-oxo-piperidin-1-yl)-butoxy]-acetic acid methyl ester Palladium on carbon (10 wt. %, 25 mg) was added to a solution of [(Z)-4-((R)-2-hydroxymethyl-6-oxo-piperidin-1-yl)-but-2-enyloxy]-acetic acid methyl ester (318 mg, 1.17 mmol) in MeOH (5.0 mL). A hydrogen atmosphere was established by evacuating and refilling with hydrogen (3×) and the reaction mixture was stirred under a balloon of hydrogen for 2.25 h. The reaction mixture was filtered through celite, washing with MeOH, and the filtrate was concentrated in vacuo. Purification of the residue by flash column chromatography on silica gel (30% EtOAc/$CH_2Cl_2$→50% EtOAc/$CH_2Cl_2$, gradient, then 2% MeOH/$CH_2Cl_2$→5% MeOH/$CH_2Cl_2$) afforded 285 mg (89%) of [4-((R)-2-hydroxymethyl-6-oxo-piperidin-1-yl)-butoxy]-acetic acid methyl ester.

Step 5. [4-((R)-2-Formyl-6-oxo-piperidin-1-yl)-butoxy]-acetic acid methyl ester

A solution of oxalyl chloride (0.15 mL, 1.76 mmol) in $CH_2Cl_2$ (11.0 mL) was added to a solution of DMSO (0.16 mL, 2.25 mmol) in $CH_2Cl_2$ (1.0 mL) at −78° C. After 15 min at −78° C., a solution of [4-((R)-2-hydroxymethyl-6-oxo-piperidin-1-yl)-butoxy]-acetic acid methyl ester (240 mg, 0.88 mmol) in $CH_2Cl_2$ (1.5 mL) was added via cannula. After 20 min at −78° C., triethylamine (0.37 mL, 2.65 mmol) was added. After 20 min at −78° C., the mixture was allowed to warm to 0° C. After 30 min at 0° C., the reaction was allowed to warm to rt. After 45 min at rt, saturated aqueous $NaHCO_3$ (15 mL) was added and the mixture was extracted with $CH_2Cl_2$ (3×15 mL). The combined organic phase was dried ($Na_2SO_4$), filtered and concentrated in vacuo. Purification of the residue by flash column chromatography on silica gel (40%→70% EtOAc/$CH_2Cl_2$, gradient) afforded 96 mg (40%) of [4-((R)-2-formyl-6-oxo-piperidin-1-yl)-butoxy]-acetic acid methyl ester.

Step 6. {4-[(R)-2-Oxo-6-((E)-3-oxo-4-phenyl-but-1-enyl)-piperidin-1-yl]-butoxy}-acetic acid methyl ester Sodium hydride (60% dispersion in oil, 14 mg, 0.35 mmol) was added to a solution of dimethyl 2-oxo-3-phenylpropylphosphonate (83 mg, 0.34 mmol) in THF (1.0 mL) at 0° C. After 1 h at 0° C., [4-((R)-2-formyl-6-oxo-piperidin-1-yl)-butoxy]-acetic acid methyl ester (94 mg, 0.35 mmol) in THF (1 mL) was added via cannula. The reaction was allowed to warm to rt. After 22 h at rt, the reaction was quenched with saturated aqueous $NH_4Cl$ (10 mL) and extracted with EtOAc (3×15 mL). The combined organic phase was washed with brine (20 mL), dried ($Na_2SO_4$), filtered and concentrated in vacuo. Purification of the residue by flash column chromatography on silica gel (30%→50% EtOAc/$CH_2Cl_2$, gradient) afforded 42 mg (31%) of the title compound.

EXAMPLE 51

{4-[(R)-2-Oxo-6-((E)-3-oxo-4-phenyl-but-1-enyl)-piperidin-1-yl]-butoxy}-acetic acid In accordance with the procedure of example 2, {4-[(R)-2-oxo-6-((E)-3-oxo-4-phenyl-but-1-enyl)-piperidin-1-yl]-butoxy}-acetic acid methyl ester (10 mg, 0.026 mmol) was converted into 7.7 mg (80%) of the title compound.

EXAMPLE 52

{4-[(R)-2-((E)-3-Hydroxy-4-phenyl-but-1-enyl)-6-oxo-piperidin-1-yl]-butoxy}-acetic acid methyl ester Sodium borohydride (4 mg, 0.11 mmol), followed by MeOH (0.25 mL), was added to a solution of {4-[(R)-2-oxo-6-((E)-3-oxo-4-phenyl-but-1-enyl)-piperidin-1-yl]-butoxy}-acetic acid methyl ester (28 mg, 0.072 mmol) in $CH_2Cl_2$ (0.75 mL) at 0° C. The mixture was allowed to warm to rt. After 40 min at rt, the reaction was quenched with aqueous HCl (0.5 M) and extracted with EtOAc (3×7 mL). The combined organic phase was dried ($Na_2SO_4$), filtered and concentrated in vacuo to afford 22 mg (78%) of the title compound.

EXAMPLE 53

{4-[(R)-2-((E)-3-Hydroxy-4-phenyl-but-1-enyl)-6-oxo-piperidin-1-yl]-butoxy}-acetic acid In accordance with the procedure of example 2, {4-[(R)-2-((E)-3-hydroxy-4-phenyl-but-1-enyl)-6-oxo-piperidin-1-yl]-butoxy}-acetic acid methyl ester (12.6 mg, 0.032 mmol) was converted into 10.5 mg (86%) of the title compound.

EXAMPLE 54

{4-[(R)-2-(3-Hydroxy-4-phenyl-butyl)-6-oxo-piperidin-1-yl]-butoxy}-acetic acid methyl ester Palladium on carbon (10 wt. %, 3 mg) was added to a solution of {4-[(R)-2-((E)-3-hydroxy-4-phenyl-but-1-enyl)-6-oxo-piperidin-1-yl]-butoxy}-acetic acid methyl ester (9.5 mg, 0.024 mmol) in MeOH (2.0 mL). A hydrogen atmosphere was established by evacuating and refilling with hydrogen (3×) and the reaction mixture was stirred under a balloon of hydrogen for 4 h. The reaction mixture was filtered through celite, washing with MeOH, and the filtrate was concentrated in vacuo to afford 8.2 mg (86%) of the title compound.

EXAMPLE 55

{4-[(R)-2-(3-Hydroxy-4-phenyl-butyl)-6-oxo-piperidin-1-yl]-butoxy}-acetic acid

In accordance with the procedure of example 2, {4-[(R)-2-(3-hydroxy-4-phenyl-butyl)-6-oxo-piperidin-1-yl]-butoxy}-acetic acid methyl ester (7.2 mg, 0.018 mmol) was converted into 6.9 mg (99%) of the title compound.

EXAMPLE 56

(Z)-4-[(R)-2-Oxo-6-((E)-3-oxo-4-phenyl-but-1-enyl)-piperidin-1-yl-but-2-enyloxy]-acetic acid methyl ester (FIG. 2)

Step 1. [(Z)-4-((R)-2-Formyl-6-oxo-piperidin-1-yl)-but-2-enyloxy]-acetic acid methyl ester Trifluoroacetic anhydride (0.24 mL, 1.70 mmol) was added to a solution of DMSO (0.14 mL, 1.97 mmol) in $CH_2Cl_2$ (2 mL) at −78° C. After 15 min at −78° C., a solution of [(Z)-4-((R)-2-hydroxymethyl-6-oxo-piperidin-1-yl)-but-2-enyloxy]-acetic acid methyl ester (from example 1, step 3, 220 mg, 0.81 mmol) in $CH_2Cl_2$ (1.5 mL) was added via cannula. After 20 min at −78° C., triethylamine (0.33 mL, 2.37 mmol) was added and the reaction mixture was allowed to warm to rt. After 1 h at rt, the reaction was quenched with saturated aqueous $NH_4Cl$ (15 mL) and the mixture was extracted with $CH_2Cl_2$ (3×15 mL). The combined organic phase was dried ($Na_2SO_4$), filtered and concentrated in vacuo. Purification of the residue by flash column chromatography on silica gel (10%→50% EtOAc/$CH_2Cl_2$, gradient) afforded 150 mg (69%) of [(Z)-4-((R)-2-formyl-6-oxo-piperidin-1-yl)-but-2-enyloxy]-acetic acid methyl ester.

Step 2. {(Z)-4-[(R)-2-Oxo-6-((E)-3-oxo-4-phenyl-but-1-enyl)-piperidin-1-yl]-but-2-enyloxy}-acetic acid methyl ester Sodium hydride (60% dispersion in oil, 22 mg, 0.55 mmol) was added to a solution of dimethyl 2-oxo-3-phenylpropylphosphonate (135 mg, 0.56 mmol) in THF (1.0 mL) at 0° C. After 1 h at 0° C., [(Z)-4-((R)-2-formyl-6-oxo-piperidin-1-yl)-but-2-enyloxy]-acetic acid methyl ester (150 mg, 0.56 mmol) in THF (1 mL) was added via cannula. The reaction was allowed to warm to rt. After 16.5 h at rt, the reaction was quenched with saturated aqueous $NH_4Cl$ (15 mL) and extracted with EtOAc (3×15 mL). The combined organic phase was washed with brine (20 mL), dried ($Na_2SO_4$), filtered and concentrated in vacuo. Purification of the residue by flash column chromatography on silica gel (30%→60% EtOAc/$CH_2Cl_2$, gradient) afforded 91 mg (42%) of the title compound.

EXAMPLE 57

{(Z)-4-[(R)-2-Oxo-6-((E)-3-oxo-4-phenyl-but-1-enyl)-piperidin-1-yl]-but-2-enyloxy}-acetic acid In accordance with the procedure of example 2, {(Z)-4-[(R)-2-oxo-6-((E)-3-oxo-4-phenyl-but-1-enyl)-piperidin-1-yl]-but-2-enyloxy}-acetic acid methyl ester (6.3 mg, 0.016 mmol) was converted into 1.9 mg (31%) of the title compound.

EXAMPLE 58

{4-[(R)-2-Oxo-6-(3-oxo-4-phenyl-butyl)-piperidin-1-yl]-butoxy}-acetic acid methyl ester Palladium on carbon (10 wt. %, 2 mg) was added to a solution of {(Z)-4-[(R)-2-oxo-6-((E)-3-oxo-4-phenyl-but-1-enyl)-piperidin-1-yl]-but-2-enyloxy}-acetic acid methyl ester (9.7 mg, 0.025 mmol) in MeOH (1.5 mL). A hydrogen atmosphere was established by evacuating and refilling with hydrogen (3×) and the reaction mixture was stirred under a balloon of hydrogen for 19 h. The reaction mixture was filtered through celite, washing with MeOH, and the filtrate was concentrated in vacuo to afford 8.3 mg (85%) of the title compound.

EXAMPLE 59

{4-[(R)-2-Oxo-6-(3-oxo-4-phenyl-butyl)-piperidin-1-yl]-butoxy}-acetic acid

In accordance with the procedure of example 2, 4-[(R)-2-oxo-6-(3-oxo-4-phenyl-butyl)-piperidin-1-yl]-butoxy}-acetic acid methyl ester (6.9 mg, 0.018 mmol) was converted into 6.2 mg (93%) of the title compound.

EXAMPLE 60

{(Z)-4-[(R)-2-((E)-3-Hydroxy-4-phenyl-but-1-enyl)-6-oxo-piperidin-1-yl]-but-2-enyloxy}-acetic acid methyl ester Sodium borohydride (4 mg, 0.11 mmol), followed by MeOH (0.25 mL), was added to a solution of {(Z)-4-[(R)-2-oxo-6-((E)-3-oxo-4-phenyl-but-1-enyl)-piperidin-1-yl]-but-2-enyloxy}-acetic acid methyl ester (28 mg, 0.073 mmol) in $CH_2Cl_2$ (0.75 mL) at 0° C. The mixture was allowed to warm to rt. After 1 h at rt, the reaction was quenched with aqueous HCl (0.5 M) and extracted with EtOAc (3×10 mL). The combined organic phase was dried ($Na_2SO_4$), filtered and concentrated in vacuo to afford 22 mg (78%) of the title compound.

EXAMPLE 61

{(Z)-4-[(R)-2-((E)-3-Hydroxy-4-phenyl-but-1-enyl)-6-oxo-piperidin-1-yl]-but-2-enyloxy}-acetic acid In accordance with the procedure of example 2, {(Z)-4-[(R)-2-((E)-3-hydroxy-4-phenyl-but-1-enyl)-6-oxo-piperidin-1-yl]-but-2-enyloxy}-acetic acid methyl ester (17.7 mg, 0.046 mmol) was converted into 17 mg (99%) of the title compound.

EXAMPLE 62

{(Z)-4-[(R)-2-Oxo-6-(3-oxo-4-phenyl-butyl)-piperidin-1-yl]-but-2-enyloxy}-acetic acid methyl ester A solution of {(Z)-4-[(R)-2-oxo-6-((E)-3-oxo-4-phenyl-but-1-enyl)-piperidin-1-yl]-but-2-enyloxy}-acetic acid methyl ester (24.6 mg, 0.064 mmol) in $CH_3CN$ (1.5 mL) was added via cannula to hydrido(triphenylphosphine)copper(I) hexamer (125 mg, 0.064 mmol) at −40° C. After 1 h at −40° C., the reaction was allowed to warm to rt. After 3 h at rt, the reaction was quenched by addition of a solution of $NH_4OH$ and saturated aqueous $NH_4Cl$ (1:1, 6 mL). The mixture was extracted with EtOAc (3×10 mL). The combined organic phase was washed with brine (20 mL), dried ($Na_2SO_4$), filtered and concentrated in vacuo. Purification of the residue by flash column chromatography on silica gel (20%→70% EtOAc/$CH_2Cl_2$, gradient) afforded 19.6 mg (79%) of the title compound.

EXAMPLE 63

{(Z)-4-[(R)-2-Oxo-6-(3-oxo-4-phenyl-butyl)-piperidin-1-yl]-but-2-enyloxy}-acetic acid In accordance with the procedure of example 2, {(Z)-4-[(R)-2-oxo-6-(3-oxo-4-phenyl-butyl)-piperidin-1-yl]-but-2-enyloxy}-acetic acid methyl ester (6.1 mg, 0.016 mmol) was converted into 1.7 mg (29%) of the title compound.

EXAMPLE 64

{(Z)-4-[(R)-2-(3-Hydroxy-4-phenyl-butyl)-6-oxo-piperidin-1-yl]-but-2-enyloxy}-acetic acid methyl ester Sodium borohydride (2 mg, 0.053 mmol), followed by MeOH (0.15 mL), was added to a solution of {(Z)-4-[(R)-2-oxo-6-(3-oxo-4-phenyl-butyl)-piperidin-1-yl]-but-2-enyloxy}-acetic acid methyl ester (11.5 mg, 0.030 mmol) in $CH_2Cl_2$ (0.5 mL) at 0° C. The mixture was allowed to warm to rt. After 30 min at rt, the reaction was quenched with aqueous HCl (0.5 M) and extracted with EtOAc (3×7 mL). The combined organic phase was dried ($Na_2SO_4$), filtered and concentrated in vacuo to afford 10.1 mg (87%) of the title compound.

EXAMPLE 65

{(Z)-4-[(R)-2-(3-Hydroxy-4-phenyl-butyl)-6-oxo-piperidin-1-yl]-but-2-enyloxy}-acetic acid In accordance with the procedure of example 2, {(Z)-4-[(R)-2-(3-hydroxy-4-phenyl-butyl)-6-oxo-piperidin-1-yl]-but-2-enyloxy}-acetic acid methyl ester (6.2 mg, 0.016 mmol) was converted into 1.6 mg (27%) of the title compound.

EXAMPLE 66

(4-{(R)-2-[(E)-4-(3-Chlorophenyl)-3-hydroxy-but-1-enyl]-6-oxo-piperidin-1-yl}-butoxy)-acetic acid (FIG. 3)

Step 1. [(Z)-4-((R)-2-Hydroxymethyl-6-oxo-piperidin-1-yl)-but-2-enyloxy]-acetic acid ethyl ester p-Toluenesulfonic acid hydrate (267 mg, 1.40 mmol) was added to a solution of {(Z)-4-[(R)-2-(1-ethoxyethoxymethyl)-6-oxo-piperidin-1-yl]-but-2-enyloxy}-acetic acid ethyl ester (from example 50, step 2, 477 mg, 1.33 mmol) in EtOH (6 mL). After 18 h at rt, the reaction was concentrated in vacuo and quenched with saturated aqueous $NaHCO_3$ (20 mL). The mixture was extracted with $CH_2Cl_2$ (3×15 mL). The combined organic phase was dried ($Na_2SO_4$), filtered and concentrated in vacuo. Purification of the residue by flash column chromatography on silica gel ($CH_2Cl_2$→3% MeOH/$CH_2Cl_2$, gradient) afforded 290 mg (76%) of [(Z)-4-((R)-2-hydroxymethyl-6-oxo-piperidin-1-yl)-but-2-enyloxy]-acetic acid ethyl ester.

Step 2. [4-((R)-2-Hydroxymethyl-6-oxo-piperidin-1-yl)-butoxy]-acetic acid ethyl ester Palladium on carbon (10 wt. %, 15 mg) was added to a solution of [(Z)-4-((R)-2-hydroxymethyl-6-oxo-piperidin-1-yl)-but-2-enyloxy]-acetic acid ethyl ester (290 mg, 1.02 mmol) in EtOH (3.0 mL). A hydrogen atmosphere was established by evacuating and refilling with hydrogen (3×) and the reaction mixture was stirred under a balloon of hydrogen for 3 h. The reaction mixture was filtered through celite, washing with EtOH, and the filtrate was concentrated in vacuo to afford 295 mg (quant. crude) of [4-((R)-2-hydroxymethyl-6-oxo-piperidin-1-yl)-butoxy]-acetic acid ethyl ester.

Step 3. [4-((R)-2-Formyl-6-oxo-piperidin-1-yl)-butoxy]-acetic acid ethyl ester 1-(3-(Dimethylaminopropyl)-3-ethylcarbodiimide hydrochloride (EDCI, 505 mg, 2.63 mmol) and DMSO (0.25 mL, 3.52 mmol) were added sequentially to a solution of [4-((R)-2-hydroxymethyl-6-oxo-piperidin-1-yl)-butoxy]-acetic acid ethyl ester (252 mg, 0.88 mmol) in benzene (5 mL). The mixture was cooled to 0° C. and pyridinium trifluoroacetate (187 mg, 0.97 mmol) was added. The reaction was allowed to warm to rt and then was stirred at rt for 4.25 h. The solution was decanted from the oily residue and the residue was washed with benzene (3×5 mL). The combined benzene phases were concentrated in vacuo to afford crude 4-((R)-2-formyl-6-oxo-piperidin-1-yl)-butoxy]-acetic acid ethyl ester that was used without further purification.

Step 4. (4-{(R)-2-[(E)-4-(3-Chlorophenyl)-3-oxo-but-1-enyl]-6-oxo-piperidin-1-yl}-butoxy)-acetic acid ethyl ester Sodium hydride (60% dispersion in oil, 35 mg, 0.88 mmol) was added to a solution of [3-(3-chlorophenyl)-2-oxopropyl]-phosphonic acid dimethyl ester (221 mg, 0.80 mmol) in THF (2.0 mL) at 0° C. After 1 h at 0° C., [4-((R)-2-formyl-6-oxo-piperidin-1-yl)-butoxy]-acetic acid ethyl ester (0.88 mmol, crude) in THF (2 mL) was added via cannula. The reaction was allowed to warm to rt. After 18 h at rt, the reaction was quenched with aqueous acetic acid (50%, 10 mL) and extracted with EtOAc (3×20 mL). The combined organic phase was washed with brine (25 mL), dried ($Na_2SO_4$), filtered and concentrated in vacuo. Purification of the residue by flash column chromatography on silica gel (20%→40% EtOAc/$CH_2Cl_2$, gradient) afforded 117 mg (34%) of (4-{(R)-2-[(E)-4-(3-chlorophenyl)-3-oxo-but-1-enyl]-6-oxo-piperidin-1-yl}-butoxy)-acetic acid ethyl ester.

Step 5. (4-{(R)-2-[(E)-4-(3-Chlorophenyl)-3-hydroxy-but-1-enyl]-6-oxo-piperidin-1-yl}-butoxy)-acetic acid ethyl ester Sodium borohydride (10 mg, 0.26 mmol) followed by EtOH (0.25 mL) was added to a solution of (4-{(R)-2-[(E)-4-(3-chlorophenyl)-3-oxo-but-1-enyl]-6-oxo-piperidin-1-yl}-butoxy)-acetic acid ethyl ester (110 mg, 0.25 mmol) in $CH_2Cl_2$ (1.0 mL) at 0° C. After 1 h at 0° C. the reaction was quenched with 1 N aqueous HCl. The reaction mixture was extracted with $CH_2Cl_2$ (3×10 mL), then the combined extracts were dried ($Na_2SO_4$), filtered and concentrated in vacuo. Purification of the residue by flash column chromatography on silica gel ($CH_2Cl_2$→2% MeOH/$CH_2Cl_2$)

afforded 88 mg (80%) of (4-{(R)-2-[(E)-4-(3-chlorophenyl)-3-hydroxy-but-1-enyl]-6-oxo-piperidin-1-yl}-butoxy)-acetic acid ethyl ester.

Step 6. (4-{(R)-2-[(E)-4-(3-Chlorophenyl)-3-hydroxy-but-1-enyl]-6-oxo-piperidin-1-yl}-butoxy)-acetic acid In accordance with the procedure of example 2, (4-{(R)-2-[(E)-4-(3-chlorophenyl)-3-hydroxy-but-1-enyl]-6-oxo-piperidin-1-yl}-butoxy)-acetic acid ethyl ester (88 mg, 0.20 mmol) was converted into 44 mg (54%) of the title compound.

EXAMPLE 67

2-(4-{(R)-2-[(E)-4-(3-Chlorophenyl)-3-hydroxy-but-1-enyl]-6-oxo-piperidin-1-yl}-butoxy)-acetamide Triethylamine (8.8 μL, 0.063 mmol) was added to a solution of (4-{(R)-2-[(E)-4-(3-chlorophenyl)-3-hydroxy-but-1-enyl]-6-oxo-piperidin-1-yl}-butoxy)-acetic acid (12.4 mg, 0.030 mmol) in $CH_2Cl_2$ (0.2 mL). After cooling to 0° C., the reaction mixture was treated with ethyl chloroformate (3.2 μL, 0.033 mmol). After 1 h at 0° C., ammonia (0.5 M in 1,4-dioxane, 0.32 mL, 0.16 mmol) was added and the reaction mixture was allowed to warm to rt. After 18 h at rt, the reaction mixture was treated with saturated aqueous $NaHCO_3$ (5 mL) and extracted with $CH_2Cl_2$ (3×5 mL). The combined extracts were dried ($Na_2SO_4$), filtered and concentrated in vacuo. Purification of the residue by flash column chromatography on silica gel (5%→20% MeOH/$CH_2Cl_2$, gradient) afforded 1.3 mg (11%) of the title compound.

EXAMPLE 68

(4-{(R)-2-[(E)-4-(3-Chlorophenyl)-3-hydroxy-but-1-enyl]-6-oxo-piperidin-1-yl}-butoxy)-acetic acid isopropyl ester 1,8-Diazabicyclo[5.4.0]undec-7-ene (DBU, 16 μL, 0.11 mmol) was added to a solution of (4-{(R)-2-[(E)-4-(3-chlorophenyl)-3-hydroxy-but-1-enyl]-6-oxo-piperidin-1-yl}-butoxy)-acetic acid (29 mg, 0.071 mmol) in acetone (0.5 mL). After 5 min, 2-iodopropane (35 μL, 0.35 mmol) was added. After 17 h, the reaction mixture was concentrated in vacuo, EtOAc (15 mL) was added and the resultant mixture was washed with 0.5 M aqueous HCl (5 mL), saturated aqueous $NaHCO_3$ (5 mL) and brine (5 mL). The organic phase was then dried ($Na_2SO_4$), filtered and concentrated in vacuo. Purification of the residue by flash column chromatography on silica gel ($CH_2Cl_2$<5% MeOH/$CH_2Cl_2$, gradient) afforded 16 mg (50%) of the title compound.

EXAMPLE 69

(4-{(R)-2-[(E)-4-(3-Chlorophenyl)-3-oxo-but-1-enyl]-6-oxo-piperidin-1-yl}-but-2-ynyloxy)-acetic acid methyl ester Step 1. (4-Hydroxy-but-2-ynyloxy)-acetic acid methyl ester Sodium hydride (60% dispersion in oil, 2.32 g, 58 mmol) was added to a solution of 2-butyne-1,4-diol (5.0 g, 58 mmol) in THF (60 mL) at 0° C. under nitrogen. After 1 h at 0° C., methyl bromomethylacetate (5.5 mL, 58 mmol) was added and the reaction was allowed to warm to rt. After 18 h at rt, the reaction was quenched with 1 N HCl (60 mL) and extracted with EtOAc (3×100 mL). The combined extracts were washed with brine (1×100 mL), dried ($MgSO_4$), filtered and concentrated in vacuo. Purification of the residue by flash column chromatography on silica gel ($CH_2Cl_2$→5% MeOH/$CH_2Cl_2$, gradient) afforded 3.2 g (35%) of (4-hydroxy-but-2-ynyloxy)-acetic acid methyl ester.

Step 2. (4-Iodo-but-2-ynyloxy)-acetic acid methyl ester

Triphenylphosphine (6.23 g, 23.8 mmol), iodine (6.03 g, 23.8 mmol) and imidazole (1.57 g, 23.8 mmol) were added sequentially to a solution of (4-hydroxy-but-2-ynyloxy)-acetic acid methyl ester (3.13 g, 19.8 mmol) in $CH_2Cl_2$ (30 mL). After 1 h at rt, the reaction was filtered through activity I basic alumina, washing with 20% EtOAc/Hexane. The filtrate was concentrated in vacuo then purified by flash column chromatography on silica gel (Hexane→20% EtOAc/Hexane, gradient) to afford 2.05 g (39%) of (4-iodo-but-2-ynyloxy)-acetic acid methyl ester.

Step 3. {4-[(R)-2-(1-Ethoxy-ethoxymethyl)-6-oxo-piperidin-1-yl]-but-2-ynyloxy}-acetic acid methyl ester Sodium hydride (60% dispersion in oil, 278 mg, 6.95 mmol) was added to a solution of (R)-6-(1-ethoxyethoxymethyl)-piperidin-2-one (from example 50, step 1, 1.40 g, 6.96 mmol) in DMF (10 mL) at 0° C. After 1 h at 0° C., (4-iodo-but-2-ynyloxy)-acetic acid methyl ester (2.05 g, 7.65 mmol) in DMF (10 mL) was added via cannula and the reaction was allowed to warm to rt. After 15 min at rt, the reaction mixture solidified, so more DMF (3 mL) was added. After 18 h at rt, the reaction was treated with saturated aqueous $NaHCO_3$ (50 mL) and extracted with EtOAc (3×70 mL). The combined extracts were washed with water (2×50 mL) and brine (2×50 mL) then dried ($MgSO_4$), filtered and concentrated in vacuo. Purification of the residue by flash column chromatography on silica gel (20%→50% EtOAc/$CH_2Cl_2$, gradient) afforded 500 mg (21%) of {4-[(R)-2-(1-ethoxy-ethoxymethyl)-6-oxo-piperidin-1-yl]-but-2-ynyloxy}-acetic acid methyl ester.

Step 4. [4-((R)-2-Hydroxymethyl-6-oxo-piperidin-1-yl)-but-2-ynyloxy]-acetic acid methyl ester p-Toluenesulfonic acid hydrate (289 mg, 1.52 mmol) was added to a solution of {4-[(R)-2-(1-ethoxy-ethoxymethyl)-6-oxo-piperidin-1-yl]-but-2-ynyloxy}-acetic acid methyl ester (494 mg, 1.45 mmol) in MeOH (5.0 mL) at rt. After 20 h at rt, the mixture was concentrated in vacuo, treated with saturated aqueous $NaHCO_3$ (20 mL) and extracted with $CH_2Cl_2$ (3×20 mL). The combined organic phase was dried ($MgSO_4$), filtered and concentrated in vacuo. Purification of the residue by flash column chromatography on silica gel ($CH_2Cl_2$→3% MeOH/$CH_2Cl_2$, gradient) afforded 100 mg (26%) of [4-((R)-2-hydroxymethyl-6-oxo-piperidin-1-yl)-but-2-ynyloxy]-acetic acid methyl ester.

Step 5. [4-((R)-2-Formyl-6-oxo-piperidin-1-yl)-but-2-ynyloxy]-acetic acid methyl ester EDCI (214 mg, 1.12 mmol) was added to a solution of [4-((R)-2-hydroxymethyl-6-oxo-piperidin-1-yl)-but-2-ynyloxy]-acetic acid methyl ester (100 mg, 0.37 mmol) in benzene (3.5 mL). The reaction mixture was cooled to 0° C. and DMSO (0.11 mL, 1.55 mmol) was added. After 5 min at 0° C., pyridinium trifluoroacetate (79 mg, 0.41 mmol) was added. The reaction was allowed to warm to rt and then was stirred at rt for 3 h. The solution was decanted from the oily residue and the residue was washed with benzene (3×3 mL). The combined benzene phases were concentrated in vacuo to afford crude [4-((R)-2-formyl-6-oxo-piperidin-1-yl)-but-2-ynyloxy]-acetic acid methyl ester, which was used without further purification.

Step 6. (4-{(R)-2-[(E)-4-(3-Chlorophenyl)-3-oxo-but-1-enyl]-6-oxo-piperidin-1-yl}-but-2-ynyloxy)-acetic acid methyl ester Sodium hydride (60% dispersion in oil, 15 mg, 0.39 mmol) was added to a solution of [3-(3-chlorophenyl)-2-oxopropyl]-phosphonic acid dimethyl ester (97 mg, 0.35 mmol) in THF (1.5 mL) at 0° C. After 1 h at 0° C., a solution of [4-((R)-2-formyl-6-oxo-piperidin-1-yl)-but-2-ynyloxy]-acetic acid methyl ester (0.37 mmol, crude) in THF (1.5 mL) was added via cannula. The reaction was allowed to warm to rt. After 18 h at rt, the reaction was quenched with aqueous acetic acid (50%, 15 mL) and extracted with EtOAc (3×15 mL). The combined organic phase was washed with brine (20 mL), dried ($MgSO_4$), filtered and concentrated in vacuo. Purification of the residue by flash column chromatography on silica gel (20%→30% $EtOAc/CH_2Cl_2$, gradient) afforded 100 mg (68%) of the title compound.

EXAMPLE 70

(4-{(R)-2-[(E)-4-(3-Chlorophenyl)-3-oxo-but-1-enyl]-6-oxo-piperidin-1-yl}-but-2-ynyloxy)-acetic acid In accordance with the procedure of example 2, (4-{(R)-2-[(E)-4-(3-chlorophenyl)-3-oxo-but-1-enyl]-6-oxo-piperidin-1-yl}-but-2-ynyloxy)-acetic acid methyl ester (8.0 mg, 0.019 mmol) was converted into 7.0 mg (91%) of the title compound.

EXAMPLES 71 AND 72

(4-{(R)-2-[(E)-4-(3-Chlorophenyl)-3-hydroxy-but-1-enyl]-6-oxo-piperidin-1-yl}-but-2-ynyloxy)-acetic acid methyl ester and (R)-6-[(E)-4-(3-Chlorophenyl)-3-hydroxy-but-1-enyl]-1-[4-(2-hydroxyethoxy)-but-2-ynyl]-piperidin-2-one Sodium borohydride (5 mg, 0.13 mmol) followed by MeOH (0.5 mL) was added to a solution of (4-{(R)-2-[(E)-4-(3-chlorophenyl)-3-oxo-but-1-enyl]-6-oxo-piperidin-1-yl}-but-2-ynyloxy)-acetic acid methyl ester (48 mg, 0.11 mmol) in $CH_2Cl_2$ (1.0 mL) at 0° C. After 20 min at 0° C. the reaction was quenched with 0.5 N aqueous HCl. The reaction mixture was extracted with $CH_2Cl_2$ (3×10 mL), then the combined extracts were dried ($MgSO_4$), filtered and concentrated in vacuo. Purification of the residue by flash column chromatography on silica gel ($CH_2Cl_2$→2% MeOH/$CH_2Cl_2$) followed by preparative thin layer chromatography (5% $MeOH/CH_2Cl_2$) afforded 22 mg (46%) of (4-{(R)-2-[(E)-4-(3-chlorophenyl)-3-hydroxy-but-1-enyl]-6-oxo-piperidin-1-yl}-but-2-ynyloxy)-acetic acid methyl ester and 1.7 mg (4%) of (R)-6-[(E)-4-(3-chlorophenyl)-3-hydroxy-but-1-enyl]-1-[4-(2-hydroxyethoxy)-but-2-ynyl]-piperidin-2-one.

EXAMPLE 73

(4-{(R)-2-[(E)-4-(3-Chlorophenyl)-3-hydroxy-but-1-enyl]-6-oxo-piperidin-1-yl}-but-2-ynyloxy)-acetic acid In accordance with the procedure of example 2, (4-{(R)-2-[(E)-4-(3-chlorophenyl)-3-hydroxy-but-1-enyl]-6-oxo-piperidin-1-yl}-but-2-ynyloxy)-acetic acid methyl ester (18 mg, 0.043 mmol) was converted into 15.6 mg (90%) of the title compound.

EXAMPLE 74

(4-{(R)-2-[(E)-4-(3-Chlorophenyl)-3-hydroxy-but-1-enyl]-6-oxo-piperidin-1-yl}-but-2-ynyloxy)-acetic acid isopropyl ester DBU (6.6 μL, 0.044 mmol) was added to a solution of (4-{(R)-2-[(E)-4-(3-chlorophenyl)-3-hydroxy-but-1-enyl]-6-oxo-piperidin-1-yl}-but-2-ynyloxy)-acetic acid (12 mg, 0.030 mmol) in acetone (0.3 mL). After 5 min, 2-iodopropane (15 μL, 0.15 mmol) was added. After 19 h, the reaction mixture was concentrated in vacuo, 0.5 M aqueous HCl (5 mL) was added and the mixture was extracted with EtOAc (3×5 mL). The combine organic phase was washed with saturated aqueous $NaHCO_3$ (10 mL) and brine (10 mL) then dried ($MgSO_4$), filtered and concentrated in vacuo. Purification of the residue by flash column chromatography on silica gel ($CH_2Cl_2$→3% $MeOH/CH_2Cl_2$, gradient) afforded 7.9 mg (60%) of the title compound.

EXAMPLE 75

(4-{(R)-2-[4-(3-Chlorophenyl)-3-oxo-butyl]-6-oxo-piperidin-1-yl}-but-2-ynyloxy)-acetic acid methyl ester A solution of (4-{(R)-2-[(E)-4-(3-chlorophenyl)-3-oxo-but-1-enyl]-6-oxo-piperidin-1-yl}-but-2-ynyloxy)-acetic acid methyl ester (35 mg, 0.084 mmol) in toluene (2 mL) was added via cannula to a round-bottomed flask containing hydrido(triphenylphosphine)copper(I) hexamer (164 mg, 0.084 mmol) at −40° C. under nitrogen. The reaction was allowed to warm to rt and stirred for 3 h. The reaction was quenched with $NH_4OH/NH_4Cl$ (1:1, 5 mL) and extracted with EtOAc (3×7 mL). The combined extracts were dried ($MgSO_4$), filtered and concentrated in vacuo. Purification of the residue by flash column chromatography on silica gel (20%→50% $EtOAc/CH_2Cl_2$, gradient) followed by preparative thin layer chromatography (silica, 80% $EtOAc/CH_2Cl_2$) afforded 12 mg (34%) of the title compound.

EXAMPLE 76

(4-{(R)-2-[4-(3-Chlorophenyl)-3-oxo-butyl]-6-oxo-piperidin-1-yl}-but-2-ynyloxy)-acetic acid In accordance with the procedure of example 2, (4-{(R)-2-[4-(3-chlorophenyl)-3-oxo-butyl]-6-oxo-piperidin-1-yl}-but-2-ynyloxy)-acetic acid methyl ester (4.7 mg, 0.01 mmol) was converted into 2.8 mg (62%) of the title compound.

EXAMPLE 77

(4-{(R)-2-[4-(3-Chlorophenyl)-3-hydroxy-butyl]-6-oxo-piperidin-1-yl}-but-2-ynyloxy)-acetic acid methyl ester Sodium borohydride (2 mg, 0.053 mmol) followed by MeOH (0.1 mL) was added to a solution of (4-{(R)-2-[4-(3-chlorophenyl)-3-oxo-butyl]-6-oxo-piperidin-1-yl}-but-2-ynyloxy)-acetic acid methyl ester (5 mg, 0.012 mmol) in $CH_2Cl_2$ (0.3 mL) at 0° C. After 10 min at 0° C. the reaction was quenched with aqueous HCl (0.25 M, 3 mL). The reaction mixture was extracted with $CH_2Cl_2$ (3×4 mL), then the combined extracts were dried ($MgSO_4$), filtered and concentrated in vacuo. Purification of the residue by flash column chromatography on silica gel ($CH_2Cl_2$→2% MeOH/$CH_2Cl_2$) afforded 4.6 mg (92%) of the title compound.

EXAMPLE 78

(4-{(R)-2-[4-(3-Chlorophenyl)-3-hydroxy-butyl]-6-oxo-piperidin-1-yl}-but-2-ynyloxy)-acetic acid In accordance with the procedure of example 2, (4-{(R)-2-[4-(3-chlorophenyl)-3-hydroxy-butyl]-6-oxo-piperidin-1-yl}-but-2-ynyloxy)-acetic acid methyl ester (3.5 mg, 0.0083 mmol) was converted into 1.5 mg (44%) of the title compound.

EXAMPLE 79

{4-[(R)-2-Oxo-6-((E)-3-oxo-4-phenyl-but-1-enyl)-piperidin-1-yl]-but-2-ynyloxy}-acetic acid methyl ester Sodium hydride (60% dispersion in oil, 41 mg, 1.03 mmol) was added to a solution of dimethyl 2-oxo-3-phenylpropylphosphonate (247 mg, 1.02 mmol) in THF (4 mL) at 0° C. After 1 h at 0° C., a solution of [4-((R)-2-formyl-6-oxo-piperidin-1-yl)-but-2-ynyloxy]-acetic acid methyl ester (1.23 mmol, crude, prepared as in Example 69, step 4) in THF (3 mL) was added via cannula. The reaction was allowed to warm to rt. After 18 h at rt, the reaction was quenched with aqueous acetic acid (50%, 30 mL) and extracted with EtOAc (3×40 mL). The combined organic phase was washed with brine (50 mL), dried ($Na_2SO_4$), filtered and concentrated in vacuo. Purification of the residue by flash column chromatography on silica gel (30%→50% EtOAc/$CH_2Cl_2$, gradient) afforded 122 mg (31%) of the title compound.

EXAMPLE 80

{4-[(R)-2-Oxo-6-((E)-3-oxo-4-phenyl-but-1-enyl)-piperidin-1-yl]-but-2-ynyloxy}-acetic acid In accordance with the procedure of example 2, {4-[(R)-2-oxo-6-((E)-3-oxo-4-phenyl-but-1-enyl)-piperidin-1-yl]-but-2-ynyloxy}-acetic acid methyl ester (6.8 mg, 0.018 mmol) was converted into 1.1 mg (17%) of the title compound.

EXAMPLES 81 AND 82

{4-[(R)-2-((E)-3-Hydroxy-4-phenyl-but-1-enyl)-6-oxo-piperidin-1-yl]-but-2-ynyloxy}-acetic acid methyl ester and (R)-1-[4-(2-hydroxy-ethoxy)-but-2-ynyl]-6-((E)-3-hydroxy-4-phenyl-but-1-enyl)-piperidin-2-one Sodium borohydride (24 mg, 0.63 mmol) followed by MeOH (1 mL) was added to a solution of {4-[(R)-2-oxo-6-((E)-3-oxo-4-phenyl-but-1-enyl)-piperidin-1-yl]-but-2-ynyloxy}-acetic acid methyl ester (82 mg, 0.21 mmol) in $CH_2Cl_2$ (2 mL) at 0° C. After 5 min at 0° C. the reaction was quenched with aqueous HCl (0.2 M, 10 mL). The reaction mixture was extracted with $CH_2Cl_2$ (3×10 mL), then the combined extracts were dried ($Na_2SO_4$), filtered and concentrated in vacuo. Purification of the residue by flash column chromatography on silica gel ($CH_2Cl_2$→3% MeOH/$CH_2Cl_2$) afforded 56.5 mg (69%) of {4-[(R)-2-((E)-3-hydroxy-4-phenyl-but-1-enyl)-6-oxo-piperidin-1-yl]-but-2-ynyloxy}-acetic acid methyl ester and 11 mg (14%) of (R)-1-[4-(2-hydroxy-ethoxy)-but-2-ynyl]-6-((E)-3-hydroxy-4-phenyl-but-1-enyl)-piperidin-2-one.

EXAMPLE 83

{4-[(R)-2-((E)-3-Hydroxy-4-phenyl-but-1-enyl)-6-oxo-piperidin-1-yl]-but-2-ynyloxy}-acetic acid In accordance with the procedure of example 2, {4-[(R)-2-((E)-3-hydroxy-4-phenyl-but-1-enyl)-6-oxo-piperidin-1-yl]-but-2-ynyloxy}-acetic acid methyl ester (54.4 mg, 0.14 mmol) was converted into 31 mg (59%) of the title compound

EXAMPLE 84

{4-[(R)-2-((E)-3-Hydroxy-4-phenyl-but-1-enyl)-6-oxo-piperidin-1-yl]-but-2-ynyloxy}-acetic acid isopropyl ester DBU (10 μL, 0.067 mmol) was added to a solution of {4-[(R)-2-((E)-3-hydroxy-4-phenyl-but-1-enyl)-6-oxo-piperidin-1-yl]-but-2-ynyloxy}-acetic acid (16.6 mg, 0.045 mmol) in acetone (0.5 mL). After 5 min, 2-iodopropane (22.5 μL, 0.225 mmol) was added. After 18 h, the reaction mixture was diluted with EtOAc (25 mL) and washed sequentially with aqueous HCl (0.1 M, 10 mL), saturated aqueous $NaHCO_3$ (10 mL) and brine (10 mL). The organic phase was dried ($Na_2SO_4$), filtered and concentrated in vacuo to afford 10.6 mg (57%) of the title compound.

EXAMPLE 85

2-{4-[(R)-2-((E)-3-Hydroxy-4-phenyl-but-1-enyl)-6-oxo-piperidin-1-yl]-but-2-ynyloxy}-acetamide Triethylamine (9.4 μL, 0.067 mmol) and ethyl chloroformate (3.1 μL, 0.032 mmol) were added sequentially to a solution of {4-[(R)-2-((E)-3-hydroxy-4-phenyl-but-1-enyl)-6-oxo-piperidin-1-yl]-but-2-ynyloxy}-acetic acid (11.8 mg, 0.032 mmol) in $CH_2Cl_2$ (0.2 mL) at 0° C. After 1 h at 0° C., ammonia (0.5 M in 1,4-dioxane, 0.32 mL, 0.16 mmol) was added and the reaction mixture was allowed to warm to rt. After 17 h at rt, the reaction mixture was treated with saturated aqueous $NaHCO_3$ (10 mL) and extracted with $CH_2Cl_2$ (3×10 mL). The combined extracts were dried ($Na_2SO_4$), filtered and concentrated in vacuo to afford 11 mg (93%) of the title compound.

EXAMPLE 86

{4-[(R)-2-Oxo-6-(3-oxo-4-phenyl-butyl)-piperidin-1-yl]-but-2-ynyloxy}-acetic acid methyl ester A solution of {4-[(R)-2-Oxo-6-((E)-3-oxo-4-phenyl-but-1-enyl)-piperidin-1-yl]-but-2-ynyloxy}-acetic acid methyl ester (30 mg, 0.078 mmol) in toluene (2 mL) was added via cannula to a round-bottomed flask containing hydrido(triphenylphosphine)copper(I) hexamer (154 mg, 0.078 mmol) at −40° C. under nitrogen. The reaction was allowed to warm to rt and stirred for 2.5 h. The reaction was quenched with $NH_4OH/NH_4Cl$ (1:1, 8 mL) and extracted with EtOAc (3×10 mL). The combined extracts were dried washed with brine (10 mL) then dried ($Na_2SO_4$), filtered and concentrated in vacuo. Purification of the residue by flash column chromatography on silica gel (20%→40% EtOAc/$CH_2Cl_2$, gradient) afforded 23.4 mg (78%) of the title compound.

EXAMPLE 87

{4-[(R)-2-Oxo-6-(3-oxo-4-phenyl-butyl)-piperidin-1-yl]-but-2-ynyloxy}-acetic acid In accordance with the procedure of example 2, {4-[(R)-2-oxo-6-(3-oxo-4-phenyl-butyl)-piperidin-1-yl]-but-2-ynyloxy}-acetic acid methyl ester (6.5 mg, 0.017 mmol) was converted into 5.2 mg (83%) of the title compound.

EXAMPLES 88 AND 89

{4-[(R)-2-(3-Hydroxy-4-phenyl-butyl)-6-oxo-piperidin-1-yl]-but-2-ynyloxy}-acetic acid methyl ester and (R)-1-[4-(2-hydroxy-ethoxy)-but-2-ynyl]-6-(3-hydroxy-4-phenyl-butyl)-piperidin-2-one Sodium borohydride (4.4 mg, 0.12 mmol) followed by MeOH (0.2 mL) was added to a solution of {4-[(R)-2-oxo-6-(3-oxo-4-phenyl-butyl)-piperidin-1-yl]-but-2-ynyloxy}-acetic acid methyl ester (15 mg, 0.039 mmol) in $CH_2Cl_2$ (0.6 mL) at 0° C. After 5 min at 0° C. the reaction was quenched with aqueous HCl (0.2 M, 5 mL). The reaction mixture was extracted with $CH_2Cl_2$ (3×5 mL), then the combined extracts were dried ($Na_2SO_4$), filtered and concentrated in vacuo. Purification of the residue by flash column chromatography on silica gel ($CH_2Cl_2$→5% MeOH/$CH_2Cl_2$) afforded 13 mg (86%) of {4-[(R)-2-(3-hydroxy-4-phenyl-butyl)-6-oxo-piperidin-1-yl]-but-2-ynyloxy}-acetic acid methyl ester and 2 mg (14%) of (R)-1-[4-(2-hydroxy-ethoxy)-but-2-ynyl]-6-(3-hydroxy-4-phenyl-butyl)-piperidin-2-one.

EXAMPLE 90

{4-[(R)-2-(3-Hydroxy-4-phenyl-butyl)-6-oxo-piperidin-1-yl]-but-2-ynyloxy}-acetic acid In accordance with the procedure of example 2, {4-[(R)-2-(3-hydroxy-4-phenyl-butyl)-6-oxo-piperidin-1-yl]-but-2-ynyloxy}-acetic acid methyl ester (11 mg, 0.028 mmol) was converted into 3.8 mg (36%) of the title compound.

EXAMPLE 91

{4-[(R)-2-Oxo-6-((E)-3-oxo-4-phenyl-but-1-enyl)-piperidin-1-yl]-but-2-ynyloxy}-acetonitrile Step 1. (4-Hydroxy-but-2-ynyloxy)-acetonitrile Sodium hydride (60% dispersion in oil, 7.5 g, 188 mmol) was added to a solution of 2-butyne-1,4-diol (16.1 g, 187 mmol) in THF (150 mL) at 0° C. under nitrogen. After 1 h at 0° C., bromoacetonitrile (8.33 mL, 120 mmol) was added slowly and the reaction was allowed to warm to rt. After 22 h at rt, the reaction was quenched with 1 N HCl (150 mL) and extracted with EtOAc (3×150 mL). The combined extracts were washed with brine (150 mL), dried ($Na_2SO_4$), filtered and concentrated in vacuo. Purification of the residue by flash column chromatography on silica gel ($CH_2Cl_2$→2% MeOH/$CH_2Cl_2$, gradient) afforded 4.35 μg (29%) of (4-hydroxy-but-2-ynyloxy)-acetonitrile.

Step 2. (4-Iodo-but-2-ynyloxy)-acetonitrile

Triphenylphosphine (10.94 g, 41.7 mmol) and iodine (10.55 g, 41.6 mmol were added sequentially to a solution of (4-hydroxy-but-2-ynyloxy)-acetonitrile (4.35 g, 34.8 mmol) in $CH_2Cl_2$ (100 mL). The reaction mixture became homogeneous after 5 min at rt and imidazole (2.76 g, 40.5 mmol) was added slowly in small portions. After 1.5 h at rt, the reaction was filtered through activity I basic alumina, washing with 20% EtOAc/Hexane. The filtrate was concentrated in vacuo then purified by flash column chromatography on silica gel (hexane→10% EtOAc/hexane, gradient) to afford 7.51 g (92%) of (4-iodo-but-2-ynyloxy)-acetonitrile.

Step 3. {4-[(R)-2-(1-Ethoxy-ethoxymethyl)-6-oxo-piperidin-1-yl]-but-2-ynyloxy}-acetonitrile Sodium hydride (60% dispersion in oil, 600 mg, 15.0 mmol) was added to a solution of (R)-6-(1-ethoxyethoxymethyl)-piperidin-2-one (from example 50, step 1, 3.00 g, 14.9 mmol) in DMF (20 mL) at 0° C. After 1 h at 0° C., (4-iodo-but-2-ynyloxy)-acetonitrile (3.50 g, 14.9 mmol) in DMF (10 mL) was added via cannula and the reaction was allowed to warm to rt. After 16.5 h at rt, the reaction was treated with saturated aqueous $NH_4Cl$ (100 mL) and extracted with EtOAc (3×100 mL). The combined extracts were washed with water (2×100 mL) and brine (2×100 mL) then dried ($Na_2SO_4$), filtered and concentrated in vacuo. Purification of the residue by flash column chromatography on silica gel ($CH_2Cl_2$→50% EtOAc/$CH_2Cl_2$, gradient) afforded 1.83 g (40%) of {4-[(R)-2-(1-ethoxy-ethoxymethyl)-6-oxo-piperidin-1-yl]-but-2-ynyloxy}-acetonitrile.

Step 4. [4-((R)-2-Hydroxymethyl-6-oxo-piperidin-1-yl)-but-2-ynyloxy]-acetonitrile Trifluoroacetic acid (0.5 mL, 6.5 mmol) was added to a solution of {4-[(R)-2-(1-ethoxy-ethoxymethyl)-6-oxo-piperidin-1-yl]-but-2-ynyloxy}-acetonitrile (290 mg, 0.94 mmol) in $CH_2Cl_2$ (3 mL). After 1 h at rt, the reaction mixture was quenched with saturated aqueous $NaHCO_3$ (20 mL) and extracted with $CH_2Cl_2$ (3×20 mL). Combined extracts were dried ($Na_2SO_4$), filtered and concentrated in vacuo. Purification of the residue by flash column chromatography on silica gel ($CH_2Cl_2$→3% MeOH/$CH_2Cl_2$, gradient) afforded 118 mg (53%) of [4-((R)-2-hydroxymethyl-6-oxo-piperidin-1-yl)-but-2-ynyloxy]-acetonitrile.

Step 5. [4-((R)-2-Formyl-6-oxo-piperidin-1-yl)-but-2-ynyloxy]-acetonitrile

EDCI (288 mg, 1.50 mmol) was added to a solution of [4-((R)-2-hydroxymethyl-6-oxo-piperidin-1-yl)-but-2-ynyloxy]-acetonitrile (118 mg, 0.50 mmol) in benzene (4 mL). The reaction mixture was cooled to 0° C. and DMSO (0.14 mL, 2.0 mmol) was added. After 5 min at 0° C., pyridinium trifluoroacetate (106 mg, 0.55 mmol) was added. The reaction was allowed to warm to rt and then was stirred at rt for 3 h. The solution was decanted from the oily residue and the residue was washed with benzene (3×5 mL). The combined benzene phases were concentrated in vacuo to afford crude [4-((R)-2-formyl-6-oxo-piperidin-1-yl)-but-2-ynyloxy]-acetonitrile, which was used without further purification.

Step 6. {4-[(R)-2-Oxo-6-((E)-3-oxo-4-phenyl-but-1-enyl)-piperidin-1-yl]-but-2-ynyloxy}-acetonitrile Sodium hydride (60% dispersion in oil, 18 mg, 0.45 mmol) was added to a solution of dimethyl 2-oxo-3-phenylpropylphosphonate (110 mg, 0.45 mmol) in THF (1.5 mL) at 0° C. After 1 h at 0° C., a solution of [4-((R)-2-formyl-6-oxo-piperidin-1-yl)-but-2-ynyloxy]-acetonitrile (0.50 mmol, crude from step 5) in THF (1.5 mL) was added via cannula. The reaction was allowed to warm to rt. After 18 h at rt, the reaction was quenched with aqueous acetic acid (50%, 10 mL) and extracted with EtOAc (3×20 mL). The combined organic phase was washed with brine (25 mL), dried ($Na_2SO_4$), filtered and concentrated in vacuo. Purification of the residue by flash column chromatography on silica gel (10%→40% EtOAc/$CH_2Cl_2$, gradient) afforded 75 mg (48%) of the title compound.

EXAMPLE 92

{4-[(R)-2-Oxo-6-(3-oxo-4-phenyl-butyl)-piperidin-1-yl]-butoxy}-acetonitrile

Palladium on carbon (10 wt. %, 7 mg) was added to a solution of {4-[(R)-2-oxo-6-((E)-3-oxo-4-phenyl-but-1-enyl)-piperidin-1-yl]-but-2-ynyloxy}-acetonitrile (35 mg, 0.10 mmol) in MeOH (3.0 mL). A hydrogen atmosphere was established by evacuating and refilling with hydrogen (3×) and the reaction mixture was stirred under a balloon of hydrogen for 19 h. The reaction mixture was filtered through celite, washing with MeOH, and the filtrate was concentrated in vacuo. Purification of the residue by flash column chromatography on silica gel ($CH_2Cl_2$→2% MeOH/$CH_2Cl_2$, gradient) afforded 20 mg (56%) of the title compound.

EXAMPLE 93

{4-[(R)-2-(3-Hydroxy-4-phenyl-butyl)-6-oxo-piperidin-1-yl]-butoxy}-acetonitrile

Lithium aluminum hydride (1.0 M in THF, 0.02 mL, 0.02 mmol) was added to a solution of {4-[(R)-2-oxo-6-(3-oxo-4-phenyl-butyl)-piperidin-1-yl]-butoxy}-acetonitrile (15.7 mg, 0.044 mmol) in THF (0.75 mL) at 0° C. After 2 h at 0° C. the reaction was quenched with saturated aqueous $NH_4Cl$ (5 mL) and extracted with (3×5 mL). The combined organic phase was dried ($Na_2SO_4$), filtered and concentrated in vacuo to afford 12.3 mg (78%) of the title compound.

EXAMPLE 94

(R)-1-[4-(2-Amino-ethoxy)-butyl]-6-(3-hydroxy-4-phenyl-butyl)-piperidin-2-one

Raney nickel (5 mg) was added to a solution of {4-[(R)-2-(3-hydroxy-4-phenyl-butyl)-6-oxo-piperidin-1-yl]-butoxy}-acetonitrile (10.5 mg, 0.029 mmol) in MeOH (1.5 mL). A hydrogen atmosphere was established by evacuating and refilling with hydrogen (3×) and the reaction mixture was stirred under a balloon of hydrogen for 19 h. The reaction mixture was filtered through celite, washing with MeOH, and the filtrate was concentrated in vacuo to afford 6.9 mg (65%) of the title compound.

These compounds are tested for in vitro activity as described below and the results given in the Table.

Human Recombinant $EP_1$, $EP_2$, $EP_3$, $EP_4$, FP, TP, IP and DP Receptors: Stable Transfectants.

Plasmids encoding the human $EP_1$, $EP_2$, $EP_3$, $EP_4$, FP, TP, IP and DP receptors were prepared by cloning the respective coding sequences into the eukaryotic expression vector pCEP4 (Invitrogen). The pCEP4 vector contains an Epstein Barr virus (EBV) origin of replication, which permits episomal replication in primate cell lines expressing EBV nuclear antigen (EBNA-1). It also contains a hygromycin resistance gene that is used for eukaryotic selection. The cells employed for stable transfection were human embryonic kidney cells (HEK-293) that were transfected with and express the EBNA-1 protein. These HEK-293-EBNA cells (Invitrogen) were grown in medium containing Geneticin (G418) to maintain expression of the EBNA-1 protein. HEK-293 cells were grown in DMEM with 10% fetal bovine serum (FBS), 250 μg $ml^{-1}$ G418 (Life Technologies) and 200 μg $ml^{-1}$ gentamicin or penicillin/streptomycin. Selection of stable transfectants was achieved with 200 μg $ml^{-1}$ hygromycin, the optimal concentration being determined by previous hygromycin kill curve studies.

For transfection, the cells were grown to 50-60% confluency on 10 cm plates. The plasmid pCEP4 incorporating cDNA inserts for the respective human prostanoid receptor (20 μg) was added to 500 μl of 250 mM $CaCl_2$. HEPES buffered saline×2 (2×HBS, 280 mM NaCl, 20 mM HEPES acid, 1.5 mM $Na_2$ $HPO_4$, pH 7.05-7.12) was then added dropwise to a total of 500 μl, with continuous vortexing at room temperature. After 30 min, 9 ml DMEM were added to the mixture. The DNA/DMEM/calcium phosphate mixture was then added to the cells, which had been previously rinsed with 10 ml PBS. The cells were then incubated for 5 hr at 37° C. in humidified 95% air/5% $CO_2$. The calcium phosphate solution was then removed and the cells were treated with 10% glycerol in DMEM for 2 min. The glycerol solution was then replaced by DMEM with 10% FBS. The cells were incubated overnight and the medium was replaced by DMEM/10% FBS containing 250 μg $ml^{-1}$ G418 and penicillin/streptomycin. The following day hygromycin B was added to a final concentration of 200 μg $ml^{-1}$.

Ten days after transfection, hygromycin B resistant clones were individually selected and transferred to a separate well on a 24 well plate. At confluence each clone was transferred to one well of a 6 well plate, and then expanded in a 10 cm dish. Cells were maintained under continuous hygromycin selection until use.

Radioligand Binding

Radioligand binding studies on plasma membrane fractions prepared from cells were performed as follows. Cells washed with TME buffer were scraped from the bottom of the flasks and homogenized for 30 sec using a Brinkman PT 10/35 polytron. TME buffer was added as necessary to achieve a 40 ml volume in the centrifuge tubes. TME is comprised of 50 mM TRIS base, 10 mM $MgCl_2$, 1 mM EDTA; pH 7.4 is achieved by adding 1 N HCl. The cell homogenate was centrifuged at 19,000 rpm for 20-25 min at 4° C. using a Beckman Ti-60 or Tt-70 rotor. The pellet was then resuspended in TME buffer to provide a final protein concentration of 1 mg/ml, as determined by Bio-Rad assay. Radioligand binding assays were performed in a 100 μl or 200 μl volume.

The binding of [$^3$H] $PGE_2$ (specific activity 165 Ci/mmol) was determined in duplicate and in at least 3 separate experiments. Incubations were for 60 min at 25° C. and were terminated by the addition of 4 ml of ice-cold 50 mM TRIS-HCl followed by rapid filtration through Whatman GF/B filters and three additional 4 ml washes in a cell harvester (Brandel). Competition studies were performed using a final concentration of 2.5 or 5 nM [3H] $PGE_2$ and non-specific binding was determined with 10-5 M unlabelled $PGE_2$.

For all radioligand binding studies, the criteria for inclusion were >50% specific binding and between 500 and 1000 displaceable counts or better.

While not intending to limit the scope of the invention in any way, the results of FIG. 1 suggest that the compounds described herein are selective EP4 agonists, and will thus be useful for the treatment of inflammatory bowel disease.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A method comprising administering a therapeutically effective amount of compound to a mammal suffering from an inflammatory bowel disease for the treatment of said disease, said compound represented by the general formula I;

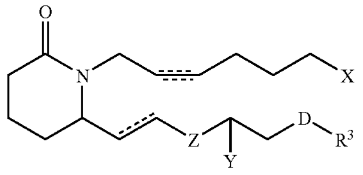

wherein hatched lines represent the α configuration, a triangle represents the β configuration, a wavy line represents either the α configuration or the β configuration and a dotted line represents the presence or absence of a double bond;

D represents a covalent bond or $CH_2$, O, S or NH;

X is $CO_2R$, $CONR_2$,

Y is $CH_2OH$;

Z is $CH_2$ or a covalent bond;

R is H or $R^2$;

$R^1$ is H, $R^2$, phenyl, or $COR^2$;

$R^2$ is $C_1$-$C_5$ lower alkyl or alkenyl and $R^3$ is selected from the group consisting of $R^2$, phenyl, thienyl, furanyl, pyridyl, benzothienyl, benzofuranyl, naphthyl, or substituted derivatives thereof, wherein the substituents maybe selected from the group consisting of $C_1$-$C_5$ alkyl, halogen, $CF_3$, CN, $NO_2$, $NR_2$, $CO_2R$ and OR.

2. The method according to claim 1 comprising

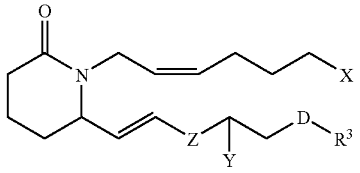

or a pharmaceutically acceptable salt or a prodrug thereof.

3. The method of claim 1 wherein Z represents a covalent bond.

4. The method of claim 1 wherein D is $CH_2$.

5. The method of claim 1 wherein X is $CO_2$ R.

6. The method of claim 5 wherein R is H, or $C_1$-$C_5$ alkyl.

7. The method of claim 6 wherein R is selected from the group consisting of H and methyl.

8. The method of claim 1 wherein $R^1$ is H.

9. The method of claim 1 wherein $R^3$ is selected from the group consisting of phenyl and n-propyl.

10. The method of claim 1 wherein said compound is selected from the group consisting of 7-[2-oxo-6-((E)-3-oxo-oct-1-enyl)-piperidin-1-yl]-hept-5-ynoic acid methyl ester, 7-[2-oxo-6-((E)-3-oxo-oct-1-enyl)-piperidin-1-yl]-hept-5-ynoic acid, (Z)-7-[2-oxo-6-((E)-3-oxo-oct-1-enyl)-piperidin-1-yl]-hept-5-enoic acid methyl ester, (Z)-7-[2-oxo-6-((E)-3-oxo-oct-1-enyl)-piperidin-1-yl]-hept-5-enoic acid, 7-[2-oxo-6-(3-oxo-octyl)-piperidin-1-yl]-heptanoic acid methyl ester, 7-[2-oxo-6-(3-oxo-octyl)-piperidin-1-yl]-heptanoic acid, 7-[2-(3-hydroxy-octyl)-6-oxo-piperidin-1-yl]-heptanoic acid methyl ester, 7-[2-(3-hydroxy-octyl)-6-oxo-piperidin-1-yl]-heptanoic acid, (Z)-7-[2-((E)-3-hydroxy-oct-1-enyl)-6-oxo-piperidin-1-yl]-hept-5-enoic acid methyl ester, (Z)-7-[2-((E)-3-hydroxy-oct-1-enyl)-6-oxo-piperidin-1-yl]-hept-5-enoic acid, 7-[2-oxo-6-((E)-3-oxo-oct-1-enyl)-piperidin-1-yl]-heptanoic acid methyl ester, 7-[2-oxo-6-((E)-3-oxo-oct-1-enyl)-piperidin-1-yl]-heptanoic acid, 7-[2-((E)-3-hydroxy-oct-1-enyl)-6-oxo-piperidin-1-yl]-heptanoic acid methyl ester, 7-[2-((E)-3-hydroxy-oct-1-enyl)-6-oxo-piperidin-1-yl]-heptanoic acid, 7-[2-oxo-6-((E)-3-oxo-4-phenyl-but-1-enyl)-piperidin-1-yl]-heptanoic acid methyl ester, 7-[2-oxo-6-((E)-3-oxo-4-phenyl-but-1-enyl)-piperidin-1-yl]-heptanoic acid, 7-[2-((E)-3-hydroxy-4-phenyl-but-1-enyl)-6-oxo-piperidin-1-yl]-heptanoic acid methyl ester, 7-[2-((E)-3-hydroxy-4-phenyl-but-1-enyl)-6-oxo-piperidin-1-yl]-heptanoic acid, 7-[2-(3-hydroxy-4-phenyl-butyl)-6-oxo-piperidin-1-yl]-heptanoic acid methyl ester, 7-[2-(3-hydroxy-4-phenyl-butyl)-6-oxo-piperidin-1-yl]-heptanoic acid, 7-[2-oxo-6-(3-oxo-4-phenyl-butyl)-piperidin-1-yl]-heptanoic acid methyl ester, 7-[2-oxo-6-(3-oxo-4-phenyl-butyl)-piperidin-1-yl]-heptanoic acid, 7-[2-oxo-6-((E)-3-oxo-4-phenyl-but-1-enyl)-piperidin-1-yl]-hept-5-ynoic acid methyl ester, 7-[2-oxo-6-((E)-3-oxo-4-phenyl-but-1-enyl)-piperidin-1-yl]-hept-5-ynoic acid, (Z)-7-[2-oxo-6-((E)-3-oxo-4-phenyl-but-1-enyl)-piperidin-1-yl]-hept-5-enoic acid methyl ester, (Z)-7-[2-oxo-6-((E)-3-oxo-4-phenyl-but-1-enyl)-piperidin-1-yl]-hept-5-enoic acid, (Z)-7-[2-((E)-3-hydroxy-4-phenyl-but-1-enyl)-6-oxo-piperidin-1-yl]-hept-5-enoic acid methyl ester (Z)-7-[2-((E)-3-hydroxy-4-phenyl-but-1-enyl)-6-oxo-piperidin-1-yl]-hept-5-enoic acid 7-[(R)-2-((E)-3-Hydroxy-4-phenyl-but-1-enyl)-6-oxo-piperidin-1-yl]-heptanoic acid methyl ester, 7-[(R)-2-((E)-3-Hydroxy-4-phenyl-but-1-enyl)-6-oxo-piperidin-1-yl]-heptanoic acid, 7-[(R)-2-((E)-3-Hydroxy-oct-1-enyl)-6-oxo-piperidin-1-yl]-heptanoic acid methyl ester, 7-[(R)-2-((E)-3-Hydroxy-oct-1-enyl)-6-oxo-piperidin-1-yl]-heptanoic acid, 7-[(R)-2-(3-Hydroxy-octyl)-6-oxo-piperidin-1-yl]-heptanoic acid methyl ester, 7-[(R)-2-(3-Hydroxy-octyl)-6-oxo-piperidin-1-yl]-heptanoic acid, 7-[(R)-2-((E)-3-Hydroxy-oct-1-enyl)-6-oxo-piperidin-1-yl]-hept-5-ynoic acid methyl ester, (R)-1-(7-hydroxy-hept-2-ynyl)-6-((E)-3-hydroxy-oct-1-enyl)-piperidin-2-one, (Z)-7-[(R)-2-((E)-3-Hydroxy-oct-1-enyl)-6-oxo-piperidin-1-yl]-hept-5-enoic acid methyl ester, (Z)-7-[(R)-2-((E)-3-Hydroxy-oct-1-enyl)-6-oxo-piperidin-1-yl]-hept-5-enoic acid, (Z)-7-[(R)-2-((E)-3-Hydroxy-4-phenyl-but-1-enyl)-6-oxo-piperidin-1-yl]-hept-5-enoic acid methyl ester, (Z)-7-[(R)-2-((E)-3-Hydroxy-4-phenyl-but-1-enyl)-6-oxo-piperidin-1-yl]-hept-5-enoic acid, 7-[(R)-2-((E)-3-Hydroxy-4-phenyl-but-1-enyl)-6-oxo-piperidin-1-yl]-hept-5-ynoic acid methyl ester 7-[(R)-2-((E)-3-Hydroxy-4-phenyl-but-1-enyl)-6-oxo-piperidin-1-yl]-hept-5-ynoic acid, 7-[(R)-2-((E)-3-Hydroxy-4-phenyl-but-1-enyl)-6-oxo-piperidin-1-yl]-heptanoic acid isopropyl ester, 7-[(R)-2-((E)-3-Hydroxy-4-phenyl-but-1-enyl)-6-oxo-piperidin-1-yl]-heptanoic acid amide, and 7-[(R)-2-((E)-3-Hydroxy-4-phenyl-but-1-enyl)-6-oxo-piperidin-1-yl]-heptanoic acid isopropyl ester.

11. A method comprising administering a compound to a mammal suffering from an inflammatory bowel disease for the treatment of said disease, said compound having an α and an ω chain comprising

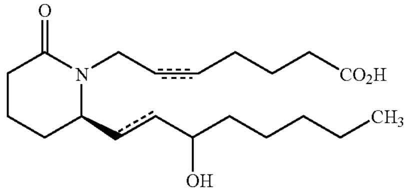

or a derivative thereof, wherein a dotted line indicates the presence or absence of a bond, and wherein said derivative has a structure as shown above except that from 1 to 2 alterations are made to the α chain and/or the ω chain, an alteration consisting of adding, removing, or substituting a non-hydrogen atom or a pharmaceutically acceptable salt or a prodrug thereof.

12. The method of claim 1 wherein said compound comprises

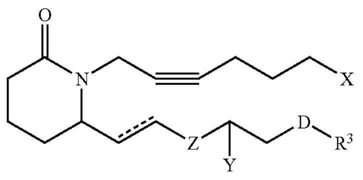

or a pharmaceutically acceptable salt or a prodrug thereof wherein Z is a covalent bond.

13. The method of claim 12 wherein $R^3$ is thienyl or substituted thienyl.

14. The method of claim 13 wherein D is a covalent bond or $CH_2$.

15. The method of claim 1 wherein X is $CONR_2$, $CONMe_2$, CONHMe, CONHEt, $CON(OCH_3)CH_3$, $CONH_2$, $CON(CH_2CH_2OH)_2$, or $CONH(CH_2CH_2OH)$; and Z is a covalent bond.

16. A method comprising administering a compound to a mammal suffering from an inflammatory bowel disease for the treatment of said disease, said compound comprising

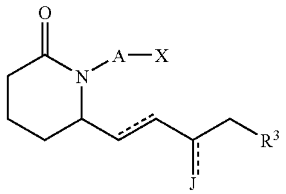

or a pharmaceutically acceptable salt or a prodrug thereof;

wherein a dotted line represents the presence or absence of a double bond;

A is $-(CH_2)_6-$, cis $-CH_2CH{=}CH-(CH_2)_3-$, or $-CH_2CH{\equiv}CH-(CH_2)_3-$, wherein 1 or 2 carbon atoms may be substituted with S or O;

X is $CO_2R$, $CONR_2$,

J is —OH;

R is H or $R^2$;

$R^2$ is $C_1$-$C_5$ lower alkyl or alkenyl and $R^3$ is selected from the group consisting of $R^2$, phenyl, thienyl, furanyl, pyridyl, benzothienyl, benzofuranyl, naphthyl or substituted derivatives thereof, wherein the substituents maybe selected from the group consisting of $C_1$-$C_5$ alkyl, halogen, $CF_3$, CN, $NO_2$, $NR^2$, $CO_2R$ and OR.

17. The method of claim 16 wherein X is $CONR_2$, $CONMe_2$, CONHMe, CONHEt, $CON(OCH_3)CH_3$, $CONH_2$, $CON(CH_2CH_2OH)_2$, or $CONH(CH_2CH_2OH)$.

18. The method of claim 16 wherein said compound comprises

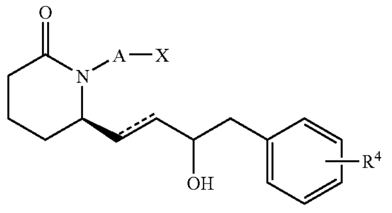

or a pharmaceutically acceptable salt or a prodrug thereof, wherein a triangle represents the β configuration, and $R^4$ is selected from the group consisting of H, $C_1$-$C_5$ alkyl, halogen, $CF_3$, CN, $NO_2$, $NR_2$, $CO_2R$ and OR.

19. The method of claim 18 wherein said compound comprises

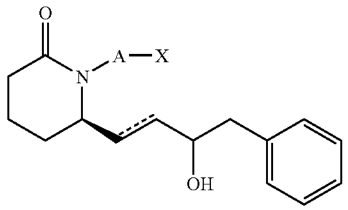

or a pharmaceutically acceptable salt or a prodrug thereof.

20. A method comprising administering a compound to a mammal suffering from an inflammatory bowel disease for the treatment of said disease, said compound having an α and an ω chain comprising

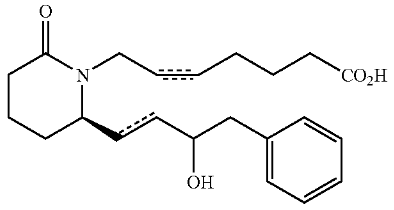

or a derivative thereof, wherein a dotted line indicates the presence or absence of a bond, and wherein said derivative has a structure as shown above except that from 1 to 2 alterations are made to the α chain and/or the ω chain, an alteration consisting of a. adding, removing, or substituting a non-hydrogen atom, d. converting a phenyl moiety to a pyridinyl, furyl, or thienyl moiety, or e. adding a substituent comprising from 1 to 3 non-hydrogen atoms to an aromatic or a heteroaromatic ring;

or a pharmaceutically acceptable salt or a prodrug thereof.

21. The method of claim 20 wherein said compound comprises

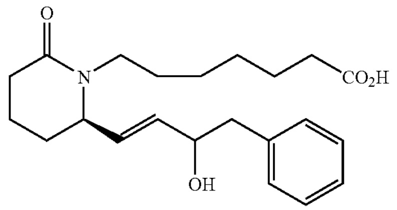

or a pharmaceutically acceptable salt or a prodrug thereof.

22. The method of claim 20 wherein said compound comprises

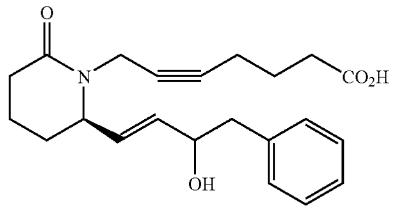

or a pharmaceutically acceptable salt or a prodrug thereof.

23. The method of claim 1 wherein said irritable bowel disease is Crohn's disease.

24. The method of claim 1 wherein said irritable bowel disease is ulcerative colitis.

25. The method of claim 16 wherein said irritable bowel disease is Crohn's disease.

26. The method of claim 16 wherein said irritable bowel disease is ulcerative colitis.

27. An oral or rectal dosage form comprising a compound having the general formula I;

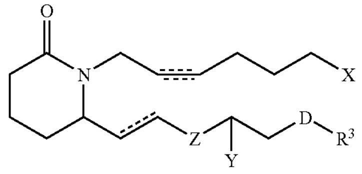

wherein hatched lines represent the α configuration, a triangle represents the β configuration, a wavy line represents either the α configuration or the β configuration and a dotted line represents the presence or absence of a double bond;

D represents a covalent bond or $CH_2$, O, S or NH;

X is $CO_2R$, $CONR_2$, $CH_2OR$, $P(O)(OR)_2$, $CONRSO_2R$, $SO_2NR_2$ or

Y is $CH_2OH$;

Z is $CH_2$ or a covalent bond;

R is H or $R^2$;

$R^1$ is H, $R^2$, phenyl, or $COR^2$;

$R^2$ is $C_1$-$C_5$ lower alkyl or alkenyl and $R^3$ is selected from the group consisting of $R^2$, phenyl, thienyl, furanyl, pyridyl, benzothienyl, benzofuranyl, naphthyl, or substituted derivatives thereof, wherein the substituents maybe selected from the group consisting of $C_1$-$C_5$ alkyl, halogen, $CF_3$, CN, $NO_2$, $NR_2$, $CO_2R$ and OR.

28. An oral or rectal dosage form comprising a compound comprising

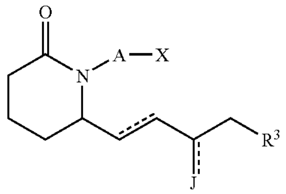

or a pharmaceutically acceptable salt or a prodrug thereof;

wherein a dotted line represents the presence or absence of a double bond;

A is $-(CH_2)_6-$, cis $-CH_2CH{=}CH-(CH_2)_3-$, or $-CH_2CH{\equiv}CH-(CH_2)_3-$, wherein 1 or 2 carbon atoms may be substituted with S or O;

X is $CO_2R$, $CONR_2$,

Y is $CH_2OH$;

J is —OH;

R is H or $R^2$;

$R^2$ is $C_1$-$C_5$ lower alkyl or alkenyl and $R^3$ is selected from the group consisting of $R^2$, phenyl, thienyl, furanyl, pyridyl, benzothienyl, benzofuranyl, naphthyl or substituted derivatives thereof, wherein the substituents maybe selected from the group consisting of $C_1$-$C_5$ alkyl, halogen, $CF_3$, CN, $NO_2$, $NR_2$, $CO_2R$ and OR.

* * * * *